United States Patent
Takikawa et al.

(10) Patent No.: US 8,206,954 B2
(45) Date of Patent: Jun. 26, 2012

(54) L-AMINO ACID-PRODUCING MICROORGANISM AND A METHOD FOR PRODUCING AN L-AMINO ACID

(75) Inventors: Rie Takikawa, Kawasaki (JP); Yoshihiko Hara, Kawasaki (JP); Gen Nonaka, Kawasaki (JP); Kazuhiro Takumi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/037,557

(22) Filed: Mar. 1, 2011

(65) Prior Publication Data

US 2011/0212496 A1 Sep. 1, 2011

Related U.S. Application Data

(63) Continuation of application No. PCT/JP2009/065475, filed on Sep. 4, 2009.

(30) Foreign Application Priority Data

Sep. 8, 2008 (JP) ................. 2008-229736
Feb. 16, 2009 (JP) ................. 2009-032839

(51) Int. Cl.
*C12P 13/24* (2006.01)
(52) U.S. Cl. ...................... 435/107; 435/189
(58) Field of Classification Search ................. 435/107, 435/189
See application file for complete search history.

(56) References Cited

U.S. PATENT DOCUMENTS

| | | | |
|---|---|---|---|
| 3,563,857 A | 2/1971 | Oki et al. | |
| 5,168,056 A | 12/1992 | Frost | |
| 5,776,736 A | 7/1998 | Frost et al. | |
| 5,906,925 A | 5/1999 | Liao | |
| 7,344,874 B2 | 3/2008 | Hara et al. | |
| 7,501,282 B2 | 3/2009 | Hara et al. | |
| 7,629,142 B2 | 12/2009 | Ueda et al. | |
| 7,785,845 B2 | 8/2010 | Hara et al. | |
| 7,785,858 B2 | 8/2010 | Kozlov et al. | |
| 2004/0265956 A1 | 12/2004 | Takikawa et al. | |
| 2006/0088919 A1 | 4/2006 | Rybak et al. | |
| 2009/0215131 A1 | 8/2009 | Hara et al. | |
| 2009/0226983 A1 | 9/2009 | Nonaka et al. | |
| 2009/0226984 A1 | 9/2009 | Nonaka et al. | |
| 2009/0286290 A1 | 11/2009 | Hara et al. | |
| 2010/0062496 A1 | 3/2010 | Takikawa et al. | |
| 2010/0112647 A1 | 5/2010 | Hara et al. | |
| 2010/0209977 A1 | 8/2010 | Takumi et al. | |
| 2010/0216196 A1 | 8/2010 | Nonaka et al. | |
| 2010/0233765 A1 | 9/2010 | Nonaka et al. | |
| 2010/0267094 A1 | 10/2010 | Kozlov et al. | |

FOREIGN PATENT DOCUMENTS

| | | |
|---|---|---|
| JP | 32-9393 | 11/1957 |
| JP | 05-244970 | 9/1993 |
| JP | 2000-189175 | 7/2000 |
| WO | WO2006/133898 | 12/2006 |

OTHER PUBLICATIONS

Kikuchi, M., et al., "Glutamic Acid," biotechnology of amino acid production, Ed. AIDA, K., et al., Tokyo, Kodansha Ltd. 1986, pp. 101-116 (corresponding to Kunihiko Akashi et al., "Amino acid fermentation," Japan Scientific Societies Press, 1986, pp. 195-215).
International Preliminary Report on Patentability for PCT Patent App. No. PCT/JP2009/065475 (Apr. 28, 2011).
Cha, J-S, et al., "Identification and Characterization of a *Pantoea citrea* Gene Encoding Glucose Dehydrogenase That is Essential for Causing Pink Disease of Pineapple," Appl. Environmen. Microbiol. 1997;63(1):71-76.
Hommes, R. W. J., et al., "Evidence of a quinoprotein glucose dehydrogenase apoenzyme in several strains of *Escherichia coli*," FEMS Microbiol. Lett. 1984;24:329-333.
Pujol, C. J., et al., "gdhB, a gene encoding a second quinoprotein glucose dehydrogenase in *Pantoea citrea*, is required for pink disease of pineapple," Microbiol. 1999;145:1217-1226.
Shigematsu, T., et al., "Cellulose Production from Glucose Using a Glucose Dehydrogenase Gene (gdh)-Deficient Mutant of Gluconacetobacter xylinus and its Use for Bioconversion of Sweet Potato Pulp," J. Biosci. Bioeng. 2005;99(4):415-422.
International Search Report for PCT Patent App. No. PCT/JP2009/065475 (Oct. 6, 2009).

*Primary Examiner* — Tekchand Saidha
(74) *Attorney, Agent, or Firm* — Shelly Guest Cermak; Cermak Nakajima LLP

(57) ABSTRACT

An L-amino acid is produced by culturing a bacterium belonging to the family Enterobacteriaceae, which has an L-amino acid-producing ability and inherently has a native activity of a glucose dehydrogenase that uses pyrroloquinoline quinone as a coenzyme, but has been modified so that the activity of the glucose dehydrogenase is reduced, in a medium, and collecting the L-amino acid from the medium.

7 Claims, 3 Drawing Sheets

Fig. 3

SEQ ID NO.:67

Sequence of native promoter Pnlp

```
                          -35(Pnlp2)                    -10(Pnlp2)
aaaacgtgaggaaatacctggattttttcctggttattttgccgcaggtcagcgtatcgtg
         -35(Pnlp1)                       -10(Pnlp1)   transcr start
aagatcttttccagtgttcagtagggtgccttgcacggtaattatgtcactggttattaa
                        M  S
  ccaattttcctgggggataaatgagc
```

L-AMINO ACID-PRODUCING MICROORGANISM AND A METHOD FOR PRODUCING AN L-AMINO ACID

This application is a Continuation of, and claims priority under 35 U.S.C. §120 to, International Application No. PCT/JP2009/065475, filed Sep. 4, 2009, and claims priority therethrough under 35 U.S.C. §119 to Japanese Patent Application Nos. 2008-229736, filed Sep. 8, 2008, and 2009-032839, filed Feb. 16, 2009, the entireties of which are incorporated by reference herein. Also, the Sequence Listing on compact disk filed herewith is hereby incorporated by reference (File name: 2011-03-01T_US-458_Seq_List; File size: 86 KB; Date recorded: Mar. 1, 2011).

BACKGROUND OF THE INVENTION

1. Field of the Invention

The presently disclosed subject matter relates to a method for producing an L-amino acid using a microorganism, in particular, a method for producing an L-amino acid such as L-glutamic acid, L-lysine, L-threonine, L-tryptophan, or the like. These are industrially useful L-amino acids, for example, L-glutamic acid is useful as a seasoning, and L-lysine, L-threonine, and L-tryptophan are useful as animal feed additives, health food ingredients, amino acid infusions, and so forth.

2. Brief Description of the Related Art

L-Amino acids are industrially produced by fermentation using various microorganisms. For example, L-glutamic acid is produced mainly by fermentation utilizing L-glutamic acid-producing bacteria of the so-called coryneform bacteria, which belong to the genus *Brevibacterium, Corynebacterium* or *Microbacterium*, or mutant strains thereof (see, for example, Kunihiko Akashi et al., "Amino acid fermentation", pp. 195-215, 1986, Japan Scientific Societies Press). As methods for producing L-glutamic acid by fermentation using other microorganisms, methods of using a microorganism belonging to the genus *Bacillus, Streptomyces, Penicillium* or the like (refer to, for example, Japanese Patent Laid-open (KOKAI) No. 5-244970), methods of using a microorganism belonging to the genus *Pseudomonas, Arthrobacter, Serratia, Candida* or the like (refer to, for example, U.S. Pat. No. 3,563,857), methods of using a microorganism belonging to the genus *Bacillus, Pseudomonas, Serratia, Aerobacter aerogenes* (currently referred to as *Enterobacter aerogenes*) or the like (refer to, for example, Japanese Patent Publication (KOKOKU) No. 32-9393), methods of using a mutant strain of *Escherichia coli* (refer to, for example, Japanese Patent Laid-open (KOKAI) No. 5-244970), and so forth are known. In addition, methods for producing L-glutamic acid using a microorganism belonging to the genus *Klebsiella, Erwinia, Pantoea* or *Enterobacter* have also been disclosed (refer to, for example, U.S. Pat. No. 3,563,857, Japanese Patent Publication No. 32-9393, Japanese Patent Laid-open No. 2000-189175).

Such methods for producing target substances such as L-amino acids by fermentation using a microorganism as described above include using a wild-type microorganism (wild-type strain), using an auxotrophic strain derived from a wild-type strain, using a metabolic regulation mutant strain derived from a wild-type strain as a strain resistant to one or more various drugs, using a strain which is both an auxotrophic strain and metabolic regulation mutant strain, and so forth.

In recent years, recombinant DNA techniques have been used in the production of target substances by fermentation. For example, L-amino acid productivity of a microorganism can be improved by enhancing expression of a gene encoding an L-amino acid biosynthetic enzyme (U.S. Pat. Nos. 5,168,056 and 5,776,736), or by enhancing the inflow of a carbon source into an L-amino acid biosynthesis system (U.S. Pat. No. 5,906,925).

An NAD(P)-dependent glucose dehydrogenase and a PQQ (pyrroloquinoline quinone)-dependent glucose dehydrogenase are both known. Furthermore, it is known that the PQQ-dependent type of glucose dehydrogenase (EC1.1.5.2) includes a soluble type and a membrane binding type, and the membrane binding type is present in the periplasmic space (space between outer membrane and inner membrane), and is widely present in enterobacteria. Hereafter, the glucose dehydrogenase present in the periplasmic space and which uses PQQ as a coenzyme is also referred to as "GCD".

It is known that some bacteria, such as *Escherichia coli*, are unable to synthesize PQQ, which is a coenzyme of GCD, and therefore can express the GCD activity only when PQQ is added (FEMS Microbiol. Lett., 24, 329-333, 1984). On the other hand, such bacteria as *Pantoea* bacteria are able to synthesize PQQ and have a GCD holoenzyme.

As techniques concerning GCD, a method of producing cellulose from glucose by using *Gluconobacter xylinus* in which the gene encoding GCD is deleted (J. Biosci. Bioeng., 99(4), 415-422, 2005), and a method of producing [5S,6S]-5,6-dihydroxycyclohexa-1,3-diene-1-carboxylic acid by using an *Escherichia* bacterium having reduced glucose dehydrogenase activity, or an *Escherichia* bacterium which is inherently deficient in the glucose dehydrogenase activity (International Patent Publication WO2006/133898) are known.

However, the influence of reduction of the GCD activity of a bacterium on L-amino acid-producing ability of the bacterium has not been previously reported.

SUMMARY OF THE INVENTION

Aspects of the present invention include providing a microorganism belonging to the family Enterobacteriaceae that can efficiently produce an L-amino acid, and a method for efficiently producing an L-amino acid by using such a microorganism.

The above aspects were achieved by finding that the ability to produce L-amino acids of an enterobacterium having an inherent or native GCD activity was improved by modifying the enterobacterium so that the GCD activity is reduced.

It is an aspect of the present invention to provide a method for producing an L-amino acid comprising culturing a bacterium which belongs to the family Enterobacteriaceae and is able to produce an L-amino acid in a medium, and collecting the L-amino acid from the medium or the bacterium, wherein the bacterium has been modified so that the native activity of glucose dehydrogenase, which uses pyrroloquinoline quinone as a coenzyme, is reduced as compared to a non-modified bacterium.

It is a further aspect of the present invention to provide the method as mentioned above, wherein the glucose dehydrogenase activity is reduced by inactivating a gcd gene encoding the glucose dehydrogenase.

It is a further aspect of the present invention to provide the method as mentioned above, wherein the gcd gene comprises a DNA encoding the amino acid sequence of SEQ ID NO: 2 or a variant thereof.

It is a further aspect of the present invention to provide the method as mentioned above, wherein the L-amino acid is selected from the group consisting of L-glutamic acid, L-lysine, L-threonine, L-arginine, L-histidine, L-isoleucine, L-valine, L-leucine, L-phenylalanine, L-tyrosine, L-tryptophan, L-cysteine, and combinations thereof.

It is a further aspect of the present invention to provide the method as mentioned above, wherein the L-amino acid is L-glutamic acid or L-cysteine.

It is a further aspect of the present invention to provide the method as mentioned above, wherein the L-amino acid is L-glutamic acid, and the activity or activities of an enzyme selected from the group consisting of citrate synthase, methyl citrate synthase, phosphoenolpyruvate carboxylase, glutamate dehydrogenase, and combinations thereof, are enhanced in the bacterium.

It is a further aspect of the present invention to provide the method as mentioned above, wherein the L-amino acid is L-cysteine, and the activity or activities of an enzyme selected from the group consisting of 3-phosphoglycerate dehydrogenase, serine acetyltransferase, sulfate/thiosulfate transport system, and combinations thereof, are enhanced, and/or expression of a yeaS gene is enhanced.

It is a further aspect of the present invention to provide the method as mentioned above, wherein the bacterium belongs to a genus selected from the group consisting of *Pantoea, Enterobacter, Erwinia, Klebsiella, Providencia, Salmonella, Serratia, Morganella*, and *Yersinia*.

BRIEF DESCRIPTION OF THE DRAWING FIGURES

FIG. 3 shows sequence of promoter Pnlp (SEQ ID NO: 67).

DESCRIPTION OF THE EXEMPLARY EMBODIMENTS

Figure 1:
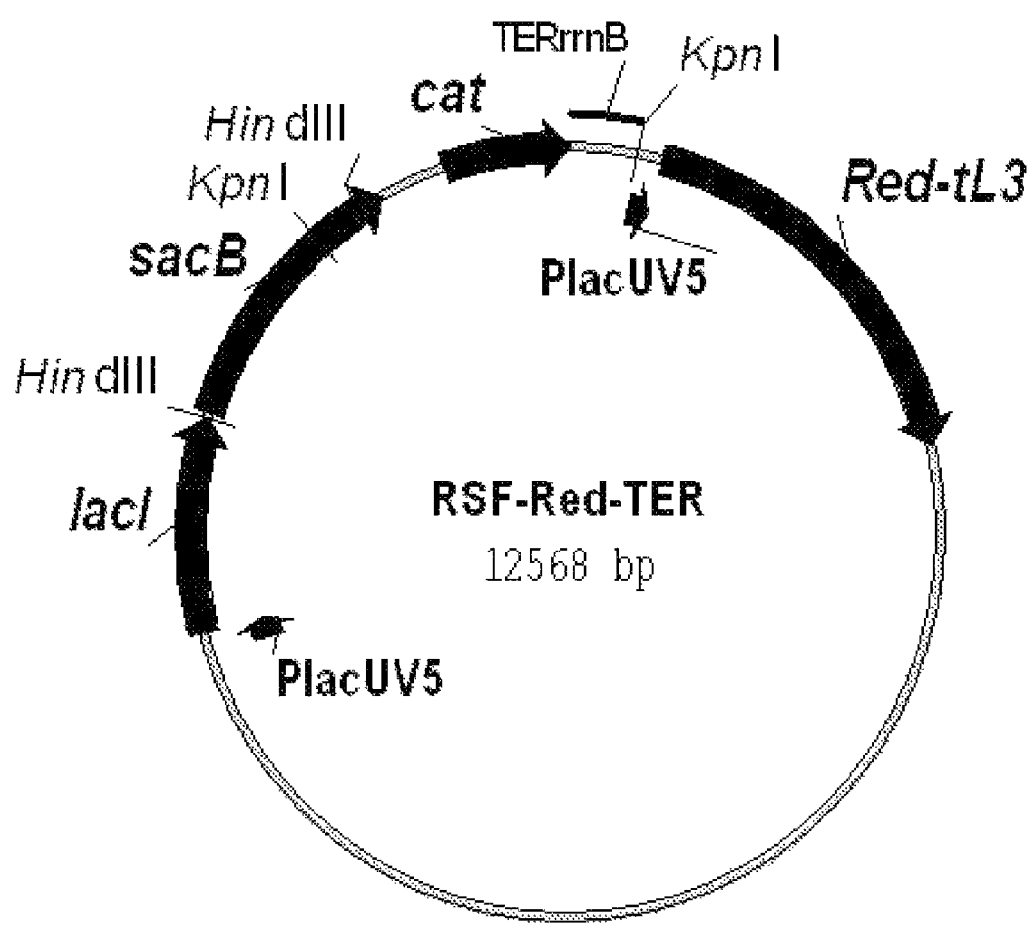
FIG. 1 shows structure of helper plasmid RSF-Red-TER.

Hereafter, the present invention will be explained in detail.

<1> Bacterium

The bacterium of the presently disclosed subject matter can belong to the family Enterobacteriaceae. The bacterium has a native or inherent GCD activity, and is able to produce an L-amino acid. Furthermore, the bacterium can be modified so that the native GCD activity is reduced. The bacterium of the presently disclosed subject matter can be obtained by modifying an L-amino acid producing bacterium belonging to the family Enterobacteriaceae which inherently has the GCD activity so that the GCD activity is reduced. Alternatively, the bacterium can also be obtained by imparting the ability to produce L-amino acid to a bacterium which belongs to the family Enterobacteriaceae, and inherently has native GCD activity, but which has already been modified so that the GCD activity is reduced, or enhancing the L-amino acid-producing ability of such a bacterium.

The type of the L-amino acid to be produced is not particularly limited, and examples include basic amino acids such as L-lysine, L-ornithine, L-arginine, L-histidine and L-citrulline, aliphatic amino acids such as L-isoleucine, L-alanine, L-valine, L-leucine and L-glycine, amino acids which are hydroxymonoaminocarboxylic acids such as L-threonine and L-serine, cyclic amino acids such as L-proline, aromatic amino acids such as L-phenylalanine, L-tyrosine and L-tryptophan, sulfur-containing amino acids such as L-cysteine, L-cystine and L-methionine, and acidic amino acids such as L-glutamic acid, L-aspartic acid, L-glutamine and L-asparagine. L-Glutamic acid, L-lysine, L-threonine and L-tryptophan are other examples. The microorganism of the presently disclosed subject matter can have the ability to produce two or more kinds of amino acids.

The term "L-amino acid" can include L-amino acids in free form and salts thereof, such as sulfates, hydrochlorides, carbonates, ammonium salts, sodium salts, and potassium salts thereof.

A bacterium having an L-amino acid-producing ability or being able to produce L-amino acids can refer to a bacterium which is able to produce an L-amino acid and excrete it into a medium, when the bacterium is cultured in the medium. The bacterium can produce L-amino acids such that the L-amino acids accumulate in the medium in an amount of 0.5 g/L or more, or in another example, 1.0 g/L or more.

Bacteria which can be used as a parent strain to obtain the bacterium that is modified so that the GCD activity is reduced, and methods for imparting or enhancing an L-amino acid-producing ability are exemplified below.

<2-1> Bacterium

The bacterium of the presently disclosed subject matter can belong to the family Enterobacteriaceae.

The family Enterobacteriaceae encompasses bacteria belonging to the genera of *Escherichia, Enterobacter, Erwinia, Klebsiella, Pantoea, Photorhabdus, Providencia, Salmonella, Serratia, Shigella, Morganella, Yersinia*, and so forth. In particular, bacteria classified into the family Enterobacteriaceae according to the taxonomy used by the NCBI (National Center for Biotechnology Information) database (www.ncbi.nlm.nih.gov/Taxonomy/Browser/wwwtax-.cgi?id=91347) can be used.

A "bacterium belonging to the genus *Escherichia*" can mean that the bacterium is classified into the genus *Escherichia* according to the classification known to a person skilled in the art of microbiology, although the bacterium is not particularly limited to these. Examples of the bacterium belonging to the genus *Escherichia* include, but are not limited to, *Escherichia coli* (*E. coli*).

Examples of the bacterium belonging to the genus *Escherichia* include, for example, the bacteria described in the work of Neidhardt et al. (Neidhardt F. C. Ed., 1996, *Escherichia coli* and *Salmonella*: Cellular and Molecular Biology/Second Edition, pp. 2477-2483, Table 1, American Society for Microbiology Press, Washington, D.C.). Specific examples include the *Escherichia coli* W3110 (ATCC 27325), *Escherichia coli* MG1655 (ATCC 47076) derived from the prototype wild-type strain K12 strain, and so forth.

These strains are available from, for example, the American Type Culture Collection (Address: P.O. Box 1549, Manassas, Va. 20108, United States of America). That is, accession numbers are given to each of the strains, and the strains can be ordered by using these numbers. The accession numbers of the strains are listed in the catalogue of the American Type Culture Collection.

Examples of the *Enterobacter* bacteria include, *Enterobacter agglomerans, Enterobacter aerogenes*, and so forth. Specifically, the strains exemplified in European Patent Laid-open No. 952221 can be used. In recent years, some bacteria of *Enterobacter agglomerans* have been reclassified as *Pantoea agglomerans, Pantoea ananatis*, or *Pantoea stewartii*, on the basis of nucleotide sequence analysis of the 16S rRNA etc. The microorganism can belong to either the genus *Enterobacter* or *Pantoea* so long as the microorganism is classified into the family Enterobacteriaceae.

Exemplary strains of the genus *Enterobacter* include the *Enterobacter agglomeranses* ATCC 12287 strain.

Exemplary strains of the *Pantoea* bacteria include *Pantoea ananatis, Pantoea stewartii, Pantoea agglomerans*, and *Pantoea citrea*. Specific examples include the following strains:

*Pantoea ananatis* AJ13355 (FERM BP-6614, European Patent Laid-open No. 0952221)
*Pantoea ananatis* AJ13356 (FERM BP-6615, European Patent Laid-open No. 0952221)
*Pantoea ananatis* AJ13601 (FERM BP-7207, European Patent Laid-open No. 0952221)

Although these strains were identified and deposited as *Enterobacter agglomerans* when they were isolated, they are currently classified as *Pantoea ananatis* on the basis of nucleotide sequence analysis of the 16S rRNA etc., as described above.

Examples of the *Erwinia* bacteria include *Erwinia amylovora* and *Erwinia carotovora*, and examples of the *Klebsiella* bacteria include *Klebsiella planticola*. Specific examples include the following strains:
*Erwinia amylovora* ATCC 15580
*Erwinia carotovora* ATCC 15713
*Klebsiella planticola* AJ13399 (FERM BP-6600, European Patent Laid-open No. 955368)
*Klebsiella planticola* AJ13410 (FERM BP-6617, European Patent Laid-open No. 955368).

The bacterium of the presently disclosed subject matter can be such an enterobacterium as described above, and can belong to the family Enterobacteriaceae such that it has an inherent or native GCD activity, and is able to produce L-amino acid. An enterobacterium which has an inherent or native GCD activity can mean a wild-type, or unmodified, bacterium in which the gcd gene is present and expresses a protein with GCD activity. Examples of such a bacterium belonging to the family Enterobacteriaceae include bacteria belonging to such a genus as *Pantoea, Enterobacter, Erwinia, Klebsiella, Providencia, Salmonella, Serratia, Morganella, Yersinia, Citrobacter*, and *Proteus*. More specifically, examples include the bacteria described in Int. J. Syst. Bacteriol., 39(1), 61-67, 1989.

Although *Escherichia coli* has a gcd gene and produces a GCD apoenzyme, it is not able to produce PQQ. Therefore, it does not have the GCD activity unless PQQ is added. However, it is known that if a certain foreign gene is expressed, a substance that substitutes for PQQ can be generated, and the GCD activity is expressed (WO2006/133898). A bacterium that does not usually have the GCD activity, but can express the GCD activity as described above, such as *Escherichia* bacteria, is an example of the "enterobacterium inherently having the GCD activity" referred to in the presently disclosed subject matter. The GCD activity will be explained later.

Hereafter, methods for imparting an L-amino acid-producing ability to such bacteria as described above, or methods for enhancing an L-amino acid-producing ability of such bacteria are described.

To impart the ability to produce an L-amino acid, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include acquisition of an auxotrophic mutant, an L-amino acid analogue-resistant strain, or a metabolic regulation mutant, construction of a recombinant strain in which expression of an L-amino acid biosynthesis is enhanced, and so forth. Here, in the breeding of L-amino acid-producing bacteria, one or more properties such as an auxotrophic mutation, analogue resistance, or metabolic regulation mutation can be imparted. The expression of L-amino acid biosynthesis enzyme(s) can be enhanced alone or in combinations of two or more. Furthermore, the methods of imparting properties such as an auxotrophic mutation, analogue resistance, or metabolic regulation mutation can be combined with the methods of enhancing the biosynthesis enzymes.

An auxotrophic mutant strain, L-amino acid analogue-resistant strain, or metabolic regulation mutant strain with an ability to produce an L-amino acid can be obtained by subjecting a parent strain or wild-type strain to conventional mutatagenesis, such as exposure to X-rays or UV irradiation, or treatment with a mutagen such as N-methyl-N'-nitro-N-nitrosoguanidine, etc., and then selecting those which exhibit autotrophy, analogue resistance, or a metabolic regulation mutation and which also have an ability to produce an L-amino acid.

Moreover, imparting or enhancing the ability to produce an L-amino acid can also be attained by enhancing an enzymatic activity by gene recombination. An example of a method for enhancing an enzymatic activity includes, for example, a method of modifying a bacterium so that expression of a gene encoding an enzyme involved in biosynthesis of an L-amino acid is enhanced. As for the method for enhancing expression of a gene, enhancement can also be attained by introducing an amplification plasmid prepared by introducing a DNA fragment containing the gene into an appropriate plasmid, for example, a plasmid vector containing at least the gene responsible for replication and proliferation of the plasmid in a microorganism, increasing the copy number of the gene on the chromosome by conjugation, transfer or the like, or introducing a mutation into a promoter region of the gene (refer to International Patent Publication WO95/34672).

When an objective gene is introduced into the aforementioned amplification plasmid or chromosome, any promoter can be used to express the gene so long as it functions in the objective bacteria. The promoter can be the promoter of the gene to be used itself, or a modified promoter. The expression of the gene can also be controlled by suitably choosing a promoter that is potent in Enterobacteriaceae bacterium, or by making the −35 and −10 regions of the promoter closer to a consensus sequence. Such methods of enhancing expression of a gene of enzyme as described above are described in International Patent Publication WO00/18935, European Patent Laid-open No. 1010755, and so forth.

Hereafter, specific methods for imparting an L-amino acid-producing ability to bacteria and bacteria imparted with L-amino acid-producing ability are exemplified below. Although the following descriptions mainly relate to *Escherichia* bacteria, the following methods can also be applied to enterobacteria of the presently disclosed subject matter.

L-Threonine-Producing Bacteria

Examples of microorganisms having L-threonine-producing ability include bacteria in which one or more activities of L-threonine biosynthesis system enzymes are enhanced. Examples of L-threonine biosynthetic enzymes include aspartokinase III (lysC), aspartate semialdehyde dehydrogenase (asd), aspartokinase I (thrA), homoserine kinase (thrB), threonine synthase (thrC) encoded by thr operon, and aspartate aminotransferase (aspartate transaminase) (aspC). The names of the genes coding for the respective enzymes are mentioned in the parentheses after the names of the enzymes (the same shall apply throughout this specification). Among these enzymes, aspartate semialdehyde dehydrogenase, aspartokinase I, homoserine kinase, aspartate aminotransferase, and threonine synthase are particular examples. The genes coding for the L-threonine biosynthetic enzymes can be introduced into a bacterium having a reduced ability to decompose threonine. An example of such an *Escherichia* bacterium having a reduced ability to decompose threonine is the TDH6 strain which is deficient in threonine dehydrogenase activity (Japanese Patent Laid-open No. 2001-346578).

The enzymatic activities of the L-threonine biosynthetic enzymes are inhibited by the end product, L-threonine. Therefore, for constructing L-threonine-producing strains, it is desirable that the genes for the L-threonine biosynthetic enzymes are modified so that the enzymes are desensitized to feedback inhibition by L-threonine in the L-threonine-producing strains. The aforementioned thrA, thrB, and thrC genes constitute the threonine operon, which forms an attenuator structure. The expression of the threonine operon is inhibited by isoleucine and threonine in the culture medium and also suppressed by attenuation. Therefore, the threonine operon can be modified by removing the leader sequence in the attenuation region or the attenuator (refer to Lynn, S. P., Burton, W. S., Donohue, T. J., Gould, R. M., Gumport, R. L., and Gardner, J. F., J. Mol. Biol. 194:59-69 (1987); WO02/26993; WO2005/049808).

The native promoter of the threonine operon is present upstream of the threonine operon, and can be replaced with a non-native promoter (refer to WO98/04715), or a threonine operon having been modified so that expression of the threonine biosynthesis gene is controlled by the repressor and promoter of λ-phage can be constructed (European Patent No. 0593792). Furthermore, in order to modify a bacterium so that it is desensitized to feedback inhibition by L-threonine, a strain resistant to α-amino-β-hydroxyisovaleric acid (AHV) can be selected.

The copy number of the threonine operon that is modified to desensitize to feedback inhibition by L-threonine can be increased, or the expression of the threonine operon can be increased by ligating it to a potent promoter in a host. The copy number can also be increased by, besides amplification using a plasmid, transferring the threonine operon to a genome using a transposon, Mu-phage, or the like.

Other than increasing expression of the L-threonine biosynthetic genes, expression of the genes involved in the glycolytic pathway, TCA cycle, or respiratory chain, the genes that regulate the expression of these genes, or the genes involved in sugar uptake can also be increased. Examples of such genes include the genes encoding transhydrogenase (pntAB, European Patent No. 733712), phosphoenolpyruvate carboxylase (pepC, WO95/06114), phosphoenolpyruvate synthase (pps, European Patent No. 877090), and a gene encoding pyruvate carboxylase from coryneform bacterium or Bacillus bacterium (WO99/18228, European Patent Laid-open No. 1092776 A).

Resistance to L-threonine, L-homoserine, or both can be imparted to the host by, for example, enhancing expression of a gene that imparts resistance to L-threonine or L-homoserine. Examples of these genes include rhtA gene (Livshits, V. A. et al., 2003, Res. Microbiol., 154:123-135), rhtB (European Patent Laid-open No. 0994190), rhtC gene (European Patent Laid-open No. 1013765), yfiK, and yeaS genes (European Patent Laid-open No. 1016710). The methods for imparting L-threonine resistance to a host are described in European Patent Laid-open No. 0994190 and WO90/04636.

Examples of L-threonine-producing bacteria and parent strains which can be used to derive such bacteria include, but are not limited to, strains belonging to the genus Escherichia, such as E. coli TDH-6/pVIC40 (VKPM B-3996) (U.S. Pat. No. 5,175,107, U.S. Pat. No. 5,705,371), E. coli 472T23/pYN7 (ATCC 98081) (U.S. Pat. No. 5,631,157), E. coli NRRL-21593 (U.S. Pat. No. 5,939,307), E. coli FERM BP-3756 (U.S. Pat. No. 5,474,918), E. coli FERM BP-3519 and FERM BP-3520 (U.S. Pat. No. 5,376,538), E. coli MG442 (Gusyatiner et al., Genetika (in Russian), 14, 947-956 (1978)), E. coli VL643 and VL2055 (European Patent Laid-open No. 1149911) and so forth.

The TDH-6 strain is deficient in the thrC gene, as well as being sucrose-assimilative, and the ilvA gene thereof has a leaky mutation. This strain also has a mutation in the rhtA gene, which imparts resistance to high concentration of threonine or homoserine. The B-3996 strain contains the plasmid pVIC40, which was obtained by inserting the thrA*BC operon, including a mutant thrA gene, into the RSF1010-derived vector. This mutant thrA gene encodes aspartokinase homoserine dehydrogenase I which is substantially desensitized to feedback inhibition by threonine. The B-3996 strain was deposited on Nov. 19, 1987 in the All-Union Scientific Center of Antibiotics (Nagatinskaya Street 3-A, 117105 Moscow, Russia) under the accession number RIA 1867. The strain was also deposited at the Russian National Collection of Industrial Microorganisms (VKPM) (1 Dorozhny proezd., 1 Moscow 117545, Russia) on Apr. 7, 1987 under the accession number VKPM B-3996.

E. coli VKPM B-5318 (European Patent No. 0593792) can also be used as an L-threonine-producing bacterium or a parent strain for deriving it. The B-5318 strain is prototrophic with regard to isoleucine, and a temperature-sensitive lambda-phage C1 repressor and PR promoter replace the regulatory region of the threonine operon in the plasmid pVIC40. The VKPM B-5318 strain was deposited as an international deposit at the Russian National Collection of Industrial Microorganisms (VKPM) (1 Dorozhny proezd., 1 Moscow 117545, Russia) on May 3, 1990 under the accession number of VKPM B-5318.

The thrA gene which encodes aspartokinase homoserine dehydrogenase I of Escherichia coli has been elucidated (nucleotide positions 337 to 2799, GenBank accession NC_000913.2, gi: 49175990). The thrA gene is located between the thrL and thrB genes on the chromosome of E. coli K-12. The thrB gene which encodes homoserine kinase of Escherichia coli has been elucidated (nucleotide positions 2801 to 3733, GenBank accession NC_000913.2, gi: 49175990). The thrB gene is located between the thrA and thrC genes on the chromosome of E. coli K-12. The thrC gene which encodes threonine synthase of Escherichia coli has been elucidated (nucleotide positions 3734 to 5020, GenBank accession NC_000913.2, gi: 49175990). The thrC gene is located between the thrB gene and the yaaX open reading frame on the chromosome of E. coli K-12. All three genes function as a single threonine operon. To enhance expression of the threonine operon, the attenuator region which affects the transcription can be removed from the operon (WO2005/049808, WO2003/097839).

A mutant thrA gene which encodes aspartokinase homoserine dehydrogenase I resistant to feedback inhibition by threonine, as well as the thrB and thrC genes can be obtained as one operon from the well-known plasmid pVIC40 which is present in the threonine-producing E. coli strain VKPM B-3996. The plasmid pVIC40 is described in detail in U.S. Pat. No. 5,705,371.

The rhtA gene is present at 18 min on the E. coli chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, European Patent Laid-open No. 1013765).

The asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC_000913.1, gi:16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

Examples of L-lysine-producing bacteria and parent strains which can be used to derive L-lysine-producing bacteria also include strains in which expression of one or more genes encoding an L-lysine biosynthetic enzyme are enhanced. Examples of such enzymes include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), diaminopimelate epimerase (dapF), tetrahydrodipicolinate succinylase (dapD), succinyl diaminopimelate deacylase (dapE), and aspartase (aspA) (European Patent Laid-open No. 1253195). Among these enzymes, dihydrodipicolinate reductase, diaminopimelate decarboxylase, diaminopimelate dehydrogenase, phosphoenolpyrvate carboxylase, aspartate aminotransferase, diaminopimelate epimerase, aspartate semialdehyde dehydrogenease, tetrahydrodipicolinate succinylase, and succinyl diaminopimelate deacylase can be used in another embodiment. In addition, the parent strains can express increased levels of the gene involved in energy efficiency (cyo) (European Patent Laid-open No. 1170376), the gene encoding nicotinamide nucleotide transhydrogenase (pntAB) (U.S. Pat. No. 5,830,716), the ybjE gene (WO2005/073390), or combinations thereof.

Examples of parent strains which can be used to derive L-lysine-producing bacteria also include strains having decreased or eliminated activity of an enzyme that catalyzes a reaction for generating a compound other than L-lysine by branching off from the biosynthetic pathway of L-lysine. Examples of these enzymes include homoserine dehydrogenase, lysine decarboxylase (U.S. Pat. No. 5,827,698), and the malic enzyme (WO2005/010175).

Examples of L-lysine-producing bacteria include *Escherichia coli* WC196ΔcadAΔ1dc/pCABD2 (WO2006/078039). The strain was constructed by introducing the plasmid pCABD2 described in U.S. Pat. No. 6,040,160 into the WC196 strain having disrupted cadA and ldcC genes, which encode lysine decarboxylase. The WC196 strain was bred from the W3110 strain, which was derived from *Escherichia coli* K-12, by replacing the wild type lysC gene on the chromosome of the W3110 strain with a mutant lysC gene encoding a mutant aspartokinase III in which threonine at position 352 was replaced with isoleucine, resulting in desensitization of the feedback inhibition thereof by L-lysine (U.S. Pat. No. 5,661,012), and conferring AEC resistance to the resulting strain (U.S. Pat. No. 5,827,698). The WC196 strain was designated *Escherichia coli* AJ13069, deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698). The WC196ΔcadAΔ1dc strain itself can be L-lysine-producing bacterium. The plasmid pCABD2 contains a mutant dapA gene derived from *Escherichia coli* and coding for a dihydrodipicolinate synthase (DDPS) having a mutation for desensitization to the feedback inhibition by L-lysine, a mutant lysC gene derived from *Escherichia coli* and coding for aspartokinase III having a mutation for desensitization to the feedback inhibition by L-lysine, the dapB gene derived from *Escherichia coli* and coding for dihydrodipicolinate reductase, and the ddh gene derived from *Brevibacterium lactofermentum* and coding for diaminopimelate dehydrogenase (International Publications WO95/16042 and WO01/53459).

L-Cysteine-Producing Bacteria

L-Cysteine-producing ability of a bacterium can be improved by enhancing activity of an enzyme of the L-cysteine biosynthesis pathway or an enzyme involved in production of a compound serving as a substrate of that pathway such as L-serine, for example, 3-phosphoglycerate dehydrogenase, serine acetyltransferase, and so forth. 3-Phosphoglycerate dehydrogenase is subject to feedback inhibition by serine, and therefore the activity of this enzyme can be enhanced by incorporating a mutant serA gene coding for a mutant 3-phosphoglycerate dehydrogenase for which the feedback inhibition is attenuated or eliminated into a bacterium.

Furthermore, serine acetyltransferase is subject to feedback inhibition by L-cysteine. Therefore, the activity of this enzyme can be enhanced by incorporating a mutant cysE gene coding for a mutant serine acetyltransferase for which the feedback inhibition is attenuated or eliminated into a bacterium. As the gene coding for SAT of *Escherichia coli*, cycE has been cloned from a wild-type strain and an L-cysteine excretion mutant strain, and the nucleotide sequence thereof has been elucidated (Denk, D. and Boeck, A., J. General Microbiol., 133, 515-525 (1987)). The nucleotide sequence and the amino acid sequence encoded by the nucleotide sequence are shown in SEQ ID NOS: 37 and 38.

The L-cysteine-producing ability can also be improved by enhancing the activity of the sulfate/thiosulfate transport system. The sulfate/thiosulfate transport system protein group is encoded by the cysPTWAM gene cluster (Japanese Patent Laid-open No. 2005-137369, European Patent No. 1528108).

The L-cysteine-producing ability of a bacterium can also be improved by increasing expression of the yeaS gene (European Patent Laid-open No. 1016710). The nucleotide sequence of the yeaS gene and the amino acid sequence encoded by the gene are shown in SEQ ID NOS: 39 and 40, respectively. It is known that bacteria use various codons such as GTG besides ATG as the start codon (depts.washington.edu/agro/genomes/students/stanstart.htm). Although the amino acid corresponding to the initial codon gtg is indicated as Val in SEQ ID NOS: 39 and 40, it is highly possible that it is actually Met.

Specific examples of *Escherichia* bacteria having L-cysteine-producing ability and parent strains which can be used to derive such bacteria include, but not limited to, *Escherichia* bacteria such as *E. coli* JM15 transformed with different cysE gene alleles encoding serine acetyltransferase resistant to feedback inhibition (U.S. Pat. No. 6,218,168, Russian Patent Application No. 2003121601), *E. coli* W3110 in which a gene encoding a protein responsible for excretion of cytotoxic substances is overexpressed (U.S. Pat. No. 5,972,663), *E. coli* strain having decreased cysteine desulfhydrase activity (Japanese Patent Laid-open No. 11-155571), and *E. coli* W3110 in which activity of the positive transcriptional control factor of the cysteine regulon encoded by the cysB gene is increased (WO01/27307).

L-Cysteine-producing ability of a bacterium can be improved by modifying the bacterium so that the activity of the protein encoded by yhaM (henceforth also referred to as "YhaM") is decreased. The yhaM gene is the same as ECK3099, b4470 and yhaN genes, and it was also called b3109 or b3108 in the past.

Examples of *Pantoea* bacteria having L-cysteine-producing ability include a *Pantoea ananatis* strain modified so that the cysteine desulfhydrase activity is reduced, and a *Pantoea ananatis* strain having a gene encoding a mutant serine acetyltransferase for which the feedback inhibition by L-cysteine is reduced. Examples of parent strains for breeding such L-cysteine-producing bacteria include the *Pantoea ananatis* AJ13355 strain, SC17 strain, and SC17(0) strain. The AJ13355 strain is a strain isolated from soil in Iwata-shi, Shizuoka-ken, Japan as a strain that can proliferate in a low pH medium containing L-glutamic acid and a carbon source, and the SC17 strain is a strain selected as a low phlegm-producing mutant strain from the AJ13355 strain (U.S. Pat. No. 6,596,517). The *Pantoea ananatis* AJ13355 strain was deposited at the National Institute of Bioscience and Human-Technology, Agency of Industrial Science and Technology, Ministry of International Trade and Industry (currently, the National Institute of Advanced Industrial Science and Technology, International Patent Organism Depositary, Address: Tsukuba Central 6, 1-1, Higashi 1-Chome, Tsukuba-shi, Ibaraki-ken, 305-8566, Japan) on Feb. 19, 1998 and assigned an accession number of FERM P-16644. It was then converted to an international deposit under the provisions of Budapest Treaty on Jan. 11, 1999 and assigned an accession number of FERM BP-6614. The SC17(0) strain is a strain constructed as a strain resistant to the λ Red gene product for performing gene disruption in *Pantoea ananatis* (refer to Reference Example 1).

The SC17 strain was given a private number of AJ416, and deposited at the National Institute of Advanced Industrial Science and Technology, International Patent Organism Depositary (address: Tsukuba Central 6, 1-1, Higashi 1-Chome, Tsukuba-shi, Ibaraki-ken, 305-8566, Japan) on Feb. 4, 2009 as an international deposit, and assigned an accession number of FERM BP-11091. The SC17(0) strain was deposited at the Russian National Collection of Industrial Microorganisms (VKPM), GNII Genetika (address: Russia, 117545 Moscow, 1 Dorozhny proezd. 1) on Sep. 21, 2005 with an accession number of VKPM B-9246.

A part of L-cysteine produced by a bacterium can change into L-cystine in a medium by formation of disulfide bond. Furthermore, as described later, S-sulfocysteine can be generated by the reaction of L-cysteine and thiosulfuric acid contained in the medium (Szczepkowski T. W., Nature, vol. 182 (1958)). Furthermore, L-cysteine generated in bacterial cells can be condensed with a ketone, aldehyde, or, for example, pyruvic acid, which exists in the cells, to produce a thiazolidine derivative via a hemithioketal as an intermediate (refer to Japanese Patent No. 2992010). These thiazolidine derivative and hemithioketal can exist as an equilibrated mixture. Therefore, the L-cysteine-producing ability is not limited to ability to accumulate only L-cysteine in a medium or cells, but also includes an ability to accumulate, in addition to L-cysteine, L-cystine or a derivative thereof such as S-sulfocysteine, a thiazolidine derivative, or a hemithioketal or a mixture thereof in the medium.

L-Leucine-Producing Bacteria

Examples of L-leucine-producing bacteria and parent strains which can be used to derive L-leucine-producing bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (Japanese Patent Publication No. 62-34397 and Japanese Patent Laid-open No. 8-70879); *E. coli* strains obtained by the gene engineering method described in WO96/06926; *E. coli* H-9068 (Japanese Patent Laid-open No. 8-70879), and so forth.

The bacterium of the presently disclosed subject matter can be improved by enhancing expression of one or more genes involved in L-leucine biosynthesis. Examples of such genes include the genes of the leuABCD operon, a typical example of which is a mutant leuA gene encoding isopropyl malate synthase desensitized to feedback inhibition by L-leucine (U.S. Pat. No. 6,403,342). In addition, the bacterium of the presently disclosed subject matter can be improved by enhancing expression of one or more genes encoding proteins which excrete L-amino acid from the bacterial cell. Examples of such genes include the b2682 and b2683 genes (ygaZH genes) (European Patent Laid-open No. 1239041 A2).

L-Histidine-Producing Bacteria

Examples of L-histidine-producing bacteria and parent strains which can be used to derive L-histidine-producing bacteria include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (European Patent No. 1085087); *E. coli* AI80/pFM201 (U.S. Pat. No. 6,258,554) and so forth.

Examples of L-histidine-producing bacteria and parent strains which can be used to derive L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase gene (hisG) (Russian Patent Nos. 2003677 and 2119536).

Specific examples of strains having an L-histidine-producing ability include E. coli FERM P-5038 and 5048 which have been introduced with a vector carrying a DNA encoding an L-histidine-biosynthetic enzyme (Japanese Patent Laid-open No. 56-005099), E. coli strains introduced with rht, a gene for an amino acid-export (European Patent Laid-open No. 1016710), E. coli 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of L-glutamic acid-producing bacteria and parent strains which can be used to derive L-glutamic acid-producing bacteria include, but are not limited to, strains belonging to the genus *Escherichia*, such as *E. coli* VL334thrC$^+$ (European Patent No. 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC$^+$ (VKPM B-8961) was obtained.

Examples of L-glutamic acid-producing bacteria and parent strains which can be used to derive L-glutamic acid-producing bacteria also include, but are not limited to, strains in which activity of one or more of an L-glutamic acid biosynthetic enzyme is enhanced. Examples of such genes include the genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), methyl citrate synthase (prpC), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), and so forth. Among these enzymes, glutamate dehydrogenase, citrate synthase, phosphoenolpyruvate carboxylase, and methyl citrate synthase can be used in another embodiment.

Examples of strains which have been modified so that expression of the citrate synthetase gene, the phosphoenolpyruvate carboxylase gene, and/or the glutamate dehydrogenase gene is enhanced include those disclosed in European Patent Laid-open Nos. 1078989, 955368, and 952221.

L-Glutamic acid-synthesizing ability of a bacterium can be improved by enhancing activity of an enzyme involved in the respiratory chain, for example, a cyan-resistant respiration terminal oxidizing enzyme (cioA, cioB).

Examples of L-glutamic acid-producing bacteria and parent strains which can be used to derive L-glutamic acid-producing bacteria also include strains in which activity of an enzyme that catalyzes synthesis of a compound other than L-glutamic acid by directing synthesis away from the biosynthetic pathway of L-glutamic acid, or activity of an enzyme that catalyzes a reaction of decomposing or consuming L-glutamic acid, is reduced or eliminated. Examples of these enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), γ-glutamyl transferase (ggt), γ-glutamylcysteine synthetase (gshA), γ-glutamylputrescine synthetase (ycjK), and so forth. *Escherichia* bacteria without α-ketoglutarate dehydrogenase activity or with reduced α-ketoglutarate dehydrogenase activity and methods to obtain such bacteria are described in U.S. Pat. Nos. 5,378,616 and 5,573,945.

Specifically, these strains include the following:
E. coli W3110sucA::Km$^r$
E. coli AJ12624 (FERM BP-3853)
E. coli AJ12628 (FERM BP-3854)
E. coli AJ12949 (FERM BP-4881)

E. coli W3110sucA::Km$^r$ is obtained by disrupting the α-ketoglutarate dehydrogenase gene (hereinafter also referred to as the "sucA gene") of *E. coli* W3110. This strain is completely deficient in α-ketoglutarate dehydrogenase.

Other examples of L-glutamic acid-producing bacterium include *Escherichia* bacteria which are resistant to an aspartic acid antimetabolite. These strains can also be deficient in α-ketoglutarate dehydrogenase and include, for example, *E. coli* AJ13199 (FERM BP-5807) (U.S. Pat. No. 5,908,768), FFRM P-12379, which additionally is decreased in an activity to decompose L-glutamic acid (U.S. Pat. No. 5,393,671); AJ13138 (FERM BP-5565) (U.S. Pat. No. 6,110,714), and so forth.

Examples of L-glutamic acid-producing bacterium of *Pantoea ananatis* include the *Pantoea ananatis* AJ13355 strain described above.

Furthermore, examples of an L-glutamic acid-producing bacterium of *Pantoea ananatis* also include *Pantoea* bacteria deficient in α-ketoglutarate dehydrogenase (αKGDH) activity or having reduced αKGDH activity. Examples of such a strain include AJ13356 (U.S. Pat. No. 6,331,419), which was derived by deleting the αKGDH-E1 subunit gene (sucA) in AJ13355, and the SC17sucA strain (U.S. Pat. No. 6,596,517) which also does not have the sucA gene, and was selected from AJ13355 for its low phlegm production properties. The AJ13356 strain was deposited at the National Institute of Bioscience and Human-Technology, Agency of Industrial Science and Technology (currently, the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566)) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. Although the AJ13355 and AJ13356 strains were deposited at the aforementioned depository as *Enterobacter agglomerans*, they are referred to as *Pantoea ananatis* in this specification. The SC17sucA strain was assigned the private number of AJ417, and deposited at the National Institute of Advanced Industrial Science and Technology, International Patent Organism Depositary on Feb. 26, 2004, under an accession number of FERM BP-08646.

Examples of L-glutamic acid-producing *Pantoea ananatis* bacteria further include SC17sucA/RSFCPG+pSTVCB, AJ13601, NP106, and NA1 strains. The SC17sucA/RS-FCPG+pSTVCB strain was obtained by introducing the plasmid RSFCPG containing the citrate synthase gene (gltA), phosphoenolpyruvate carboxylase gene (ppsA), and glutamate dehydrogenase gene (gdhA) derived from *Escherichia coli*, and the plasmid pSTVCB containing the citrate synthase gene (gltA) derived from *Brevibacterium lactofermentum*, into the SC17sucA strain. The AJ13601 strain was selected from the SC17sucA/RSFCPG+pSTVCB strain for its resistance to high concentration of L-glutamic acid at a low pH. Furthermore, the NP106 strain was derived from the AJ13601 strain by eliminating the RSFCPG+pSTVCB plasmid. The AJ13601 strain was deposited at the National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Aug. 18, 1999, and assigned accession number FERM P-17516. Then, the deposit was converted into an international deposit under the provisions of the Budapest Treaty on Jul. 6, 2000, and assigned an accession number FERM BP-7207. Moreover, the NP106 strain having RSF-PPG in which the gltA gene of RSFCPG described above is replaced with prpC (refer to WO2008/020654, the examples mentioned later) can be used as an L-glutamic acid-producing bacterium.

L-Phenylalanine-Producing Bacteria

Examples of L-phenylalanine-producing bacteria and parent strains which can be used to derive L-phenylalanine-producing bacteria include, but are not limited to, *Escherichia* bacterial strains, such as *E. coli* AJ12739 (tyrA::Tn10, tyrR) (VKPM B-8197) which lacks chorismate mutase-prephenate dehydrogenase and the tyrosine repressor (WO03/044191), *E. coli* HW1089 (ATCC 55371) which contains a mutant type pheA34 gene coding for chorismate mutase-prephenate dehydratase having been mutated to be desensitized to feedback inhibition (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407,952). Also, the following strains can be used to derive L-phenylalanine-producing bacteria: *E. coli* K-12 [W3110(tyrA)/pPHAB (FERM BP-3566) which contains genes coding for chorismate mutase-prephenate dehydratase having been mutated to be desensitized to feedback inhibition, *E. coli* K-12 [W3110(tyrA)/pPHAD] (FERM BP-12659), *E. coli* K-12 [W3110(tyrA)/pPHATerm] (FERM BP-12662), and *E. coli* K-12 [W3110(tyrA)/pBR-aroG4, pACMAB] (also known as AJ12604 (FERM BP-3579) (European Patent No. 488424 B1). Furthermore, *Escherichia* L-phenylalanine-producing bacteria with enhanced activity of the protein encoded by the yedA gene or the yddG gene can also be used (U.S. Patent Published Applications Nos. 2003/0148473 and 2003/0157667, WO03/044192).

L-Tryptophan-Producing Bacteria

Examples of L-tryptophan-producing bacteria and parent strains which can be used to derive L-tryptophan-producing bacteria include, but are not limited to, *Escherichia* bacterial strains, such as *E. coli* JP4735/pMU3028 (DSM10122) and *E. coli* JP6015/pMU91 (DSM10123) which lack tryptophanyl-tRNA synthetase encoded by a mutant trpS gene (U.S. Pat. No. 5,756,345), *E. coli* SV164 (pGH5) which contains the serA allele encoding phosphoglycerate dehydrogenase and the trpE allele encoding anthranilate synthase, which are desensitized to feedback inhibition by serine and tryptophan, respectively (U.S. Pat. No. 6,180,373), *E. coli* AGX17 (pGX44) (NRRL B-12263), and *E. coli* AGX6(pGX50)aroP (NRRL B-12264) which lack tryptophanase (U.S. Pat. No. 4,371,614), and *E. coli* AGX17/pGX50, pACKG4-pps in which phosphoenolpyruvate-producing ability is enhanced (WO97/08333, U.S. Pat. No. 6,319,696). L-Tryptophan-producing bacteria belonging to the genus *Escherichia* with enhanced activity of the protein encoded by the yedA gene or the yddG gene can also be used (U.S. Patent Published Application Nos. 2003/0148473 and 2003/0157667).

Examples of L-tryptophan-producing bacteria and parent strains which can be used to derive L-tryptophan-producing bacteria also include strains in which one or more activities of the following enzymes are enhanced: anthranilate synthase (trpE), phosphoglycerate dehydrogenase (serA), 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), chorismate synthase (aroC), prephenate dehydratase, chorismate mutase, and tryptophan synthase (trpAB). Prephenate dehydratase and chorismate mutase are encoded by the pheA gene as a bifunctional enzyme (chorismate mutase/prephenate dehydratase, CM/PDH). Among these enzymes, phosphoglycerate dehydrogenase, 3-deoxy-D-arabinoheptulosonate-7-phosphate synthase, 3-dehydroquinate synthase, shikimate dehydratase, shikimate kinase, 5-enolpyruvylshikimate-3-phosphate synthase, chorismate synthase, prephenate dehydratase, and chorismate mutase-prephenate dehydratase can be used in another embodiment. Anthranilate synthase and phosphoglycerate dehydrogenase both suffer from feedback inhibition by L-tryptophan and L-serine, and therefore a mutation desensitizing the feedback inhibition can be introduced into the genes encoding these enzymes. Specific examples of strains having such a mutation include *E. coli* SV164 having a desensitized type anthranilate synthase and a transformant strain obtained by introducing a plasmid pGH5 (WO94/08031) containing a mutant serA gene coding for phosphoglycerate dehydrogenase desensitized to feedback inhibition into *E. coli* SV164.

Examples of L-tryptophan-producing bacteria and parent strains which can be used to derive L-tryptophan-producing bacteria also include strains which have been transformed with the tryptophan operon containing a gene encoding inhibition-desensitized anthranilate synthase (Japanese Patent Laid-open Nos. 57-71397, 62-244382, U.S. Pat. No. 4,371,614). Moreover, L-tryptophan-producing ability can be imparted by enhancing expression of a gene which encodes tryptophan synthase in the tryptophan operon (trpBA). Tryptophan synthase includes both α and β subunits, which are encoded by trpA and trpB, respectively. In addition, L-tryptophan-producing ability can be improved by enhancing expression of the isocitrate lyase-malate synthase operon (WO2005/103275).

L-Proline-Producing Bacteria

Examples of L-proline-producing bacteria and parent strains which can be used to derive L-proline-producing bacteria include, but are not limited to, *Escherichia* bacterial strains, such as *E. coli* 702ilvA (VKPM B-8012) which lacks the ilvA gene and can produce L-proline (European Patent No. 1172433).

The bacterium of the presently disclosed subject matter can be improved by enhancing expression of one or more genes involved in L-proline biosynthesis. Examples of genes used for L-proline-producing bacteria include the proB gene coding for glutamate kinase which is desensitized to feedback inhibition by L-proline (DE Patent 3127361). In addition, the bacterium of the presently disclosed subject matter can be improved by enhancing expression of one or more genes coding for proteins responsible for secretion of L-amino acids from the bacterial cell. Examples of such genes are b2682 and b2683 genes (ygaZH genes) (European Patent Laid-open No. 1239041 A2).

*Escherichia* bacteria which produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15th Miami Winter Symposium, 1983, p. 34), and so forth.

L-Arginine-Producing Bacteria

Examples of L-arginine-producing bacteria and parent strains which can be used to derive L-arginine-producing bacteria include, but are not limited to, *Escherichia* bacterial strains, such as *E. coli* strain 237 (VKPM B-7925) (U.S. Patent Published Application No. 2002/058315 A1) and its derivative strains harboring mutant N-acetylglutamate synthase (Russian Patent Application No. 2001112869), *E. coli* strain 382 (VKPM B-7926) (European Patent Laid-open No. 1170358 A1), and an arginine-producing strain transformed with an argA gene encoding N-acetylglutamate synthetase (European Patent Laid-open No. 1170361 A1).

Examples of L-arginine-producing bacteria and parent strains which can be used to derive L-arginine-producing bacteria also include strains in which the expression of one or more genes encoding an L-arginine biosynthetic enzyme is enhanced. Examples of such genes include the N-acetylglutamyl phosphate reductase gene (argC), ornithine acetyl transferase gene (argJ), N-acetylglutamate kinase gene (argB), acetylornithine transaminase gene (argD), ornithine carbamoyl transferase gene (argF), argininosuccinic acid synthetase gene (argG), argininosuccinic acid lyase gene (argH), and carbamoyl phosphate synthetase gene (carAB).

L-Valine-Producing Bacteria

Examples of L-valine-producing bacteria and parent strains which can be used to derive L-valine-producing bacteria include, but are not limited to, strains which have been modified to overexpress the ilvGMEDA operon (U.S. Pat. No. 5,998,178). It is desirable to remove the region in the ilvGMEDA operon which is required for attenuation so that expression of the operon is not attenuated by the produced L-valine. Furthermore, the ilvA gene in the operon can be disrupted so that threonine deaminase activity is decreased.

Examples of L-valine-producing bacteria and parent strains which can be used to derive L-valine-producing bacteria also include mutants having amino-acyl t-RNA synthetase mutations (U.S. Pat. No. 5,658,766). An example is *E. coli* VL1970, having a mutation in the ileS gene encoding isoleucine tRNA synthetase. *E. coli* VL1970 was deposited at the Russian National Collection of Industrial Microorganisms (VKPM) (1 Dorozhny proezd., 1 Moscow 117545, Russia) on Jun. 24, 1988 under the accession number VKPM B-4411.

Furthermore, mutant strains which require lipoic acid for growth and/or lack $H^+$-ATPase (WO96/06926) are also effective to derive L-valine-producing bacteria.

L-Isoleucine-Producing Bacteria

Examples of L-isoleucine producing bacteria and parent strains which can be used to derive L-isoleucine-producing bacteria include, but are not limited to, mutants which are resistant to 6-dimethylaminopurine (Japanese Patent Laid-open No. 5-304969), mutants which are resistant to isoleucine analogues such as thiaisoleucine and isoleucine hydroxamate, and mutants which are additionally resistant to DL-ethionine and/or arginine hydroxamate (Japanese Patent Laid-open No. 5-130882). In addition, recombinant strains transformed with genes encoding proteins involved in L-isoleucine biosynthesis, such as threonine deaminase and acetohydroxate synthase, are also effective to derive L-isoleucine-producing bacteria (Japanese Patent Laid-open No. 2-458, FR 0356739, and U.S. Pat. No. 5,998,178).

L-Tyrosine-Producing Bacteria

Examples of tyrosine-producing bacteria include *Escherichia* bacteria with a desensitized prephenate dehydratase gene (tyrA) desensitized to the inhibition by tyrosine (European Patent Laid-open No. 1616940).

When the aforementioned L-amino acid-producing bacteria are bred by gene recombination, the genes to be modified or recombined are not limited to genes having the genetic information described above or genes having known sequences, but also include genes having conservative mutations, such as homologues or artificially modified genes, which can also be used so long as the functions of the encoded proteins are not degraded. That is, they can be genes encoding a known amino acid sequence containing one or more substitutions, deletions, insertions, additions or the like of one or several amino acid residues at one or several positions.

Although the number of the "several" amino acid residues referred to herein can differ depending on the position in the three-dimensional structure or the types of amino acid residues of the protein, specifically, it can be 1 to 20, in another example 1 to 10, in another example 1 to 5. The conservative mutation is a mutation wherein substitution takes place mutually among Phe, Trp, and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. The conservative mutation is typically a conservative substitution, and substitutions considered conservative substitutions include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitutions, deletions, insertions, additions, inversions or the like can be a result of a naturally-occurring mutation or a variation due to an individual difference or difference of species of a microorganism from which the genes are derived (mutant or variant). Such genes can be obtained by, for example, modifying a known nucleotide sequence of a gene by site-specific mutagenesis so that the amino acid residues at the specific sites of the encoded protein include substitutions, deletions, insertions, or additions of amino acid residues.

Furthermore, such genes having conservative mutation(s) as described above can encode a protein having a homology of 80% or more, in another exmaple 90% or more, in another example 95% or more, in another example 97% or more, to the entire encoded amino acid sequence and having a function equivalent to that of the wild-type protein. In this specification, the term "homology" can also be used to refer to "identity".

Moreover, codons in the gene sequences can be replaced with other codons which are easily used in the host into which the genes are introduced.

The genes having conservative mutation(s) can be obtained by methods usually used in mutagenesis treatments such as treatments with mutagenesis agents.

Furthermore, the genes can be a DNA which can hybridize with a complementary sequence of a known gene sequence or a probe which can be prepared from the complementary sequence under stringent conditions and encodes a protein having a function equivalent to that of the known gene product. The "stringent conditions" referred to here can be conditions under which a so-called specific hybrid is formed, and a non-specific hybrid is not formed. Examples of the stringent conditions include those under which highly homologous DNAs hybridize to each other, for example, DNAs not less than 80% homologous, in another example not less than 90% homologous, in another example not less than 95% homologous, in another example not less than 97% homologous, hybridize to each other, and DNAs less homologous than the above do not hybridize to each other, or conditions of washing once, for example, 2 or 3 times, at a salt concentration and temperature corresponding to washing typical of Southern hybridization, i.e., 1×SSC, 0.1% SDS at 60° C., in another exmaple 0.1×SSC, 0.1% SDS at 60° C., in another example 0.1×SSC, 0.1% SDS at 68° C.

As the probe, a part of the sequence which is complementary to the gene can also be used. Such a probe can be prepared by PCR using oligonucleotides prepared on the basis of the known gene sequence as primers and a DNA fragment containing the nucleotide sequences as a template. For example, when a DNA fragment having a length of about 300 bp is used as the probe, the washing conditions of hybridization can be 50° C., 2×SSC and 0.1% SDS.

The aforementioned descriptions concerning variants of genes can be similarly applied to the gcd gene described below.

<2-2> Reduction of GCD Activity

Hereafter, modification of a bacterium belonging to the family Enterobacteriaceae to the GCD activity thereof is explained.

The GCD activity means the activity catalyzing the following reaction.

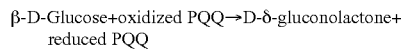
β-D-Glucose+oxidized PQQ→D-δ-gluconolactone+ reduced PQQ

The GCD activity can be measured, for example, on the basis of detection of generation of the reduced DCPIP through the following reactions by spectrometry at 600 nm (Japanese Patent Laid-open No. 2007-129965).

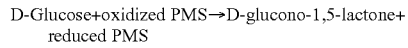
D-Glucose+oxidized PMS→D-glucono-1,5-lactone+ reduced PMS

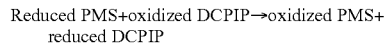
Reduced PMS+oxidized DCPIP→oxidized PMS+ reduced DCPIP

PMS: phenazine methosulfate
DCPIP: 2,6-dichlorophenolindophenol

The phrase "modified so that the GCD activity is reduced" can mean that the GCD activity per cell of the bacterium belonging to the family Enterobacteriaceae is lower than that of a non-modified strain, such as a wild-type strain, of the bacterium. This means, for example, that number of the molecules of GCD per cell is decreased compared with that of the parent strain or a wild-type strain, or that the activity of GCD per molecule is decreased compared with that of the parent strain or a wild-type strain. The GCD activity per cell can be compared by comparing GCD activities in cell extracts of a wild-type strain or parent strain and a modified strain cultured under the same condition. The term "reduction" of the activity includes complete disappearance of the activity. The wild-type Pantoea bacterium used as a reference for the comparison can be, for example, the Pantoea ananatis AJ13355 (FERM BP-6615), or the like.

Reduction of the activity of GCD can be attained by inactivation of the gene encoding GCD (gcd). The "inactivation" of the gcd gene means such modification of the gene by gene recombination or introduction of a mutation into the gene that the activity of GCD encoded by the gene is reduced or eliminated.

Examples of the gcd gene include the gcd gene of Pantoea ananatis having the nucleotide sequence shown in SEQ ID NO: 1. The amino acid sequence of GCD encoded by this gcd gene is shown in SEQ ID NO: 2. The gcd gene can be cloned by performing PCR using oligonucleotides synthesized on the basis of the aforementioned sequence and chromosome of Pantoea ananatis as a template. Moreover, when the gcd gene is deleted by homologous recombination, a gene showing a homology higher than a certain level, for example, 80% or more, in another example 90% or more, in another example 95% or more, to the gcd gene on a chromosome can also be used. Furthermore, a gene hybridizable with the gcd gene on a chromosome under stringent conditions can also be used. Examples of the stringent conditions include, for example, washing once, in another example washing two or three times, at salt concentrations corresponding to 1×SSC, 0.1% SDS, in another example 0.1×SSC, 0.1% SDS, at 60° C.

Specifically, inactivation of the gcd gene can be achieved by, for example, deleting a part or the entire coding region of the gcd gene on a chromosome, or inserting another sequence into the coding region. These techniques are also referred to as gene disruption.

The gcd gene can also be inactivated by decreasing expression of the gcd gene via modification of an expression control sequence such as a promoter or Shine Dargarno (SD) sequence of the gcd gene, or the like. Decrease of expression includes decrease of transcription and decrease of translation. Expression of the gene can also be decreased by modification of a non-translation region other than expression control regions.

Furthermore, the entire target gene, including upstream and downstream regions of the target gene on the chromosome, can be deleted. In addition, inactivation of the gcd gene can also be attained by introduction of a mutation for an amino acid substitution (missense mutation), a stop codon (nonsense mutation), or a frame shift mutation which adds or deletes one or two nucleotides into or from the coding region of the gcd gene on a chromosome (Journal of Biological Chemistry, 272:8611-8617 (1997); Proceedings of the National Academy of Sciences, USA, 95 5511-5515 (1998); Journal of Biological Chemistry, 266, 20833-20839 (1991)).

Modification of the gene can be attained by gene recombination. Specific examples of the method based on gene recombination include deletion of a partial or entire sequence of an expression control sequence of the target gene on a chromosome, for example, a promoter region, or a coding region or a non-coding region, and insertion of another sequence into these regions.

Modification of an expression control sequence can be performed for one or more nucleotides, in another example for two or more nucleotides, in another example three or more nucleotides. When a coding region is deleted, the region to be deleted can be an N-terminal region, an internal region or a C-terminal region, or even the entire coding region, so long as the function of the protein to be produced by the gene is reduced or deleted. Deletion of a longer region can usually more definitively inactivate the target gene. Furthermore, the reading frames upstream and downstream of the region to be deleted are not necessarily the same.

When another sequence is inserted into a coding region, the sequence can be inserted into any region of the target gene, and insertion of a longer region can usually more definitively inactivate the target gene. The reading frames upstream and downstream of the insertion site are not necessarily the same. The other sequence is not particularly limited so long as a sequence which reduces or deletes the function of the protein encoded by the target gene is chosen, and examples include, for example, a transposon carrying an antibiotic resistance gene, a gene useful for L-amino acid production, and so forth.

Such modification of a target gene on a chromosome as described above can be attained by, for example, preparing a deletion-type gene in which a partial sequence of a target gene is deleted so that it cannot produce a protein that can normally function, and transforming a bacterium with a DNA containing the deletion type gene to cause homologous recombination between the deletion type gene and the target gene on a chromosome and thereby substitute the deletion type gene for the target gene on the chromosome. The protein encoded by the deletion type gene has a conformation different from that of a wild-type protein, even if it is produced, and thus the function thereof is reduced or deleted. Such gene disruption based on gene substitution utilizing homologous recombination has been already established, and methods for doing so include the Red driven integration method (Datsenko, K. A, and Wanner, B. L., Proc. Natl. Acad. Sci. USA, 97:6640-6645 (2000)), a method of using a linear DNA such as a method utilizing the Red driven integration in combination with an excisive system derived from λ phage (Cho, E. H., Gumport, R. I., Gardner, J. F., J. Bacteriol., 184:5200-5203 (2002)), a method of using a plasmid containing a temperature sensitive replication origin or a plasmid capable of conjugative transfer, a method of utilizing a suicide vector not having replication origin in a host (U.S. Pat. No. 6,303,383, Japanese Patent Laid-open No. 05-007491), and so forth.

The decrease in transcription of a target gene can be confirmed by comparing the amount of mRNA transcribed from the target gene with that in a wild-type strain or a non-modified strain. Examples of the method for measuring the amount of mRNA include Northern hybridization, RT-PCR, and so forth (Molecular Cloning, Cold spring Harbor Laboratory Press, Cold Spring Harbor (USA), 2001). Although the transcription amount can be decreased to any extent so long as it decreases compared with that observed in a wild-type or non-modified strain, it can be decreased to at least 75% or less, 50% or less, 25% or less, or 10% or less, of that observed in, for example, a wild-type or non-modified strain, and it can be that the gene is not expressed at all.

The decrease in amount of a protein encoded by the target gene can be confirmed by Western blotting using antibodies that bind to the protein (Molecular Cloning, Cold Spring Harbor Laboratory Press, Cold Spring Harbor (USA) 2001). Although the amount of the protein can be decreased to any extent so long as it decreases compared with that observed in a wild-type or non-modified strain, it can be decreased to at least 75% or less, 50% or less, 25% or less, or 10% or less, of that observed in, for example, a wild-type strain or non-modified strain, and it can be that the protein is not produced at all (the activity has completely disappeared).

Examples of the method for decreasing the activity of GCD include, besides the aforementioned genetic manipulation techniques, for example, a method of treating an enterobacterium such as Pantoea bacteria with ultraviolet irradiation or a mutagen used for usual mutagenesis treatment such as N-methyl-N'-nitro-N-nitrosoguanidine (NTG) or nitrous acid, and selecting a strain showing decreased GCD activity.

The activity of GCD can also be reduced by reducing PQQ synthesis ability. The PQQ synthesis ability can be reduced by, for example, deleting a part or all of pqqABCDEF, which is the operon required for PQQ biosynthesis (J. S. Velterop, P. W. Postma, J. Bacteriology 177(17):5088-5098 (1995)).

In the case of a microorganism not having the GCD activity such as Escherichia coli and coryneform bacteria, glucose is taken up by using a transporter called glucose PTS (glucose phosphotransferase system) or glucose permease. PTS is incorporated into cells in the form of glucose 6-phosphate, which couples with the reaction of converting PEP (phosphoenolpyruvic acid) into Pyr (pyruvic acid). Glucose 6-phosphate is converted into fructose-6-phosphate, and metabolized by the so-called glycolytic system (EMP, Embden-Myerhof pathway) to generate pyruvic acid.

On the other hand, in the case of a microorganism having the GCD activity, glucose is first converted into gluconic acid in the periplasmic space, then it is incorporated by gluconate permease, and 6-phosphogluconic acid is generated from it by a phosphorylation reaction.

6-Phosphogluconic acid is metabolized by the pentose phosphate cycle or the Entner-Doudoroff (ED) pathway to generate glyceraldehyde 3-phosphate, pyruvic acid, and so forth.

It is known that a microorganism having GCD such as acetic acid bacteria has a peculiar saccharometabolic characteristic that it first converts a part of glucose into gluconic acid in the periplasm, and then incorporates it. Since capacities of intracellular EMP pathway, ED pathway, and pentose phosphate cycle are different depending on microorganisms, it is expected that if GCD is deleted to modify the saccharometabolism, the downstream metabolic pattern can be changed.

In the case of Pantoea ananatis, it is considered that, at a usual culture temperature, for example, 34° C., glucose is not totally assimilated by GCD, and a considerable amount of it is assimilated by PTS. On the other hand, if it is cultured at a high temperature, for example, 38° C., since the optimum temperature of GCD is high, it is expected that the GCD activity is increased, and saccharide consumption by GCD increases. Since Pantoea ananatis does not have the ED pathway, 6-phosphogluconic acid is dehydrogenated by 6-phosphogluconate dehydrogenase, and then metabolized by the pentose phosphate cycle. Since one molecule of carbon dioxide is released from one molecule of 6-phosphogluconic acid upon the dehydrogenation by 6-phosphogluconate dehydrogenase, it is expected that if saccharide consumption by GCD increases, the amount of amino acids produced decreases. Moreover, it is estimated that if the saccharide consumption by GCD increases due to culture at a high temperature, the capacity of the pentose phosphate cycle becomes insufficient, and overflowing metabolites flow into pathways for generating by-products to decrease L-amino acid yield, as a result. It is considered that the release of carbon dioxide and the overflow of the pentose phosphate cycle are eliminated by the reduction of the GCD activity, especially when the culture is performed at a high temperature, and therefore the L-amino acid productivity is improved.

Furthermore, it is estimated that, also in Pantoea ananatis introduced with the ED pathway (Japanese Patent Laid-open No. 2003-274988), if the saccharide consumption by GCD increases, the L-amino acid yield is decreased due to release of carbon dioxide at the time of the dehydrogenation of 6-phosphogluconic acid by 6-phosphogluconate dehydrogenase, and insufficient capacities of the ED pathway and pentose phosphate cycle. Therefore, the L-amino acid productivity can be improved by reducing the GCD activity also in *Pantoea ananatis* introduced with the ED pathway.

The bacterium of the presently disclosed subject matter can be a bacterium in which GCD activity is reduced and in which activity for incorporating saccharides is further enhanced. The activity for incorporating saccharides can be enhanced by, for example, increasing activity of glucose PTS or glucose permease. Moreover, it is known that transporters considered as members of the major facilitator superfamily (MFS, Griffith, J. K. et al, Cum Opin. Cell Biol., 4(4); 684-95 (1992)) such as galactose permease (Flores et al., J Mol. Microbiol. Biotechnol., 2007; 13:105-116), xylose permease (European Patent Laid-open No. 1807445 A1), and arabinose permease also have the activity for incorporating glucose etc. Therefore, also in a bacterium in which the GCD activity is reduced, by enhancing any of the activities of these transporters, incorporation of saccharides such as glucose is also increased, and the L-amino acid productivity is improved.

<2> Method for Producing L-Amino Acid

By culturing the microorganism of the presently disclosed subject matter in a medium to produce and accumulate an L-amino acid in the medium and collecting the L-amino acid from the medium, an L-amino acid can be produced.

As the medium used for the culture, a typical medium containing a carbon source, nitrogen source, and mineral salts as well as organic trace nutrients such as amino acids and vitamins as required can be used. Either a synthetic medium or a natural medium can be used. Any kind of carbon source and nitrogen source can be used so long as they can be utilized by the chosen strain to be cultured.

Sugars such as glucose, glycerol, fructose, sucrose, maltose, mannose, galactose, starch hydrolysates and molasses can be used as the carbon source. In addition, organic acids such as acetic acid and citric acid, and alcohols such as ethanol can also be used each alone or in combination with other carbon sources. Ammonia, ammonium salts such as ammonium sulfate, ammonium carbonate, ammonium chloride, ammonium phosphate and ammonium acetate, nitric acid salts and so forth can be used as the nitrogen source. Amino acids, vitamins, fatty acids, nucleic acids, those containing those substances such as peptone, casamino acid, yeast extract, soybean protein decomposition product and so forth can be used as the organic trace nutrients. When an auxotrophic mutant strain that requires an amino acid or the like for its growth is used, the required nutrient can be supplemented.

In particular, when a liquid medium prepared so as to satisfy a condition for precipitating L-glutamic acid is used, addition of pantothenic acid to the medium provides more efficient precipitation of L-glutamic acid (WO2004/111258). As inorganic salts, phosphoric acid salts, magnesium salts, calcium salts, iron salts, manganese salt and so forth can be used.

The culture can be performed as an aerobic culture, while the fermentation temperature is controlled to be 20 to 45° C., and pH to be 3 to 9. When the pH decreases during the culture, calcium carbonate can be added, or culture is neutralized with an alkaline substance such as ammonia gas. The target L-amino acid is accumulated in the culture medium after, for example, 10 to 120 hours of culture under such conditions as described above.

Although an L-amino acid can be efficiently produced by culture at a temperature suitable for growth of the bacterium, the effect becomes particularly remarkable especially when the culture is performed at a high temperature. For example, in the case of *Pantoea* bacteria such as *Pantoea ananatis*, a temperature around 34° C. is usually preferred for growth thereof. However, although the bacterium in which GCD activity is reduced shows L-amino acid-producing ability higher than that of a non-modified strain even at such a culture temperature, it shows further improved L-amino acid-producing ability at, for example, 36° C. or 38° C.

Moreover, the culture can be performed by precipitating L-glutamic acid in a medium by using, as the medium, a liquid medium adjusted to satisfy a condition under which L-glutamic acid is precipitated. Examples of the conditions under which L-glutamic acid is precipitated include, for example, pH of 5.0 to 4.0, in another example pH 4.5 to 4.0, in another example pH 4.3 to 4.0, in another example pH 4.0.

When L-glutamic acid is precipitated in the medium, preliminary addition of crystals of L-glutamic acid or L-lysine as seed crystals can provide more efficient crystallization (European Patent No. 1233069, European Patent Laid-open No. 1624069).

Collection of the L-amino acid from the culture broth after the culture can be performed by a known collection method. For example, after the cells were removed from the culture medium, L-amino acid can be collected by concentrating the medium to crystallize the L-amino acid, ion exchange chromatography, or the like. When the culture is performed under conditions so that L-glutamic acid is precipitated, L-glutamic acid which precipitates in the medium can be collected by centrifugation or filtration. In this case, L-glutamic acid which dissolves in the medium can be precipitated and then separated together with already precipitated L-glutamic acid.

When a basic amino acid is produced, a method can be used in which pH of the medium during culture is controlled to be 6.5 to 9.0, and the pH of the medium after completion of the culture is controlled to be 7.2 to 9.0. Furthermore, the pressure in the fermentation tank can be controlled during fermentation to be positive, or carbon dioxide or a mixed gas containing carbon dioxide can be added to the medium so that there is period when bicarbonate ions and/or carbonate ions are present in a concentration of at least 2 g/L in the culture medium during the culture, and these bicarbonate ions and/or carbonate ions serve as counter ions to the cations largely of the basic amino acid, and the target basic amino acid is then collected (refer to Japanese Patent Laid-open No. 2002-065287, U.S. Patent Published Application No. 2002/025564).

The L-amino acid collected can contain bacterial cells, medium components, moisture, and by-product metabolites of the bacterium in addition to the objective L-amino acid. Purity of the collected L-amino acid is 50% or higher, in another example 85% or higher, in another example 95% or higher (Japanese Patent No. 1214636, U.S. Pat. Nos. 5,431,933, 4,956,471, 4,777,051, 4,946,654, 5,840,358, 6,238,714, U.S. Patent Published Application No. 2005/0025878).

When L-cysteine is produced by the method of the presently disclosed subject matter, L-cysteine obtained can be used for production of L-cysteine derivatives. The cysteine derivatives include methylcysteine, ethylcysteine, carbocysteine, sulfocysteine, acetylcysteine, and so forth.

Moreover, when a thiazolidine derivative of L-cysteine is accumulated in the medium, L-cysteine can be produced by collecting the thiazolidine derivative from the medium to break the reaction equilibrium between the thiazolidine derivative and L-cysteine so that L-cysteine is excessively produced. Furthermore, when S-sulfocysteine is accumulated in the medium, it can be converted into L-cysteine by reduction with a reducing agent such as dithiothreitol.

EXAMPLES

Hereafter, the present invention will be explained more specifically with reference to the following non-limiting examples.

Reference Example 1

Construction of a *Pantoea ananatis* Strain which is Resistant to the λ Red Gene Product To delete a gene in *Pantoea ananatis*, a recipient strain was constructed to perform the method called "Red-driven integration" or "Red-mediated integration" (Proc. Natl. Acad. Sci. USA, 97, 6640-6645 (2000)) in a highly efficient manner.

First, the novel helper plasmid RSF-Red-TER which expresses the gam, bet and exo genes of λ (henceforth referred to as "λ Red genes") was constructed (FIG. 1). The details of this construction are described in Reference Example 2.

This plasmid can be used in a wide range of hosts having different genetic backgrounds. This is because 1) this plasmid has the replicon of the RSF1010 wide host spectrum plasmid (Scholz, et al., 1989; Buchanan-Wollaston et al., 1987), which is stably maintained by many types of gram negative and gram positive bacteria, and even plant cells, 2) the λ Red genes, gam, bet and exo genes, are under the control of the P1acUV5 promoter, which is recognized by the RNA polymerases of many types of bacteria (for example, Brunschwig, E. and Darzins, A., Gene, 111, 1, 35-41 (1992); Dehio, M. et al, Gene, 215, 2, 223-229 (1998)), and 3) the autoregulation factor $P_{lacUV5}$-lacI and the ρ-non-dependent transcription terminator (TrrnB) of the rrnB operon of *Escherichia coli* lower the basal expression level of the λ Red genes (Skorokhodova, A. Yu et al, Biotekhnologiya (Rus), 5, 3-21 (2004)). Furthermore, the RSF-Red-TER plasmid contains the levansucrase gene (sacB), and by using this gene, the plasmid can be collected from cells in a medium containing sucrose.

In *Escherichia coli*, the frequency of integration of a PCR-generated DNA fragment along with the short flanking region provided by the RSF-Red-TER plasmid is as high as the frequency obtained when using the pKD46 helper plasmid (Datsenko, K. A., Wanner, B. L., Proc. Natl. Acad. Sci. USA, 97, 6640-6645 (2000)). However, expression of the λ Red genes is toxic to *Pantoea ananatis*. Cells transformed with the RSF-Red-TER helper plasmid grow extremely slowly in LB medium containing IPTG (isopropyl-β-D-thiogalactopyranoside, 1 mM) and an appropriate antibiotic (25 μg/ml of chloramphenicol or 40 μg/ml of kanamycin), and the efficiency of λ Red-mediated recombination is extremely low ($10^{-8}$), if observed at all.

A variant strain of *Pantoea ananatis* which is resistant to expression of all three of the λ Red genes was selected. For this purpose, the RSF-Red-TER plasmid was introduced into the *Pantoea ananatis* SC17 strain (U.S. Pat. No. 6,596,517) by electroporation. After an 18-hour culture, about $10^6$ transformants were obtained, and among these, 10 clones formed colonies of a large size, and all the remainder formed extremely small colonies. After an 18-hour culture, the large colonies were about 2 mm, and the small colonies were about 0.2 mm. Whereas the small colonies did not grow any more even when the culture was extended up to 24 hours, the large colonies continued to grow. One of the large colony *Pantoea ananatis* mutant strains which was resistant to expression of all three of the λ Red genes (gam, bet, and exo) was used for further analysis.

The RSF-Red-TER plasmid DNA was isolated from one clone of the large colony clones, and from several clones of the small colony clones, and transformed again into *Escherichia coli* MG1655 to examine the ability of the plasmid to synthesize an active Red gene product. By a control experiment for Red-dependent integration in the obtained transformants, it was demonstrated that only the plasmid isolated from the large colony clone induced expression of the λ Red genes required for the Red-dependent integration. In order to investigate whether the Red-mediated integration occurs in the selected large colony clone, electroporation was performed using a linear DNA fragment produced by PCR. This fragment was designed so that it contains a $Km^R$ marker and a flanking region of 40 bp homologous to the hisD gene. This fragment is integrated into the hisD gene of *Pantoea ananatis* at the SmaI recognition site. Two small colony clones were used as the control. The nucleotide sequence of the hisD gene of *Pantoea ananatis* is shown in SEQ ID NO: 3. For PCR, the oligonucleotides of SEQ ID NOS: 4 and 5 were used as primers, and the pMW118-(λattL-$Km^r$-λattR) plasmid was used as the template. The two small colony clones which were not resistant to the λ Red genes were used as a control. Construction of the pMW118-(λattL-$Km^r$-λattR) plasmid is explained in detail in Reference Example 3.

The RSF-Red-TER plasmid can induce expression of the Red genes by the lacI gene carried on the plasmid. Two kinds of induction conditions were investigated. In the first group, IPTG (1 mM) was added 1 hour before the electroporation, and in the second group, IPTG was added at the start of the culture to prepare the cells in which electroporation is possible. The growth rate of the cells harboring RSF-Red-TER derived from the large colony clone was not significantly lower than that of a strain not having that plasmid. The addition of IPTG only slightly decreased the growth rate of these cultures. On the other hand, the progeny of the small colony clones grew extremely slowly even without the addition of IPTG, and after induction, growth was substantially arrested. After electroporation of the cells of the progeny of the large colony clone, many $Km^R$ clones grew (18 clones after a short induction time, and about 100 clones after an extended induction time). All of the 100 clones that were investigated had a His⁻ phenotype, and about 20 clones were confirmed by PCR to have the expected structure of the chromosome in the cells. On the other hand, even when electroporation was performed with the progeny of the small colony clones, an integrated strain was not obtained.

The obtained large colony clone was grown on a plate containing 7% sucrose to eliminate the plasmid, and transformed again with RSF-Red-TER. The strain without the plasmid was designated SC17(0).

All the clones which grew after the aforementioned re-transformation showed large colony size like the parent strain clone SC17(0). The Red-mediated integration experiment was performed in the SC17(0) strain re-transformed with the RSF-Red-TER plasmid. Three of the independent transformants were investigated using the same DNA fragment as that used for the previous experiment. The short induction time (1 hour before electroporation) was employed. $Km^R$ clones exceeding ten clones grew in each experiment. All the examined clones had the His phenotype. In this way, a mutant strain designated SC17(0) which is resistant to the expression of the λ Red genes was selected. This strain can be used as a recipient strain suitable for the Red-dependent integration into the *Pantoea ananatis* chromosome.

Reference Example 2

Construction of Helper Plasmid RSF-Red-TER

Figure 2:
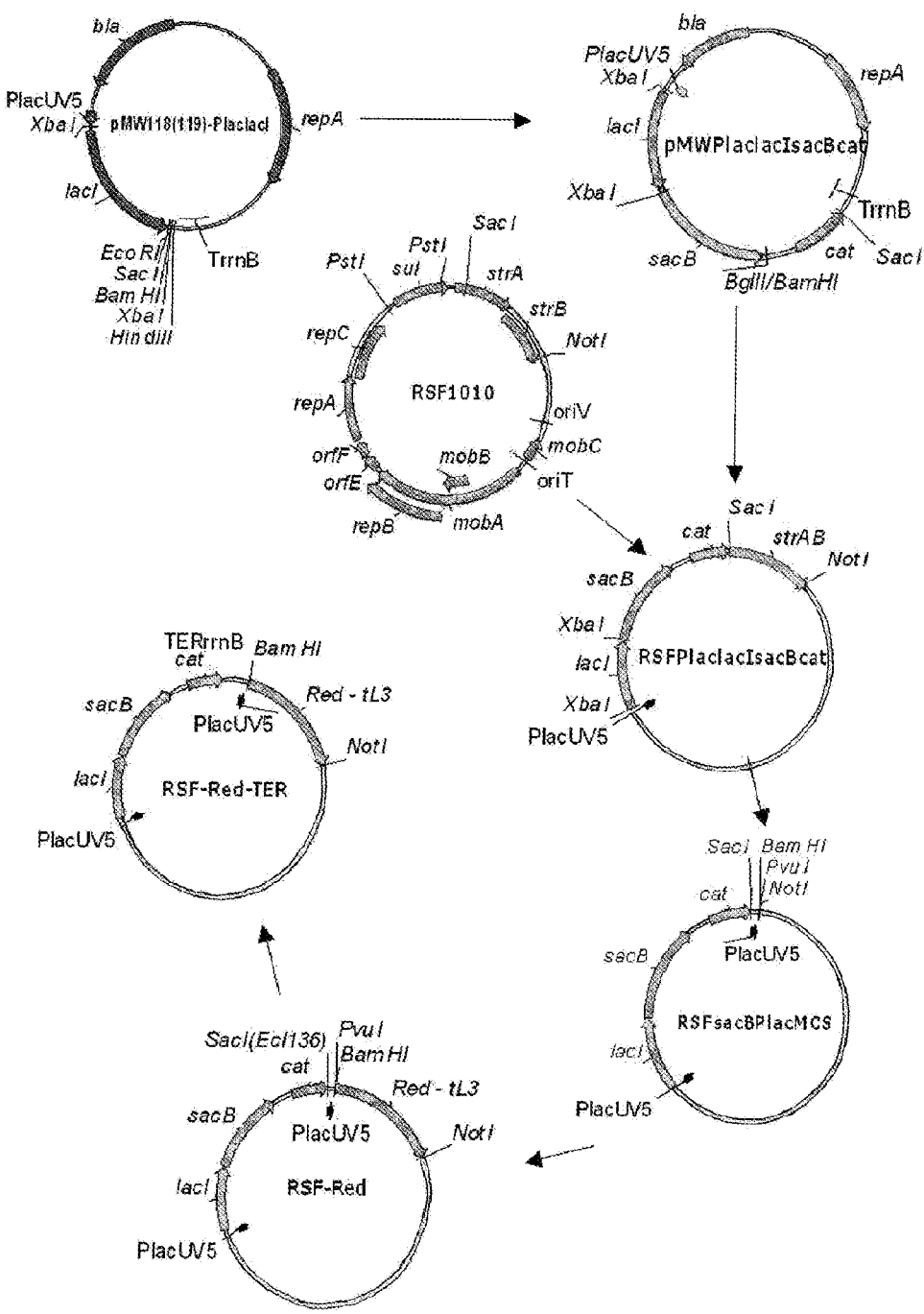
FIG. 2 shows construction of helper plasmid RSF-Red-TER.

The scheme for constructing the helper plasmid RSF-Red-TER is shown in FIG. 2.

As the first step in the construction, an RSFsacBPlacMCS vector was designed. For this purpose, DNA fragments containing the cat gene of the pACYC184 plasmid and the structural region of the sacB gene of *Bacillus subtilis* were amplified by PCR using the oligonucleotides of SEQ ID NOS: 6 and 7, and 8 and 9, respectively. These oligonucleotides contained BglII, SacI, XbaI and BamHI restriction enzyme sites, which are required and convenient for further cloning, in the 5' end regions, respectively. The obtained sacB fragment of 1.5 kb was cloned into the previously obtained pMW119-$P_{lac}$lacI vector at the XbaI-BamHI site. This vector was constructed in the same manner as that described for the pMW118-$P_{lac}$lacI vector (Skorokhodova, A. Yu et al, Biotekhnologiya (Rus), 5, 3-21 (2004)). However, this vector contained a polylinker moiety derived from pMW219 instead of the pMW218 plasmid.

Then, the aforementioned cat fragment of 1.0 kb was treated with BglII and SacI, and cloned into the RSF-$P_{lac}$lacIsacB plasmid obtained in the previous step at the BamHI-SacI site. The obtained plasmid pMW-$P_{lac}$lacIsacBcat contained the PlacUV5-lacI-sacB-cat fragment. In order to subclone this fragment into the RSF1010 vector, pMW-$P_{lac}$lacIsacBcat was digested with BglII, blunt-ended with DNA polymerase I Klenow fragment, and successively digested with SacI. A 3.8 kb BglII-SacI fragment of the pMWP$_{lac}$lacIsacBcat plasmid was eluted from a 1% agarose gel, and ligated with the RSF1010 vector which had been treated with PstI and SacI. *Escherichia coli* TG1 was transformed with the ligation mixture, and plated on the L medium (medium containing 10 g of Bacto tryptone, 5 g of yeast extract, 5 g of NaCl, and 15 g of agar in 1 L of purified water, pH 7.0) containing chloramphenicol (50 mg/L). The plasmids isolated from the grown clones were analyzed with restriction enzymes to obtain an RSFsacB plasmid. In order to construct an RSFsacBP$_{lac}$MCS vector, a DNA fragment containing the P$_{lacUV5}$ promoter was amplified by PCR using the oligonucleotides of SEQ ID NOS: 10 and 11 as primers and the pMW119-P$_{lac}$lacI plasmid as the template. The obtained fragment of 146 bp was digested with SacI and NotI, and ligated with the SacI-NotI large fragment of the RSFsacB plasmid. Then, by PCR using the oligonucleotides of SEQ ID NOS: 12 and 13 as primers, and the pKD46 plasmid (Datsenko, K. A., Wanner, B. L., Proc. Natl. Acad. Sci. USA, 97, 6640-6645 (2000)) as the template, a DNA fragment of 2.3 kb containing the λRedαβγ genes and the transcription terminator tL3 was amplified. The obtained fragment was cloned into the RSFsacBP$_{lac}$MCS vector at the PvuI-NotI site. In this way, the RSFRed plasmid was designed.

In order to eliminate read through transcription of the Red genes, a ρ-dependent transcription terminator of the rrnB operon of *Escherichia coli* was inserted at a position between the cat gene and the P$_{lacUV5}$ promoter. For this purpose, a DNA fragment containing the P$_{lacUV5}$ promoter and the TrrnB terminator was amplified by PCR using the oligonucleotides of SEQ ID NOS: 14 and 11 as primers and the chromosome of *Escherichia coli* BW3350 as the template. These obtained fragments were treated with KpnI and ligated. Then, the 0.5 kb fragment containing both P$_{lacUV5}$ and TrrnB was amplified by PCR using the oligonucleotides of SEQ ID NOS: 11 and 15 as primers. The obtained DNA fragment was digested with EcoRI, blunt-ended by a treatment with DNA polymerase I Klenow fragment, digested with BamHI, and ligated with the Ecl136II-BamHI large fragment of the RSF-sacBPlacMCS vector. The obtained plasmid was designated RSF-Red-TER.

Reference Example 3

Construction of pMW118-(λattL-Km$^r$-λattR) Plasmid

The pMW118-(λattL-Km$^r$-λattR) plasmid was constructed from the pMW118-attL-Tc-attR (WO2005/010175) plasmid by replacing the tetracycline resistance marker gene with the kanamycin resistance gene of the pUC4K plasmid. For that purpose, the EcoRI-HindIII large fragment from pMW118-attL-Tc-attR plasmid was ligated to two fragments from the pUC4K plasmid: HindIII-PstI fragment (676 bp) and EcoRI-HindIII fragment (585 bp). Basic pMW118-attL-Tc-attR was obtained by ligation of the following four fragments.

1) The BglII-EcoRI fragment (114 bp) including attL (SEQ ID NO: 18) which was obtained by PCR amplification of the region corresponding to attL of the *Escherichia coli* W3350 (containing λ prophage) chromosome using the primers P1 and P2 (SEQ ID NOS: 16 and 17) (these primers contained the subsidiary recognition sites for BglII and EcoRI).

2) The PstI-HindIII fragment (182 bp) including attR (SEQ ID NO: 21) which was obtained by PCR amplification of the region corresponding to attR of the *Escherichia coli* W3350 (containing λ prophage) chromosome using the primers P3 and P2 (SEQ ID NOS: 19 and 20) (these primers contained the subsidiary recognition sites for PstI and HindIII).

3) The BglII-HindIII large fragment (3916 bp) of pMW118-ter_rrnB. The plasmid pMW118-ter_rrnB was obtained by ligation of the following three DNA fragments:

The large DNA fragment (2359 bp) including the AatII-EcoRI fragment of pMW118 that was obtained by digesting pMW118 with EcoRI, treating with DNA polymerase I Klenow fragment, and then digesting with AatII;

The small AatII-BglII fragment (1194 bp) of pUC19 including the bla gene for ampicillin resistance (Ap$^R$), which was obtained by PCR amplification of the corresponding region of the pUC19 plasmid using the primers P5 and P6 (SEQ ID NOS: 22 and 23) (these primers contained the subsidiary recognition sites for PstI, AatII and BglII);

The small BglII-PstI fragment (363 bp) of the transcription terminator ter_rrnB, which was obtained by PCR amplification of the corresponding region of the *Escherichia coli* MG1655 chromosome using the primers P7 and P8 (SEQ ID NOS: 24 and 25) (these primers contained the subsidiary recognition sites for PstI, BglII and PstI).

4) The small EcoRI-PstI fragment (1388 bp) (SEQ ID NO: 26) of pML-Tc-ter_thrL including the tetracycline resistance gene and the ter_thrL transcription terminator; the pML-Tc-ter_thrL plasmid was obtained by the following two steps:

the pML-ter_thrL plasmid was obtained by digesting the pML-MCS plasmid (Mashko, S. V. et al., Biotekhnologiya (in Russian), 2001, no. 5, 3-20) with XbaI and BamHI, followed by ligation of the large fragment (3342 bp) with the XbaI-BamHI fragment (68 bp) carrying ter_thrL terminator obtained by PCR amplification of the corresponding region of the *Escherichia coli* MG1655 chromosome using the primers P9 and P10 (SEQ ID NOS: 27 and 28) (these primers contained the subsidiary recognition sites for PstI, XbaI and BamHI);

the pML-Tc-ter_thrL plasmid was obtained by digesting the pML-ter_thrL plasmid with KpnI and XbaI followed by treatment with Klenow fragment of DNA polymerase I and ligated with the small EcoRI-Van91I fragment (1317 bp) of pBR322 including the tetracycline resistance gene (pBR322 was digested with EcoRI and Van91I and then treated with Klenow fragment of DNA polymerase I).

Reference Example 4

Construction of Glutamic Acid-Producing Plasmid RSFPPG

The plasmid RSFPPG (WO2008/020654) was constructed so that the L-glutamic acid biosynthesis system genes, prpC gene (International Patent Publication WO2006/051660), ppc gene and gdhA gene (European Patent Laid-open No. 0999282) were amplified.

The primer 1 (SEQ ID NO: 29) and the primer 2 (SEQ ID NO: 30) for amplifying a part of RSFCPG (European Patent Laid-open No. 1233068) other than the ORF of the gltA gene were designed. By using these primers and RSFCPG as the template, PCR was performed to obtain a fragment of about 14.9 kb. As for prpC, PCR was performed using the primer 3 (SEQ ID NO: 31) and the primer 4 (SEQ ID NO: 32) and the chromosomal DNA of the E. coli W3110 strain as the template to obtain a fragment of about 1.2 kb. Both the PCR products were treated with BglII and KpnI, ligated, and then used to transform the E. coli JM109 strain. All the colonies which grew were collected, and the plasmids were extracted from the colonies as a mixture. The E. coli ME8330 strain, which is a citrate synthase (CS) deficient strain, was transformed with the plasmid mixture, and the cell suspension was applied on M9 minimal medium (5 g of glucose, 2 mM magnesium sulfate, 3 g of monopotassium phosphate, 0.5 g of sodium chloride, 1 g of ammonium chloride and 6 g of disodium phosphate in 1 L of pure water) containing 50 mg/L of uracil and 5 mg/L of thiamine HCl. All the colonies that grew were collected, plasmids were extracted as a mixture, and the NP106 strain, which is an L-glutamic acid-producing strain of P. ananatis, was transformed with the plasmid mixture. The clones that grew were cultured in test tubes under a neutral condition, and a strain showing an L-glutamic acid yield comparative to that of the G106S strain was designated NA1. A plasmid was extracted from this strain and designated RSFPPG for enhancing prpC, gdh, and ppc. This plasmid RSFPPG was introduced into the Pantoea ananatis NP106 strain, which is an L-glutamic acid-producing strain, to construct an L-glutamic acid-producing strain, NP106/RSFPPG (this strain is referred to as "NA1 strain").

The NP106 strain was obtained as follows. The Pantoea ananatis AJ13601 strain described above was cultured overnight at 34° C. in a liquid medium obtained by adding minimal medium components (5 g/L of glucose, 2 mM magnesium sulfate, 3 g/L of monopotassium phosphate, 0.5 g/L of sodium chloride, 1 g/L of ammonium chloride, and 6 g/L of disodium phosphate) to the L medium (10 g/L of Bacto tryptone, 5 g/L of yeast extract, 5 g/L of NaCl, pH 7.0) (henceforth referred to as "LBGM9 medium") with shaking, the medium was diluted so that 100 to 200 colonies will grow per plate, and then the diluted medium was applied to an LBGM9 plate containing 12.5 mg/L of tetracycline. The colonies which appeared were replicated on a LBGM9 plate containing 12.5 mg/L of tetracycline and 25 mg/L of chloramphenicol, and a strain which was sensitive to chloramphenicol was selected to obtain a strain from which pSTVCB was eliminated, which was designated G106S. The G106S strain was further cultured overnight at 34° C. in the LBGM9 liquid medium with shaking, the medium was diluted so that 100 to 200 colonies appear per plate, and then the diluted medium was applied to an LBGM9 plate without drugs. The colonies which grew were replicated on a LBGM9 plate containing 12.5 mg/L of tetracycline and a LBGM9 plate without drugs, and a strain which was sensitive to tetracycline was selected to obtain a strain from which RSFCPG was eliminated, which was designated NP106. The NP106 obtained as described above does not contain the plasmids RSFCPG and pSTVCB, which are harbored by the AJ13601 strain.

The G106S strain is a strain obtained by eliminating only pSTVCB from the AJ13601 strain in a similar manner.

Example 1

L-Glutamic Acid Production using gcd Gene-Deficient Strain (1) Construction of gcd Gene-Deficient Strain Two synthetic DNA primers shown in SEQ ID NOS: 33 and 34 were synthesized by an ordinary method.

The primer shown in SEQ ID NO: 33 had a configuration that the homologous sequence upstream of the gcd gene of Pantoea ananatis was followed by the homologous sequence at the 5' end of λattL-Km$^r$-λattR. The primer of SEQ ID NO: 34 had a configuration that the complementary sequence downstream of the gcd gene of Pantoea ananatis was followed by the complementary sequence at the 3' end of λattL-Km$^r$-λattR. By performing PCR using these primers and pMW118-(λattL-Km$^r$-λattR) as a template, a fragment of about 1.5 kbp in which the homologous sequence upstream of the gcd gene was ligated to the 5' end of the sequence of λattL-Km$^r$-λattR, and the homologous sequence downstream of the gcd gene was ligated to the 3' end of the sequence of λattL-Km$^r$-λattR was amplified.

The aforementioned PCR fragment was purified and used for λ-dependent integration into the Pantoea ananatis chromosome. The helper plasmid RSF-Red-TER was used as a carrier of λ phage Red genes. In order to obtain electrocompetent cells of Pantoea ananatis, the SC17(0) strain was transformed with the RSF-Red-Ter plasmid, and cultured overnight at 34° C. in LB medium containing 50 μg/ml of chloramphenicol. Then, the culture broth was diluted 100 times with fresh LB medium containing 50 μg/ml of chloramphenicol, and the cells grew at 34° C. under aeration until $OD_{600}$ became 0.3. Then, 1 mM IPTG was added, and culture was continued until $OD_{600}$ became 0.7. Cells in 10 mL of the culture were washed 3 times with an equal volume of deionized water, and the cells were suspended in 80 μl of 10% cold glycerol. The aforementioned PCR product was dissolved in 10 μl of deionized water, and 100 to 200 ng of the PCR fragment was added to the cell suspension. Electroporation was done by using a bacterium electroporation apparatus (BioRad, United States, Catalog number 165-2089, Version 2-89). The parameters of the pulse used were a field intensity of 18 kV/cm, and a pulse time of 5 milliseconds.

After the electroporation, 1 ml of the LB medium supplemented with glucose (0.5%) was immediately added to the cell suspension. Then, the cells were allowed to grow at 34° C. for 2 hours under aeration, and selected on the L medium (10 g of Bacto tryptone, 5 g of yeast extract, 5 g of NaCl, and 15 g of agar in 1 L of purified water, pH 7.0) containing 40 mg/L of kanamycin to obtain about 20 transformed colonies. Insertion of the kanamycin resistance gene fragment in the gcd gene region was confirmed by PCR using the two synthetic DNA primers shown in SEQ ID NOS: 35 and 36, and a strain in which insertion of the fragment was confirmed was designated SC17(0)::Δgcd. Genomic DNA was extracted from this strain, and used to transform the NA1 strain by electroporation.

The NA1 strain into which genomic DNA of SC17(0)::Δgcd was introduced was selected on an LBGM9 medium plate supplemented with 40 mg/L of kanamycin, 12.5 mg/L of tetracycline hydrochloride, and 15 g/L of agar. As a result, about 20 transformed colonies were obtained. In all of these strains, the λattL-Km$^r$-λattR fragment was inserted in the gcd gene region, and one clone was selected and designated NA1::Δgcd.

(2) Evaluation of L-Glutamic Acid Producing-Ability of gcd Gene-Deficient Strain In order to examine the effect of the deletion of the gcd gene on L-glutamic acid production, L-glutamic acid production culture was performed by using the NA1::Δgcd and NA1 strains.

The culture was performed in two steps: a seed culture to allow formation of cells, and a main culture to produce L-glutamic acid.

The seed culture was performed with the following medium composition.

Composition of seed culture medium:

| | |
|---|---|
| Sucrose | 50 g/L |
| MgSO$_4$•7H$_2$O | 0.4 g/L |
| GD113 (antifoam) | 0.1 mL/L |
| (NH$_4$)$_2$SO$_4$ | 4.0 g/L |
| KH$_2$PO$_4$ | 2.0 g/L |
| Yeast extract | 4.0 g/L |
| FeSO$_4$•7H$_2$O | 0.01 g/L |
| MnSO$_4$•5H$_2$O | 0.01 g/L |
| Citric acid | 0.02 g/L |
| L-Lysine hydrochloride | 0.4 g/L |
| DL-Methionine | 0.4 g/L |
| ε-Diaminopimelic acid | 0.4 g/L |
| Calcium pantothenate | 18 mg/L |
| Tetracycline hydrochloride | 12.5 mg/L |

The medium was sterilized with steam at 120° C. for 20 minutes.

The NA1::Δgcd and the NA1 strains were each pre-cultured on the LBGM9 medium plate supplemented with 12.5 mg/L of tetracycline and 15 g/L of agar, and cells corresponding to one plate were inoculated into 300 mL of the seed culture medium of the aforementioned composition contained in a 1 L-volume mini jar, and stifling was controlled at 34° C. and pH 6.0 for about 12 hours so that aeration of 1/1 vvm and an oxygen concentration of 3% or higher is obtained. During the culture, pH was controlled to be 6.0 with the addition of ammonia gas. During the culture, pH was controlled to be 6.0 bp adding ammonia gas. The seed culture was terminated at the time of depletion of the saccharide in the medium observed as an index.

Composition of the main culture medium is shown below.
Composition of culture medium (Concentrations are after inoculation of 20% of seed culture medium)

| | |
|---|---|
| Glucose | 100 g/L |
| MgSO$_4$•7H$_2$O | 0.4 g/L |
| GD113 | 0.1 mL/L |
| (NH$_4$)$_2$SO$_4$ | 5.0 g/L |
| KH$_2$PO$_4$ | 6.0 g/L |
| Yeast extract | 6.0 g/L |

-continued

| | |
|---|---|
| FeSO$_4$•7H$_2$O | 0.02 g/L |
| MnSO$_4$•5H$_2$O | 0.02 g/L |
| Citric acid | 0.02 g/L |
| Betaine* | 2.0 g/L |
| L-Lysine hydrochloride | 0.8 g/L |
| DL-Methionine | 0.6 g/L |
| ε-Diaminopimelic acid | 0.6 g/L |
| Calcium pantothenate | 18 mg/L |
| Tetracycline hydrochloride | 25 mg/L |

*N,N,N-trimethylglycine

The cells obtained by the seed culture in a volume of 60 mL were inoculated into 240 mL of medium having the aforementioned composition contained in a 1 L-volume mini jar, and cultured at a temperature of 34° C., 36° C., or 38° C. and at pH 4.9. The culture was terminated when all glucose in the medium was consumed. L-Glutamic acid concentration was measured for the culture supernatant appropriately diluted with water by using Biotech Analyzer (AS-210, Sakura SI).

The results are shown in Table 1. It became clear that accumulation of L-glutamic acid of the gcd gene-deficient strain, NA1::Δgcd strain, was improved as compared with the the control NA1 strain.

TABLE 1

| | Produced L-glutamic acid (g/jar) | | |
|---|---|---|---|
| Strain | 34° C. | 36° C. | 38° C. |
| NA1 | 13.0 | 12.4 | 13.3 |
| NA1::Δgcd | 15.4 | 16.0 | 16.7 |

Example 2

L-Cysteine Production using gcd Gene-Deficient Strain (1) Construction of L-Cysteine-Producing Bacterium In order to investigate the effect of the deletion of the gcd gene on L-cysteine production of *P. ananatis*, an L-cysteine-producing bacterium of *P. ananatis* was constructed.

(1-1) Construction of yeaS Gene Expression Plasmid

First, a plasmid for constructing the aforementioned strain was constructed. The construction method is described below.

By PCR using the chromosomal DNA of *E. coli* MG1655 (ATCC No. 47076) as a template and P11 (agctgagtcg acccccagga aaaattggtt aataac, SEQ ID NO: 51) and P12 (agct-gagcat gcttccaact gcgctaatga cgc, SEQ ID NO: 52) as primers, a DNA fragment containing a promoter region of the nlpD gene (henceforth wild-type nlpD gene promoter is referred to as "Pnlp0") of about 300 bp was obtained. At the 5' and 3' ends of the aforementioned primers, sites for the restriction enzymes SalI and PaeI were designed, respectively. The PCR cycle was as follows: 95° C. for 3 minutes, then 2 cycles of 95° C. for 60 seconds, 50° C. for 30 seconds, and 72° C. for 40 seconds, 25 cycles of 94° C. for 20 seconds, 55° C. for 20 seconds, and 72° C. for 15 seconds, and 72° C. for 5 minutes as the final cycle. The obtained fragment was treated with SalI and PaeI, and inserted into pMIV-5JS (Japanese Patent Laid-open No. 2008-99668) at the SalI-PaeI site to obtain a plasmid pMIV-Pnlp0. The nucleotide sequence of the PaeI-SalI fragment of the Pnlp0 promoter inserted into this pMIV-Pnlp0 plasmid was as shown in SEQ ID NO: 41.

Then, by PCR using the chromosomal DNA of MG1655 as a template, and P13 (agctgatcta gaaaacagaa tttgcctggc ggc, SEQ ID NO: 53) and P14 (agctgaggat ccaggaagag tttgtagaaa cgc, SEQ ID NO: 54) as primers, a DNA fragment containing a terminator region of the rrnB gene of about 300 bp was obtained. At the 5' ends of the aforementioned primers, sites for the restriction enzymes XbaI and BamHI were designed, respectively. The PCR cycle was as follows: 95° C. for 3 minutes, then 2 cycles of 95° C. for 60 seconds, 50° C. for 30 seconds, and 72° C. for 40 seconds, 25 cycles of 94° C. for 20 seconds, 59° C. for 20 seconds, and 72° C. for 15 seconds, and 72° C. for 5 minutes as the final cycle. The obtained fragment was treated with XbaI and BamHI, and inserted into pMIV-Pnlp0 at the XbaI-BamHI site to obtain a plasmid pMIV-Pnlp0-ter.

Then, by PCR using the chromosomal DNA of the MG1655 strain as a template, and P15 (agctgagtcg acgtgttcgc tgaatacggg gt, SEQ ID NO: 55) and P16 (agctgatcta gagaaagcat caggattgca gc, SEQ ID NO: 56) as primers, a DNA fragment of about 700 bp containing the yeaS gene was obtained. At the 5' ends of the aforementioned primers, sites for the restriction enzymes SalI and XbaI were designed, respectively. The PCR cycle was as follows: 95° C. for 3 minutes, then 2 cycles of 95° C. for 60 seconds, 50° C. for 30 seconds, and 72° C. for 40 seconds, 25 cycles of 94° C. for 20 seconds, 55° C. for 20 seconds, and 72° C. for 15 seconds, and 72° C. for 5 minutes as the final cycle. The obtained fragment was treated with SalI and XbaI, and inserted into pMIV-Pnlp0-ter at the SalI-XbaI site to obtain a plasmid pMIV-Pnlp0-YeaS3. As described above, a yeaS expression unit comprising the pMIV-5JS vector on which the nlpD promoter, the yeaS gene, and the rrnB terminator were ligated in this order was constructed.

In order to modify the −10 region of the nlpD promoter to make it a stronger promoter, the −10 region was randomized by the following method. The nlpD promoter region contains two of regions presumed to function as promoters (FIG. 3), and they are indicated as pnlp1 and pnlp2, respectively, in the drawing. By PCR using the plasmid pMIV-Pnlp0 as a template as well as P11 and P17 (atcgtgaaga tcttttccag tgttnannag ggtgccttgc acggtnatna ngtcactgg ("n" means that the corresponding residue can be any of a, t, g and c), SEQ ID NO: 57) as primers, a DNA fragment in which the −10 region contained in the 3' end sequence of the nlpD promoter (referred to as −10(Pnlp1)) was randomized was obtained (FIG. 3). The PCR cycle was as follows: 95° C. for 3 minutes, then 2 cycles of 95° C. for 60 seconds, 50° C. for 30 seconds, and 72° C. for 40 seconds, 25 cycles of 94° C. for 20 seconds, 60° C. for 20 seconds, and 72° C. for 15 seconds, and 72° C. for 5 minutes as the final cycle.

Furthermore, by PCR using the plasmid pMIV-Pnlp0 as a template as well as P12 and P18 (tggaaaagat cttcannnnn cgct-gacctg cg ("n" means that the corresponding residue can be any of a, t, g and c), SEQ ID NO: 58) as primers, a DNA fragment in which the −10 region contained in the 5' end sequence of the nlpD promoter (referred to as −10(Pnlp2)) was randomized was similarly obtained (FIG. 3). The PCR cycle was as follows: 95° C. for 3 minutes, then 2 cycles of 95° C. for 60 seconds, 50° C. for 30 seconds, and 72° C. for 40 seconds, 25 cycles of 94° C. for 20 seconds, 60° C. for 20 seconds, and 72° C. for 15 seconds, and 72° C. for 5 minutes as the final cycle.

The obtained 3' and 5' end fragments could be ligated using the BglII sites designed in the primers P17 and P18, and the full length of the nlpD promoter in which two −10 regions were randomized could be constructed by such ligation. By PCR using this fragment as a template as well as P11 and P12 as primers, a DNA fragment corresponding to a modified type nlpD promoter of the full length was obtained. The PCR cycle was as follows: 95° C. for 3 minutes, then 2 cycles of 95° C. for 60 seconds, 50° C. for 30 seconds, and 72° C. for 40 seconds, 12 cycles of 94° C. for 20 seconds, 60° C. for 20 seconds, and 72° C. for 15 seconds, and 72° C. for 5 minutes as the final cycle.

The amplified fragment was treated with the restriction enzymes SalI and PaeI, for which sites were designed in the 5' ends of the primers, and inserted into the plasmid pMIV-Pnlp0-YeaS3 similarly treated with SalI and PaeI to substitute the mutant Pnlp for the wild-type nlpD promoter region (Pnlp0) on the plasmid. From such plasmids, one having the promoter sequence (Pnlp8) shown in FIG. 3 was selected, and designated pMIV-Pnlp8-YeaS7. The nucleotide sequence of the PaeI-SalI fragment of the Pnlp8 promoter inserted into this plasmid was as shown in SEQ ID NO: 42.

(1-2) Construction of Variant cysE Expression Plasmid

Then, from pMW-Pomp-cysE5 (WO2005/007841), the Pomp-cysE5 cassette portion was excised with PaeI and SacI, and inserted into the same site of pMIV-5JS to construct pMIV-Pomp-CysE5. pMW-Pomp-cysE5 was a plasmid obtained by inserting the cysE5 gene coding for the mutant SAT ligated with the ompC gene promoter into pMW118. From pACYC184 (GenBank/EMBL accession number X06403, available from NIPPON GENE), the tetracycline resistance gene was excised with XbaI and Eco88I, and this gene fragment was treated with the Klenow fragment, and then inserted into pMIV-Pomp-CysE5 at the PvuI site to construct pMT-Pomp-CysE5. Then, pMIV-Pnlp8-YeaS7 was digested with HindIII, blunt-ended with the Klenow fragment, and then digested with NcoI to excise a fragment containing the cassette of the Pnlp8-YeaS-rrnB terminator and the chloramphenicol resistance marker. This fragment was ligated with a SmaI and NcoI digestion fragment of pMT-Pomp-CysE5 similarly having pMIV-5JS as the backbone to construct pMT-EY2. pMT-EY2 is a plasmid which has the Pnlp8-YeaS-rrnB terminator cassette and the Pomp-CysE5 cassette on one plasmid.

(1-3) Introduction of cysE5 and Mutant yeaS into *P. ananatis* SC17 Strain pMT-EY2 described above has the attachment sites of Mu phage originated from pMIV-5JS (Japanese Patent Laid-open No. 2008-99668). By allowing this plasmid to coexist with the helper plasmid pMH10 having Mu transposase (Zimenkov D. et al., Biotechnologiya and (in Russian), 6, 1-22 (2004)) in the same cell, the cassette of PompC-cysE5-Pnlp8-YeaS-rrnB terminator including the chloramphenicol resistance marker located between the attachment sites of Mu phage on this pMT-EY2 plasmid can be inserted into the chromosome of the *P. ananatis* SC17 strain (U.S. Pat. No. 6,596,517). Furthermore, since the chloramphenicol resistance marker located on the pMT-EY2 plasmid exists between the two attachment sites of λ phage (λattR and λattL), the chloramphenicol resistance marker can be excised and removed by the method described later.

First, an SC17 strain introduced with pMH10 by electroporation was selected by overnight culture at 30° C. on the LB agar medium containing 20 mg/L of kanamycin. The obtained transformant was cultured at 30° C., and pMT-E2 was further introduced into this strain by electroporation. This strain, transformed with both pMH10 and pMT-EY2, was given a heat shock at 42° C. for 20 minutes, and colonies of chloramphenicol resistant strains were selected on the LB agar medium containing 20 mg/L of chloramphenicol. The culture temperature for this selection was 39° C. As described above, about 50 clones were obtained, and f pMH10 and pMT-EY2 were cured by culturing each clone at 39° C. for 48 hours on the LB agar medium. A strain showing chloramphenicol resistance due to the insertion of the cassette on the chromosome and showing kanamycin and ampicillin sensitivities due to the curing of both the plasmids was obtained. Furthermore, it was confirmed that the objective cassette was inserted into the chromosome of the obtained strain by PCR using the chromosomal DNA of this strain as a template as well as P11 and P16 as primers. All the obtained clones were designated EY01 to EY50, respectively, and L-cysteine production culture was performed by using the EY01 to EY50 strains. For the culture, the method described later was used. The EY19 strain was selected, which was a clone that produced L-cysteine in the largest amount as a result of the culture.

The chloramphenicol resistance marker introduced into the EY19 strain was removed with an excision system derived from λ phage. Specifically, the EY19 strain was transformed with pMT-Int-Xis2 (WO2005/010175) carrying the Int-Xis gene of λ phage, and an EY19(s) strain showing chloramphenicol sensitivity was obtained from the obtained transformants.

(1-4) Preparation of cysPTWA Gene Expression-Enhanced Strain from EY19(s) Strain Then, in order to enhance expression of the cysPTWA gene, the promoter located upstream of the cysPTWA gene cluster on the chromosome was replaced with the aforementioned potent promoter Pnlp8. A DNA fragment containing the nlp8 promoter of about 300 bp was obtained first by PCR using pMIV-Pnlp8-YeaS7 as a template as well as P11 and P12. The PCR cycle was as follows: 95° C. for 3 minutes, then 2 cycles of 95° C. for 60 seconds, 50° C. for 30 seconds, and 72° C. for 40 seconds, 20 cycles of 94° C. for 20 seconds, 59° C. for 20 seconds, and 72° C. for 15 seconds, and 72° C. for 5 minutes as the final cycle.

The amplified DNA fragment containing nlp8 promoter was treated with the Klenow fragment, inserted into the plasmid pMW118-(λattL-KmR-λattR) (WO2006/093322A2) digested with XbaI and then treated with the Klenow fragment to obtain a plasmid pMW-Km-Pnlp8. By PCR using pMW-Km-Pnlp8 as a template as well as primers P19 (tccgctcacg attttttca tcgctggtaa ggtcatttat cccccaggaa aaattggtta, SEQ ID NO: 59) and P20 (tttcacaccg ctcaaccgca gggcataacc ggcccttgaa gcctgctttt ttatactaag ttg, SEQ ID NO: 60), a DNA fragment of about 1.6 kb containing the Km-Pnlp8 cassette was amplified. The PCR cycle for this amplification was as follows: 95° C. for 3 minutes, then 2 cycles of 95° C. for 60 seconds, 50° C. for 30 seconds, and 72° C. for 40 seconds, 30 cycles of 94° C. for 20 seconds, 54° C. for 20 seconds, and 72° C. for 90 seconds, and 72° C. for 5 minutes as the final cycle. On both the primers, a sequence serving as a target on the chromosome for inserting an objective fragment by λ-dependent integration (the method called "Red-driven integration" (Proc. Natl. Acad. Sci. USA, 2000, vol. 97, No. 12, pp. 6640-6645)) (in this case, a sequence near the promoter of cysPTWA) was designed. Therefore, if the obtained DNA fragment is inserted into the objective strain by this λ-dependent integration, the Km-Pnlp8 is inserted immediately before the cysPTWA gene on the chromosome, and the cysPTWA gene is ligated with the nlp8 promoter. The nucleotide sequence of the cysPTWA gene cluster is shown in SEQ ID NO: 43, and the amino acid sequences encoded by the cysP, cysT and cysW genes are shown in SEQ ID NOS: 44 to 46, respectively. The nucleotide sequence of the cysA gene and the amino acid sequence encoded by this gene are shown in SEQ ID NOS: 47 and 48, respectively.

The *P. ananatis* SC17(0)/RSF-Red-TER strain is a host strain for efficiently performing the λ-dependent integration, and it is a strain obtained by introducing the helper plasmid RSF-Red-TER which expresses gam, bet and exo genes (henceforth referred to as "λ Red genes") into the SC17(0) strain, which is a λ Red gene product-resistant *P. ananatis* strain (WO2008/075483). The SC17(0) strain was deposited at the Russian National Collection of Industrial Microorganisms (VKPM), GNII Genetika (address: Russia, 117545 Moscow, 1 Dorozhny proezd. 1) on Sep. 21, 2005 with an accession number of VKPM B-9246. A method for constructing the RSF-Red-TER plasmid is disclosed in detail in WO2008/075483.

The aforementioned SC17(0)/RSF-Red-TER strain was cultured with addition of IPTG for inducing expression of λ Red genes to prepare cells for electroporation. The aforementioned objective DNA fragment was introduced into these cells by electroporation, and a recombinant strain in which the nlp8 promoter was inserted upstream of the cysPTWA gene by λ-dependent integration was obtained by using the kanamycin resistance as a marker. By PCR using the chromosomal DNA of the obtained strain as a template, as well as P21 (ctttgtccct ttagtgaagg, SEQ ID NO: 61) and P22 (agctgatcta gaagctgact cgagttaatg gcctcccaga cgac, SEQ ID NO: 62) as primers, it was confirmed that the objective structure, Km-Pnlp8-cysPTWA, was formed, and this strain was designated SC17(0)-Pnlp8-PTWA.

Then, the chromosomal DNA of the SC17(0)-Pnlp8-PTWA strain was purified, and 10 μg of this chromosomal DNA was introduced into the EY19(s) strain by electroporation to obtain a kanamycin resistant strain. Amplification was performed by PCR using the chromosomal DNA of the obtained strain as a template as well as P21 and P22 as primers to confirm that the structure of Km-Pnlp8-cysPTWA had been introduced into the chromosome of the EY19(s) strain. The strain obtained as described above was designated the EYP197 strain. Furthermore, the kanamycin resistance marker was removed from the chromosome by using pMT-Int-Xis2 as described above, and the strain that became kanamycin sensitive was designated as the EYP197(s) strain.

(1-5) Preparation of Mutant 3-Phosphoglycerate Dehydrogenase (serA348) Gene-Carrying Strain of EYP197(s) Strain As a gene of 3-phosphoglycerate dehydrogenase to be introduced into the L-cysteine-producing bacterium, the serA348 gene which is a gene coding for 3-phosphoglycerate dehydrogenase of *Pantoea ananatis* and coding for a mutant enzyme including a mutation for substitution of an alanine residue for the asparagine residue at the 348th position (N348A) (J. Biol. Chem., 1996, 271 (38):23235-8) was constructed by the following method.

The sequence of the wild-type serA gene derived from *Pantoea ananatis* is shown in SEQ ID NO: 49. The amino acid sequence encoded by this gene is shown in SEQ ID NO: 50. In order to obtain a 3'-end side DNA fragment of the serA gene into which the aforementioned mutation was introduced, PCR was performed by using the chromosomal DNA of the SC17 strain as a template as well as P23 (agctgagtcg acatggcaaa ggtatcactg gaa, SEQ ID NO: 63) and P24 (gagaacgccc gggcgggctt cgtgaatatg cagc, SEQ ID NO: 64) as primers (95° C. for 3 minutes, then 2 cycles of 95° C. for 60 seconds, 50° C. for 30 seconds, and 72° C. for 40 seconds, 25 cycles of 94° C. for 20 seconds, 60° C. for 20 seconds, and 72° C. for 60 seconds, and 72° C. for 5 minutes as the final cycle). Then, in order to obtain a 5'-end side DNA fragment into which the mutation was introduced, PCR was performed in the same manner by using the chromosomal DNA of the SC17 strain as a template as well as P25 (agctgatcta gacgtgggat cagtaaagca gg, SEQ ID NO: 65) and P26 (aaaaccgccc gggcgttctc ac, SEQ ID NO: 66) as primers (95° C. for 3 minutes, then 2 cycles of 95° C. for 60 seconds, 50° C. for 30 seconds, and 72° C. for 40 seconds, 20 cycles of 94° C. for 20 seconds, 60° C. for 20 seconds, and 72° C. for 20 seconds, and 72° C. for 5 minutes as the final cycle). Both the obtained PCR fragments were treated with the restriction enzyme SmaI, and ligated by using a DNA ligase to obtain a DNA fragment corresponding to a full length mutant serA gene including the objective mutation (N348A). This DNA fragment was amplified by PCR using it as a template and P23 and P25 as primers (95° C. for 3 minutes, then 2 cycles of 95° C. for 60 seconds, 50° C. for 30 seconds, and 72° C. for 40 seconds, 15 cycles of 94° C. for 20 seconds, 60° C. for 20 seconds, and 72° C. for 75 seconds, and 72° C. for 5 minutes as the final cycle). The SalI and the XbaI restriction enzyme sites designed in the P23 and P25 primers were treated with SalI and XbaI, and the fragment was inserted into pMIV-Pnlp8-ter similarly treated with SalI and XbaI to prepare pMIV-Pnlp8-serA348.

The constructed pMIV-Pnlp8-serA348 carried the attachment site of Mu originating in pMIV-5JS (Japanese Patent Laid-open No. 2008-99668). By using this plasmid together with the helper plasmid pMH10 having Mu transposase, the cassette of Pnlp8-serA348-rrnB terminator including the chloramphenicol resistance marker can be inserted into the chromosome of the *P. ananatis* SC17 strain, as described above. The pMIV-Pnlp8-serA348 plasmid and pMH10 were introduced into the SC17(0) strain to obtain a strain in which the cassette of Pnlp8-serA348-rrnB terminator was inserted into the chromosome. By PCR using the primers P11 and P25, it was confirmed that the objective cassette existed in the cells. The 3-phosphoglycerate dehydrogenase activity in cell extracts of 50 of the obtained clones was measured, and a strain which showed the highest activity was selected, and designated SC17int-serA348 strain. Then, 10 μg of the chromosomal DNA of the SC17int-serA348 strain was introduced into the EYP197(s) strain by electroporation to obtain a chloramphenicol resistant strain, and by PCR using the primers P11 and P25, it was confirmed that the structure of Pnlp8-serA348 had been introduced together with the chloramphenicol resistance marker into the chromosome of the EYP197(s) strain. The strain obtained as described above was designated EYPS1976 strain.

By the aforementioned method for removing marker using pMT-Int-Xis2, the chloramphenicol resistance marker was removed, and the strain that became chloramphenicol sensitive was designated EYPS1976(s) strain.

(1-6) Preparation of gcd Gene-Deficient Strain from EYPS1976(s) Strain

Genomic DNA was prepared from the SC17(0)::Δgcd strain described in Example 1, and introduced into the EYPS1976(s) strain by electroporation, and a gcd gene-deficient strain (EYPS1976Δgcd strain) was obtained from the EYPS1976(s) strain by using kanamycin resistance as a marker.

(2) Culture of L-Cysteine-Producing Bacteria EYPS1976(s) Strain and EYPS1976Δgcd Strain In order to investigate the effect of deletion of the gcd gene on fermentative production of L-cysteine and O-acetylserine, which is a precursor of L-cysteine, fermentative production thereof was performed by using the L-cysteine-producing bacterium EYPS1976(s) strain and the gcd gene-deficient strain EYPS1976Δgcd derived from the EYPS1976(s) strain, and amounts of produced L-cysteine and O-acetylserine were compared. For the culture, an L-cysteine production medium having the following composition was used.

L-Cysteine production medium (concentrations of the components are final concentrations)

| Component 1: | |
|---|---|
| $(NH_4)_2SO_4$ | 15 g/L |
| $KH_2PO_4$ | 1.5 g/L |
| $MgSO_4 \cdot 7H_2O$ | 1 g/L |
| Thiamine hydrochloride | 0.1 mg/L |
| Component 2: | |
| $FeSO_4 \cdot 7H_2O$ | 1.7 mg/L |
| $Na_2MoO_4 \cdot 2H_2O$ | 0.15 mg/L |
| $CoCl_2 \cdot 6H_2O$ | 0.7 mg/L |
| $MnCl \cdot 4H_2O$ | 1.6 mg/L |
| $ZnSO_4 \cdot 7H_2O$ | 0.3 mg/L |
| $CuSO_4 \cdot 5H_2O$ | 0.25 mg/L |
| Component 3: | |
| Tryptone | 0.6 g/L |
| Yeast extract | 0.3 g/L |
| Sodium chloride | 0.6 g/L |
| Component 4: | |
| Calcium carbonate | 20 g/L |
| Component 5: | |
| L-Histidine monohydrochloride monohydrate | 135 mg/L |
| Component 6: | |
| Sodium thiosulfate | 6 g/L |
| Component 7: | |
| Pyridoxine hydrochloride | 2 mg/L |
| Component 8: | |
| Glucose | 40 g/L |

For these components, there were prepared stock solutions of 10-fold concentration (component 1), 1000-fold concentration (component 2), 100/6-fold concentration (component 3), 100-fold concentration (component 5), 350 g/L (component 6), 1000-fold concentration (component 7), and 10-fold concentration (component 8), they were mixed at the time of use, and the defined volume was obtained with sterilized water to attain the final concentrations. Sterilization was performed by autoclaving at 110° C. for 30 minutes (components 1, 2, 3, 5 and 8), hot air sterilization at 180° C. for 5 hours or longer (component 4), or filter sterilization (components 6 and 7).

The L-cysteine production culture was performed as follows. The EYPS1976(s) strain and the EYPS1976Δgcd strain were each applied and spread on the LB agar medium to perform pre-culture overnight at 34° C., and then cells corresponding to 7 cm on the plate were scraped twice with an inoculation loop of 10-μl size (NUNC Blue Loop), and inoculated into 2 ml of the L-cysteine production medium contained in a large test tube (internal diameter: 23 mm, length: 20 cm) at substantially the same cell amounts at the time of the start of the culture.

The strains were cultured at 34° C. or 38° C. with shaking, and the culture was terminated after 24 hours. At this point, it was confirmed that glucose as the carbon source was completely consumed. L-Cysteine produced in the medium was quantified by the method described by Gaitonde, M. K. (Biochem. J., 1967 Aug., 104(2):627-33). OAS (O-acetylserine) produced in the medium was quantified by HPLC. In this quantification, a method of converting OAS into more stable NAS (N-acetylserine) by diluting the sample with 200 mM Tris-HCl (pH 9.0) and detecting NAS was used. The HPLC conditions were as follows.

Column: Inertsil ODS-3 (hydrophobic column, GL Science Co., Ltd.)
Buffer flow rate: 1.0 mL/minute
Column temperature: 40° C.
Detection: UV 210 nm
Application volume of sample: 10 mL
Buffer: 0.1 M $KH_2PO_4.H_3PO_4$ (pH 2.2), 5 mM Na 1-octanesulfonate The experiment was performed in hexaplicate for each strain, and the results were indicated in Table 2 with averages and standard deviations. As shown in Table 2, it was found that deletion of the gcd gene was effective for increasing L-cysteine and O-acetylserine at both the culture temperatures of 34° C. and 38° C. The degree of the increase was more remarkable at 38° C., and thus it was found that it was especially effective for culture at high temperature. It was also found that it was also effective for increasing cell amount (OD) at 38° C.

TABLE 2

L-Cysteine and NAS producing ability of gcd gene-deficient strain

|  |  | Cys (g/L) | NAS (g/L) | OD600 |
|---|---|---|---|---|
| 34° C. | EYPS1976(s) | 1.02 ± 0.16 | 0.81 ± 0.10 | 15.1 ± 0.50 |
|  | EYPS1976 Δgcd | 1.29 ± 0.16 | 1.01 ± 0.10 | 15.0 ± 0.24 |
| 38° C. | EYPS1976(s) | 0.31 ± 0.12 | 0.54 ± 0.11 | 11.1 ± 1.68 |
|  | EYPS1976 Δgcd | 0.95 ± 0.21 | 0.87 ± 0.10 | 19.2 ± 0.57 |

EXPLANATION OF SEQUENCE LISTING

SEQ ID NO: 1: Nucleotide sequence of *Pantoea ananatis* gcd gene
SEQ ID NO: 2: Amino acid sequence of *Pantoea ananatis* GCD
SEQ ID NO: 3: Nucleotide sequence of *Pantoea ananatis* hisD gene
SEQ ID NO: 4: Primer for amplification of fragment for integration of Km$^r$ gene into hisD gene
SEQ ID NO: 5: Primer for amplification of fragment for integration of Km$^r$ gene into hisD gene
SEQ ID NO: 6: Primer for cat gene amplification
SEQ ID NO: 7: Primer for cat gene amplification
SEQ ID NO: 8: Primer for sacB gene amplification
SEQ ID NO: 9: Primer for sacB gene amplification
SEQ ID NO: 10: Primer for amplification of DNA fragment including PlacUV5 promoter
SEQ ID NO: 11: Primer for amplification of DNA fragment including PlacUV5 promoter
SEQ ID NO: 12: Primer for amplification of DNA fragment including λRedαβγ genes and tL3
SEQ ID NO: 13: Primer for amplification of DNA fragment including λRedαβγ genes and tL3
SEQ ID NO: 14: Primer for amplification of DNA fragment including PlacUV5 promoter and TrrnB
SEQ ID NO: 15: Primer for amplification of DNA fragment including PlacUV5 promoter and TrrnB
SEQ ID NO: 16: Primer for attL amplification
SEQ ID NO: 17: Primer for attL amplification
SEQ ID NO: 18: Nucleotide sequence of attL
SEQ ID NO: 19: Primer for attR amplification
SEQ ID NO: 20: Primer for attR amplification
SEQ ID NO: 21: Nucleotide sequence of attR
SEQ ID NO: 22: Primer for amplification of DNA fragment including bla gene
SEQ ID NO: 23: Primer for amplification of DNA fragment including bla gene
SEQ ID NO: 24: Primer for amplification of DNA fragment including ter_rrnB
SEQ ID NO: 25: Primer for amplification of DNA fragment including ter_rrnB
SEQ ID NO: 26: Nucleotide sequence of DNA fragment including ter_thrL terminator
SEQ ID NO: 27: Primer for amplification of DNA fragment including ter_thrL terminator
SEQ ID NO: 28: Primer for amplification of DNA fragment including ter_thrL terminator
SEQ ID NO: 29: Primer for amplifying gltA gene except for ORF
SEQ ID NO: 30: Primer for amplifying gltA gene except for ORF
SEQ ID NO: 31: Primer for prpC gene amplification
SEQ ID NO: 32: Primer for prpC gene amplification
SEQ ID NO: 33: Primer for deletion of gcd gene
SEQ ID NO: 34: Primer for deletion of gcd gene
SEQ ID NO: 35: Primer for confirming deletion of gcd gene
SEQ ID NO: 36: Primer for confirming deletion of gcd gene
SEQ ID NO: 37: Nucleotide sequence of wild-type cysE gene
SEQ ID NO: 38: Amino acid sequence of serine acetyltransferase encoded by wild-type cysE
SEQ ID NO: 39: Nucleotide sequence of wild-type yeaS gene
SEQ ID NO: 40: Amino acid sequence of wild-type YeaS
SEQ ID NO: 41: Nucleotide sequence of Pnlp0
SEQ ID NO: 42: Nucleotide sequence of Pnlp8
SEQ ID NO: 43: Nucleotide sequence of cysPTWA gene cluster
SEQ ID NO: 44: Amino acid sequence encoded by cysP gene
SEQ ID NO: 45: Amino acid sequence encoded by cysT gene
SEQ ID NO: 46: Amino acid sequence encoded by cysW gene
SEQ ID NO: 47: Nucleotide sequence of cysA gene
SEQ ID NO: 48: Amino acid sequence encoded by cysA gene
SEQ ID NO: 49: Nucleotide sequence of *Pantoea ananatis* wild-type serA gene
SEQ ID NO: 50: Amino acid sequence encoded by *Pantoea ananatis* wild-type serA gene
SEQ ID NOS: 51 to 66: Primers P11 to P26

INDUSTRIAL APPLICABILITY

By using the microorganism of the presently disclosed subject matter, an L-amino acid such as L-glutamic acid, L-lysine, L-threonine, L-arginine, L-histidine, L-isoleucine, L-valine, L-leucine, L-threonine, L-phenylalanine, L-tyrosine, L-tryptophan, or L-cysteine can be efficiently produced by fermentation.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid comprising:
   A) culturing a bacterium which belongs to the family Enterobacteriaceae and is able to produce an L-amino acid in a medium, and
   B) collecting the L-amino acid from the medium or the bacterium, wherein the bacterium has been modified so that the native activity of glucose dehydrogenase, which uses pyrroloquinoline quinone as a coenzyme, is reduced as compared to an unmodified bacterium, wherein the glucose dehydrogenase activity is reduced by decreasing expression of a gcd gene on the bacterium's chromosome, by a method selected from the group consisting of:
   a) inserting a transposon sequence into the coding region of the gcd gene so that the expression is disrupted,
   b) deleting all or a part of an expression control sequence of the gene,
   c) inserting one or more nucleotides into an expression control sequence of the gene so that the expression control sequence is no longer functional,
   d) deleting a part of or the entire gcd gene on the chromosome, and
   e) introducing a mutation selected from the group consisting of an amino acid substitution, a stop codon, and a frame shift mutation into the coding region of the gene on the chromosome so that the expression is disrupted, and
   f) combinations thereof.

2. The method according to claim 1, wherein the gcd gene comprises a DNA encoding the amino acid sequence of SEQ ID NO: 2 or an amino acid sequence having a homology of not less than 95% to the amino acid sequence of SEQ ID NO: 2.

3. The method according to claim 1, wherein the L-amino acid is selected from the group consisting of L-glutamic acid, L-lysine, L-threonine, L-arginine, L-histidine, L-isoleucine, L-valine, L-leucine, L-phenylalanine, L-tyrosine, L-tryptophan, L-cysteine, and combinations thereof.

4. The method according to claim 3, wherein the L-amino acid is L-glutamic acid or L-cysteine.

5. The method according to claim 4, wherein the L-amino acid is L-glutamic acid, and an activity or activities of an enzyme selected from the group consisting of citrate synthase, methyl citrate synthase, phosphoenolpyruvate carboxylase, glutamate dehydrogenase, and combinations thereof, are enhanced in the bacterium by a method selected from the group consisting of:
  a) increasing the copy number of a gene encoding the enzyme, and
  b) introducing a mutation into a promoter region of the gene.

6. The method according to claim 4, wherein the L-amino acid is L-cysteine, and an activity or activities of an enzyme selected from the group consisting of 3-phosphoglycerate dehydrogenase, serine acetyltransferase, sulfate/thiosulfate transport system, and combinations thereof, are enhanced, and/or expression of a yeaS gene is enhanced wherein said activity or expression is enhanced by a method selected from the group consisting of:
  a) increasing the copy number of a gene encoding the enzyme and/or the yeaS gene, and
  b) introducing a mutation into a promoter region of the gene.

7. The method according to 1, wherein the bacterium belongs to a genus selected from the group consisting of *Pantoea, Enterobacter, Erwinia, Klebsiella, Providencia, Salmonella, Serratia, Morganella*, and *Yersinia*.

\* \* \* \* \*

SEQUENCE LISTING

<160> NUMBER OF SEQ ID NOS: 67

<210> SEQ ID NO 1
<211> LENGTH: 2931
<212> TYPE: DNA
<213> ORGANISM: Pantoea anantis
<220> FEATURE:
<221> NAME/KEY: CDS
<222> LOCATION: (301)..(2691)

<400> SEQUENCE: 1

```
gcgtctggcg atctcattcc ctttacgctt taacctttct tatctcctgg cactattgaa      60
tcatatcggc aaggcccat taacaccctc taaagtattg ccttagatgc gttgttaaga     120
gctttaagcc aaaaaaatca aaactcatac caattttgct ataacattta acagatatgg    180
atcatcacgc ttcagggaag agcgaaataa gaatgccttt catcttttgt actttatgac    240
tgacaacaat ctatctgatt gttttcctga gttttctggc aacgaaatga ggtcaacatt    300
```

| atg | ggg | aaa | aac | tcc | tca | tcc | ttt | agc | gtg | gtc | cgt | ttt | tta | acg | gtg |    348 |
|-----|-----|-----|-----|-----|-----|-----|-----|-----|-----|-----|-----|-----|-----|-----|-----|--------|
| Met | Gly | Lys | Asn | Ser | Ser | Ser | Phe | Ser | Val | Val | Arg | Phe | Leu | Thr | Val | |
| 1   |     |     |     | 5   |     |     |     |     | 10  |     |     |     |     | 15  |     | |

| ctg | ttc | gcc | gtg | cta | acg | ggt | gcg | ttc | atg | tta | att | ggt | ggt | atc | tgg |    396 |
|-----|-----|-----|-----|-----|-----|-----|-----|-----|-----|-----|-----|-----|-----|-----|-----|--------|
| Leu | Phe | Ala | Val | Leu | Thr | Gly | Ala | Phe | Met | Leu | Ile | Gly | Gly | Ile | Trp | |
|     |     |     | 20  |     |     |     |     | 25  |     |     |     |     | 30  |     |     | |

| ctg | gcc | acg | atc | ggt | ggt | tcc | tgg | tac | tac | atc | atc | ggc | ggt | gca | gcc |    444 |
|-----|-----|-----|-----|-----|-----|-----|-----|-----|-----|-----|-----|-----|-----|-----|-----|--------|
| Leu | Ala | Thr | Ile | Gly | Gly | Ser | Trp | Tyr | Tyr | Ile | Ile | Gly | Gly | Ala | Ala | |
|     |     | 35  |     |     |     |     | 40  |     |     |     |     | 45  |     |     |     | |

| atg | ctg | ctt | acc | gct | ttc | ctg | ctg | tgg | cga | cgt | aac | agc | gct | gcc | ctg |    492 |
|-----|-----|-----|-----|-----|-----|-----|-----|-----|-----|-----|-----|-----|-----|-----|-----|--------|
| Met | Leu | Leu | Thr | Ala | Phe | Leu | Leu | Trp | Arg | Arg | Asn | Ser | Ala | Ala | Leu | |
| 50  |     |     |     |     | 55  |     |     |     |     | 60  |     |     |     |     |     | |

| gtt | gtc | tat | gcg | ctc | tta | ctg | ctg | gct | acg | ctg | gcc | tgg | ggc | gtt | tgg |    540 |
|-----|-----|-----|-----|-----|-----|-----|-----|-----|-----|-----|-----|-----|-----|-----|-----|--------|
| Val | Val | Tyr | Ala | Leu | Leu | Leu | Leu | Ala | Thr | Leu | Ala | Trp | Gly | Val | Trp | |
| 65  |     |     |     | 70  |     |     |     |     | 75  |     |     |     |     | 80  |     | |

| gaa | gtc | ggc | acc | gac | ttc | tgg | gca | ctg | gca | ccg | cgt | acc | gac | gta | ctg |    588 |
|-----|-----|-----|-----|-----|-----|-----|-----|-----|-----|-----|-----|-----|-----|-----|-----|--------|
| Glu | Val | Gly | Thr | Asp | Phe | Trp | Ala | Leu | Ala | Pro | Arg | Thr | Asp | Val | Leu | |
|     |     |     |     | 85  |     |     |     |     | 90  |     |     |     |     | 95  |     | |

| gtg | atc | ttt | ggc | gtc | tgg | ctg | gtg | ttg | ccc | ttt | gtc | tat | cgc | ggc | tta |    636 |
|-----|-----|-----|-----|-----|-----|-----|-----|-----|-----|-----|-----|-----|-----|-----|-----|--------|
| Val | Ile | Phe | Gly | Val | Trp | Leu | Val | Leu | Pro | Phe | Val | Tyr | Arg | Gly | Leu | |
|     |     |     | 100 |     |     |     |     | 105 |     |     |     |     | 110 |     |     | |

| tac | cag | ccg | ggt | aaa | ggc | gca | ctg | ggt | gcc | atg | ggc | gta | gcg | ctg | gtt |    684 |
|-----|-----|-----|-----|-----|-----|-----|-----|-----|-----|-----|-----|-----|-----|-----|-----|--------|
| Tyr | Gln | Pro | Gly | Lys | Gly | Ala | Leu | Gly | Ala | Met | Gly | Val | Ala | Leu | Val | |
|     |     | 115 |     |     |     |     | 120 |     |     |     |     | 125 |     |     |     | |

| gcc | agt | gca | gcg | gtg | tta | acc | tat | tcc | gtc | ttt | aat | gat | ccg | caa | gtg |    732 |
|-----|-----|-----|-----|-----|-----|-----|-----|-----|-----|-----|-----|-----|-----|-----|-----|--------|
| Ala | Ser | Ala | Ala | Val | Leu | Thr | Tyr | Ser | Val | Phe | Asn | Asp | Pro | Gln | Val | |
| 130 |     |     |     |     | 135 |     |     |     |     | 140 |     |     |     |     |     | |

| gtt | aac | ggt | gca | tta | ccg | gca | aca | gcg | gat | aat | gcg | cct | cag | gca | cag |    780 |
|-----|-----|-----|-----|-----|-----|-----|-----|-----|-----|-----|-----|-----|-----|-----|-----|--------|
| Val | Asn | Gly | Ala | Leu | Pro | Ala | Thr | Ala | Asp | Asn | Ala | Pro | Gln | Ala | Gln | |
| 145 |     |     |     | 150 |     |     |     |     | 155 |     |     |     |     | 160 |     | |

| ccg | ttg | agc | aat | att | gct | gat | ggt | gac | tgg | ccg | gcc | tat | gcg | cgc | gat |    828 |
|-----|-----|-----|-----|-----|-----|-----|-----|-----|-----|-----|-----|-----|-----|-----|-----|--------|
| Pro | Leu | Ser | Asn | Ile | Ala | Asp | Gly | Asp | Trp | Pro | Ala | Tyr | Ala | Arg | Asp | |
|     |     |     | 165 |     |     |     |     | 170 |     |     |     |     | 175 |     |     | |

| cag | caa | ggg | acg | cgc | ttc | tcg | ccg | ctc | aag | cag | atc | aac | cac | gac | aat |    876 |
|-----|-----|-----|-----|-----|-----|-----|-----|-----|-----|-----|-----|-----|-----|-----|-----|--------|
| Gln | Gln | Gly | Thr | Arg | Phe | Ser | Pro | Leu | Lys | Gln | Ile | Asn | His | Asp | Asn | |
|     |     | 180 |     |     |     |     | 185 |     |     |     |     | 190 |     |     |     | |

| gtg | aaa | gaa | ctg | cag | gtt | gcc | tgg | caa | ttc | cag | acc | ggt | gat | atg | aaa |    924 |
|-----|-----|-----|-----|-----|-----|-----|-----|-----|-----|-----|-----|-----|-----|-----|-----|--------|
| Val | Lys | Glu | Leu | Gln | Val | Ala | Trp | Gln | Phe | Gln | Thr | Gly | Asp | Met | Lys | |
|     | 195 |     |     |     |     | 200 |     |     |     |     | 205 |     |     |     |     | |

| cgc | cca | agc | gat | ccg | ggc | gaa | att | acc | gat | gaa | gtg | acg | cca | atc | aag |    972 |
|-----|-----|-----|-----|-----|-----|-----|-----|-----|-----|-----|-----|-----|-----|-----|-----|--------|
| Arg | Pro | Ser | Asp | Pro | Gly | Glu | Ile | Thr | Asp | Glu | Val | Thr | Pro | Ile | Lys | |
| 210 |     |     |     |     | 215 |     |     |     |     | 220 |     |     |     |     |     | |

-continued

| | | |
|---|---|---|
| att cgc gac acg ctg tat ctt tgc acg cca cat cag att tta ttt gct<br>Ile Arg Asp Thr Leu Tyr Leu Cys Thr Pro His Gln Ile Leu Phe Ala<br>225                 230                235                240 | 1020 |
| ctg gat gcg gcc acc ggc aag caa aag tgg aag ttt gat ccc ggc ctg<br>Leu Asp Ala Ala Thr Gly Lys Gln Lys Trp Lys Phe Asp Pro Gly Leu<br>                245                250                255 | 1068 |
| aaa acc aac cca acc ttc cag cac gtg acc tgt cgt ggt gtg tca tac<br>Lys Thr Asn Pro Thr Phe Gln His Val Thr Cys Arg Gly Val Ser Tyr<br>                260                265                270 | 1116 |
| cac gaa ttc cct gca gcg aag gat gcg tcc aat acc cag cct gcg ctg<br>His Glu Phe Pro Ala Ala Lys Asp Ala Ser Asn Thr Gln Pro Ala Leu<br>            275                280                285 | 1164 |
| tgc tcg cgt cgt atc tac ctg cca gtc aat gac ggg cgt ttg ttc gcg<br>Cys Ser Arg Arg Ile Tyr Leu Pro Val Asn Asp Gly Arg Leu Phe Ala<br>        290                295                300 | 1212 |
| ctg gat gcg gaa acc ggt gaa cgc tgc ccg gcc ttt ggt aac aac ggt<br>Leu Asp Ala Glu Thr Gly Glu Arg Cys Pro Ala Phe Gly Asn Asn Gly<br>305                 310                315                320 | 1260 |
| gag ctg gat ctg cag cac aag cag ccg gtc aca acg cca ggc atg tat<br>Glu Leu Asp Leu Gln His Lys Gln Pro Val Thr Thr Pro Gly Met Tyr<br>                325                330                335 | 1308 |
| gag cca acc tcg cca ccg gtg att act gac acc acc att gtg atg gct<br>Glu Pro Thr Ser Pro Pro Val Ile Thr Asp Thr Thr Ile Val Met Ala<br>            340                345                350 | 1356 |
| ggc gcg gta acc gat aac ttt tca acc cgt gaa cct tca ggc gcc atc<br>Gly Ala Val Thr Asp Asn Phe Ser Thr Arg Glu Pro Ser Gly Ala Ile<br>        355                360                365 | 1404 |
| cgt ggc ttt gat gtg aac acc ggt aag ctg ttg tgg gtg ttc gat ccg<br>Arg Gly Phe Asp Val Asn Thr Gly Lys Leu Leu Trp Val Phe Asp Pro<br>        370                375                380 | 1452 |
| ggc gcg aaa gat cct aac gcg att ccg gcg gat gaa cac acg ttc acc<br>Gly Ala Lys Asp Pro Asn Ala Ile Pro Ala Asp Glu His Thr Phe Thr<br>385                 390                395                400 | 1500 |
| atg aac tcc cct aac tcg tgg gca cct gcg gtt tac gat ccg aag ctg<br>Met Asn Ser Pro Asn Ser Trp Ala Pro Ala Val Tyr Asp Pro Lys Leu<br>                405                410                415 | 1548 |
| gat atc gtt tac ctg cca atg ggg gtg acc acg ccg gat atc tgg ggc<br>Asp Ile Val Tyr Leu Pro Met Gly Val Thr Thr Pro Asp Ile Trp Gly<br>            420                425                430 | 1596 |
| ggc aac cgc aca cct gag cag gaa cgt tat gcc agc agc gtg ctg gcg<br>Gly Asn Arg Thr Pro Glu Gln Glu Arg Tyr Ala Ser Ser Val Leu Ala<br>        435                440                445 | 1644 |
| ctg aac gcg acg acc ggt aag ctg gtg tgg tca tat cag act gtg cat<br>Leu Asn Ala Thr Thr Gly Lys Leu Val Trp Ser Tyr Gln Thr Val His<br>450                 455                460 | 1692 |
| cac gat ctg tgg gat atg gac ctg cct tcg cag ccg acg ctg gcg gat<br>His Asp Leu Trp Asp Met Asp Leu Pro Ser Gln Pro Thr Leu Ala Asp<br>465                 470                475                480 | 1740 |
| att acc gat aaa gac ggt aat acc gtg ccg gtt atc tat gcc cct gcc<br>Ile Thr Asp Lys Asp Gly Asn Thr Val Pro Val Ile Tyr Ala Pro Ala<br>                485                490                495 | 1788 |
| aaa acc ggg aac atc ttt gtt ctg gat cgc cgc aca ggt aaa act gtg<br>Lys Thr Gly Asn Ile Phe Val Leu Asp Arg Arg Thr Gly Lys Thr Val<br>            500                505                510 | 1836 |
| gtt ccg gcc ccg gaa acc cct gtt ccg cag ggc gca gct aag ggc gac<br>Val Pro Ala Pro Glu Thr Pro Val Pro Gln Gly Ala Ala Lys Gly Asp<br>        515                520                525 | 1884 |
| cat gtc tca gct aca cag cct tac tct gaa ctg acc ttc cgt ccg aaa<br>His Val Ser Ala Thr Gln Pro Tyr Ser Glu Leu Thr Phe Arg Pro Lys<br>530                 535                540 | 1932 |

| cag aac ctg acg gat aag gac atg tgg ggc gcg acg atg tat gac cag | 1980 |
| Gln Asn Leu Thr Asp Lys Asp Met Trp Gly Ala Thr Met Tyr Asp Gln | |
| 545 550 555 560 | |

| ctg gtg tgc cgc gtg att ttc aaa cgt ctg cgc tac gaa ggt ccg ttc | 2028 |
| Leu Val Cys Arg Val Ile Phe Lys Arg Leu Arg Tyr Glu Gly Pro Phe | |
| 565 570 575 | |

| acg cca cct tct gag cag ggc acc ctg gtc ttc ccg ggc aac ctg ggc | 2076 |
| Thr Pro Pro Ser Glu Gln Gly Thr Leu Val Phe Pro Gly Asn Leu Gly | |
| 580 585 590 | |

| atg ttt gaa tgg ggc ggc att tcc gtt gat ccg cat cgt cag att gcg | 2124 |
| Met Phe Glu Trp Gly Gly Ile Ser Val Asp Pro His Arg Gln Ile Ala | |
| 595 600 605 | |

| att gct aac cca atg gcg ctg ccg ttc gtg tct aag ctg atc cca cgc | 2172 |
| Ile Ala Asn Pro Met Ala Leu Pro Phe Val Ser Lys Leu Ile Pro Arg | |
| 610 615 620 | |

| ggt ccg ggt aat ccg gaa gag cca cca aaa ggc gca acg ggc ggt tca | 2220 |
| Gly Pro Gly Asn Pro Glu Glu Pro Pro Lys Gly Ala Thr Gly Gly Ser | |
| 625 630 635 640 | |

| ggt act gaa acc ggt att cag ccg cag tac ggt gtg cca tat ggc gtt | 2268 |
| Gly Thr Glu Thr Gly Ile Gln Pro Gln Tyr Gly Val Pro Tyr Gly Val | |
| 645 650 655 | |

| gaa ctg aat ccg ttc ctg tca cct ttt ggt ctg ccg tgt aaa caa cct | 2316 |
| Glu Leu Asn Pro Phe Leu Ser Pro Phe Gly Leu Pro Cys Lys Gln Pro | |
| 660 665 670 | |

| gca tgg ggt tat gtt tct gct gtt gac ctg aaa acc aac gaa gtg gtg | 2364 |
| Ala Trp Gly Tyr Val Ser Ala Val Asp Leu Lys Thr Asn Glu Val Val | |
| 675 680 685 | |

| tgg aaa caa cgt att ggt acc gtt cgt gac agc tca cct gta ccg ctg | 2412 |
| Trp Lys Gln Arg Ile Gly Thr Val Arg Asp Ser Ser Pro Val Pro Leu | |
| 690 695 700 | |

| ccc ttt aaa atg ggt atg cca atg ctg ggc gga ccg gtt gcc acc gca | 2460 |
| Pro Phe Lys Met Gly Met Pro Met Leu Gly Gly Pro Val Ala Thr Ala | |
| 705 710 715 720 | |

| ggc aaa gtg ttc ttt att ggc gca acg gct gat aac tac ctg cgc gct | 2508 |
| Gly Lys Val Phe Phe Ile Gly Ala Thr Ala Asp Asn Tyr Leu Arg Ala | |
| 725 730 735 | |

| ttc agc acc gac acc ggt gaa ctc ttg tgg cag gcg cgc ctg cca gcc | 2556 |
| Phe Ser Thr Asp Thr Gly Glu Leu Leu Trp Gln Ala Arg Leu Pro Ala | |
| 740 745 750 | |

| ggt ggt cag gca acg cca atg acc tat gaa gtt aac ggc aag caa tac | 2604 |
| Gly Gly Gln Ala Thr Pro Met Thr Tyr Glu Val Asn Gly Lys Gln Tyr | |
| 755 760 765 | |

| gtt gtg att gct gcc ggt ggc cat ggt tca ttc ggc acc aag ctg ggc | 2652 |
| Val Val Ile Ala Ala Gly Gly His Gly Ser Phe Gly Thr Lys Leu Gly | |
| 770 775 780 | |

| gat tac gtg att gcc tat gcg ctg ccc gac cag aag taa ttaacacctg | 2701 |
| Asp Tyr Val Ile Ala Tyr Ala Leu Pro Asp Gln Lys | |
| 785 790 795 | |

| aacagaggcg gactccggtc cgccttttt tatgcctgct atctgccctg tgcttttgcg | 2761 |

| cgtggggagc gccagcttaa ccaggcgcac agccccatga ccatgcaggt ggccagaaat | 2821 |

| actggccgca ttcccacgc gccaccaatc acccaccaa aaaggggacc actgacctgg | 2881 |

| ccgatatact gcgccgacgt cgaatagccg agcatgcgcc ccacctgcac | 2931 |

<210> SEQ ID NO 2
<211> LENGTH: 796
<212> TYPE: PRT
<213> ORGANISM: Pantoea anantis

<400> SEQUENCE: 2

```
Met Gly Lys Asn Ser Ser Phe Ser Val Arg Phe Leu Thr Val
1               5                   10                  15

Leu Phe Ala Val Leu Thr Gly Ala Phe Met Leu Ile Gly Gly Ile Trp
            20                  25                  30

Leu Ala Thr Ile Gly Gly Ser Trp Tyr Tyr Ile Gly Gly Ala Ala
            35                  40                  45

Met Leu Leu Thr Ala Phe Leu Leu Trp Arg Arg Asn Ser Ala Ala Leu
50                  55                  60

Val Val Tyr Ala Leu Leu Leu Ala Thr Leu Ala Trp Gly Val Trp
65                  70                  75                  80

Glu Val Gly Thr Asp Phe Trp Ala Leu Ala Pro Arg Thr Asp Val Leu
                85                  90                  95

Val Ile Phe Gly Val Trp Leu Val Leu Pro Phe Val Tyr Arg Gly Leu
                100                 105                 110

Tyr Gln Pro Gly Lys Gly Ala Leu Gly Ala Met Gly Val Ala Leu Val
        115                 120                 125

Ala Ser Ala Ala Val Leu Thr Tyr Ser Val Phe Asn Asp Pro Gln Val
        130                 135                 140

Val Asn Gly Ala Leu Pro Ala Thr Ala Asp Asn Ala Pro Gln Ala Gln
145                 150                 155                 160

Pro Leu Ser Asn Ile Ala Asp Gly Asp Trp Pro Ala Tyr Ala Arg Asp
                165                 170                 175

Gln Gln Gly Thr Arg Phe Ser Pro Leu Lys Gln Ile Asn His Asp Asn
                180                 185                 190

Val Lys Glu Leu Gln Val Ala Trp Gln Phe Gln Thr Gly Asp Met Lys
        195                 200                 205

Arg Pro Ser Asp Pro Gly Glu Ile Thr Asp Glu Val Thr Pro Ile Lys
        210                 215                 220

Ile Arg Asp Thr Leu Tyr Leu Cys Thr Pro His Gln Ile Leu Phe Ala
225                 230                 235                 240

Leu Asp Ala Ala Thr Gly Lys Gln Lys Trp Lys Phe Asp Pro Gly Leu
                245                 250                 255

Lys Thr Asn Pro Thr Phe Gln His Val Thr Cys Arg Gly Val Ser Tyr
                260                 265                 270

His Glu Phe Pro Ala Ala Lys Asp Ala Ser Asn Thr Gln Pro Ala Leu
        275                 280                 285

Cys Ser Arg Arg Ile Tyr Leu Pro Val Asn Asp Gly Arg Leu Phe Ala
        290                 295                 300

Leu Asp Ala Glu Thr Gly Glu Arg Cys Pro Ala Phe Gly Asn Asn Gly
305                 310                 315                 320

Glu Leu Asp Leu Gln His Lys Gln Pro Val Thr Thr Pro Gly Met Tyr
                325                 330                 335

Glu Pro Thr Ser Pro Pro Val Ile Thr Asp Thr Thr Ile Val Met Ala
                340                 345                 350

Gly Ala Val Thr Asp Asn Phe Ser Thr Arg Glu Pro Ser Gly Ala Ile
        355                 360                 365

Arg Gly Phe Asp Val Asn Thr Gly Lys Leu Leu Trp Val Phe Asp Pro
        370                 375                 380

Gly Ala Lys Asp Pro Asn Ala Ile Pro Ala Asp Glu His Thr Phe Thr
385                 390                 395                 400

Met Asn Ser Pro Asn Ser Trp Ala Pro Ala Val Tyr Asp Pro Lys Leu
                405                 410                 415

Asp Ile Val Tyr Leu Pro Met Gly Val Thr Thr Pro Asp Ile Trp Gly
```

```
                420             425             430
Gly Asn Arg Thr Pro Glu Gln Glu Arg Tyr Ala Ser Ser Val Leu Ala
        435                 440                 445

Leu Asn Ala Thr Thr Gly Lys Leu Val Trp Ser Tyr Gln Thr Val His
    450                 455                 460

His Asp Leu Trp Asp Met Asp Leu Pro Ser Gln Pro Thr Leu Ala Asp
465                 470                 475                 480

Ile Thr Asp Lys Asp Gly Asn Thr Val Pro Val Ile Tyr Ala Pro Ala
                485                 490                 495

Lys Thr Gly Asn Ile Phe Val Leu Asp Arg Arg Thr Gly Lys Thr Val
            500                 505                 510

Val Pro Ala Pro Glu Thr Pro Val Pro Gln Gly Ala Ala Lys Gly Asp
        515                 520                 525

His Val Ser Ala Thr Gln Pro Tyr Ser Glu Leu Thr Phe Arg Pro Lys
    530                 535                 540

Gln Asn Leu Thr Asp Lys Asp Met Trp Gly Ala Thr Met Tyr Asp Gln
545                 550                 555                 560

Leu Val Cys Arg Val Ile Phe Lys Arg Leu Arg Tyr Glu Gly Pro Phe
                565                 570                 575

Thr Pro Pro Ser Glu Gln Gly Thr Leu Val Phe Pro Gly Asn Leu Gly
            580                 585                 590

Met Phe Glu Trp Gly Gly Ile Ser Val Asp Pro His Arg Gln Ile Ala
        595                 600                 605

Ile Ala Asn Pro Met Ala Leu Pro Phe Val Ser Lys Leu Ile Pro Arg
    610                 615                 620

Gly Pro Gly Asn Pro Glu Glu Pro Pro Lys Gly Ala Thr Gly Gly Ser
625                 630                 635                 640

Gly Thr Glu Thr Gly Ile Gln Pro Gln Tyr Gly Val Pro Tyr Gly Val
                645                 650                 655

Glu Leu Asn Pro Phe Leu Ser Pro Phe Gly Leu Pro Cys Lys Gln Pro
            660                 665                 670

Ala Trp Gly Tyr Val Ser Ala Val Asp Leu Lys Thr Asn Glu Val Val
        675                 680                 685

Trp Lys Gln Arg Ile Gly Thr Val Arg Asp Ser Ser Pro Val Pro Leu
    690                 695                 700

Pro Phe Lys Met Gly Met Pro Met Leu Gly Pro Val Ala Thr Ala
705                 710                 715                 720

Gly Lys Val Phe Phe Ile Gly Ala Thr Ala Asp Asn Tyr Leu Arg Ala
                725                 730                 735

Phe Ser Thr Asp Thr Gly Glu Leu Leu Trp Gln Ala Arg Leu Pro Ala
            740                 745                 750

Gly Gly Gln Ala Thr Pro Met Thr Tyr Glu Val Asn Gly Lys Gln Tyr
        755                 760                 765

Val Val Ile Ala Ala Gly His Gly Ser Phe Gly Thr Lys Leu Gly
    770                 775                 780

Asp Tyr Val Ile Ala Tyr Ala Leu Pro Asp Gln Lys
785                 790                 795

<210> SEQ ID NO 3
<211> LENGTH: 1308
<212> TYPE: DNA
<213> ORGANISM: Pantoea ananatis

<400> SEQUENCE: 3
atgagcagaa tcatgacgcc cgtgaactgg gaagcctgca gcagcgaggc gcagcaggcg      60
```

```
ctgttggcac gccctgcgct cgcctcgtct gacagcatca gccagatcgt gcgcgatgtg    120
ttggtcagag tgaaagagga aggcgatgcg gctttacgag aattcagcgc gcgctttgac    180
aaggttgaaa cagacgacct gcgcgttacg ccacagcaga tgcaggcggc cagcgatcgc    240
cttggtgacg agctgaaaca ggcgatggcc gtggccattg caatattga aacctttcac     300 cgtgcgcaga tcctgccgcc ggtggatgtg gaaacgcagc ccggcgtgcg ctgtcagcaa    360
attacgcgcc cgatgaaatc ggtgggcttg tatattccgg gcggttctgc cccgctgttt    420
tctaccgttc tgatgctggc taccccggcc cggattgcgg gctgtggtcg cgtggtgctg    480
tgctcgcccc cgccgattgc tgatgaaatt ctctacgcgg ccaaactttg cggtgtggaa    540
gaagtgttcc aggtgggtgg atcacaggcg attgccgccc tggcttttgg caccgaaagc    600
atccctaagg tagataaaat ttttggtccg ggcaacgcgt gggttaccga agccaaacgt    660
caggtcagcc agcgccttga tggcgcggcg attgatatgc ccgctggccc gtcggaagtg    720
ctggtgattg ccgatgaagg tgccacaccg gccttcgttg cctctgatct gctgtcgcag    780
gcggaacacg gcctgactc gcaggtgatt ttactgacgc cttcgctggc gctggccgag     840
cgcgtcgccg aggcggtgga ggatcagctg gcccagttgc cacgtgcggc gacagcccgc    900
caggcactgg aaagcagccg cctgatcgtc gcccgggata tgcagcaatg cattgcgatc    960
tccaaccgct atggtccgga gcacctgatt ctgcaaaccc gcacgccacg ggatctggtg    1020
gaacagatta ccagcgccgg ttcggttttc ctgggcgact ggtcaccgga atccgcagga    1080
gattatgctt cgggcaccaa ccacgtgctg ccgacctacg gctataccgc gacatgctcc    1140
agcctgggcc tggccgactt tcagaaacgc atgacggtac aggagctgac gccgcagggc    1200
ttcctgaacc tggcggcgac catcgaaacc ctggcggccg ctgaacagct gcacgcccac    1260
aaaaatgccg tcacgttgcg cgttgccgca ctcaaggagc aagcatga                1308
```

<210> SEQ ID NO 4
<211> LENGTH: 68
<212> TYPE: DNA
<213> ORGANISM: Artificial sequence
<220> FEATURE:
<223> OTHER INFORMATION: primer

<400> SEQUENCE: 4

```
ccatagcggt tggagatcgc aatgcattgc tgcatatccc tgaagcctgc ttttttatac    60
taagttgg                                                            68
```

<210> SEQ ID NO 5
<211> LENGTH: 68
<212> TYPE: DNA
<213> ORGANISM: Artificial sequence
<220> FEATURE:
<223> OTHER INFORMATION: primer

<400> SEQUENCE: 5

```
gcccgccagg cactggaaag cagccgcctg atcgtcgccc cgctcaagtt agtataaaaa    60
agctgaac                                                            68
```

<210> SEQ ID NO 6
<211> LENGTH: 33
<212> TYPE: DNA
<213> ORGANISM: Artificial sequence
<220> FEATURE:
<223> OTHER INFORMATION: primer

<400> SEQUENCE: 6

```
tagcgagatc tctgatgtcc ggcggtgctt ttg                          33
```

<210> SEQ ID NO 7
<211> LENGTH: 32
<212> TYPE: DNA
<213> ORGANISM: Artificial sequence
<220> FEATURE:
<223> OTHER INFORMATION: primer

<400> SEQUENCE: 7

```
aaaaagagct cttacgcccc gccctgccac tc                           32
```

<210> SEQ ID NO 8
<211> LENGTH: 34
<212> TYPE: DNA
<213> ORGANISM: Artificial sequence
<220> FEATURE:
<223> OTHER INFORMATION: primer

<400> SEQUENCE: 8

```
caggatctag aaggagacat gaacgatgaa catc                         34
```

<210> SEQ ID NO 9
<211> LENGTH: 36
<212> TYPE: DNA
<213> ORGANISM: Artificial sequence
<220> FEATURE:
<223> OTHER INFORMATION: primer

<400> SEQUENCE: 9

```
gataaggatc cgaaataaaa gaaaatgcca atagga                       36
```

<210> SEQ ID NO 10
<211> LENGTH: 31
<212> TYPE: DNA
<213> ORGANISM: Artificial sequence
<220> FEATURE:
<223> OTHER INFORMATION: primer

<400> SEQUENCE: 10

```
cctttgagct cgcgggcagt gagcgcaacg c                            31
```

<210> SEQ ID NO 11
<211> LENGTH: 48
<212> TYPE: DNA
<213> ORGANISM: Artificial sequence
<220> FEATURE:
<223> OTHER INFORMATION: primer

<400> SEQUENCE: 11

```
ctagagcggc cgccgatcgg gatcctcctg tgtgaaattg ttatccgc           48
```

<210> SEQ ID NO 12
<211> LENGTH: 42
<212> TYPE: DNA
<213> ORGANISM: Artificial sequence
<220> FEATURE:
<223> OTHER INFORMATION: primer

<400> SEQUENCE: 12

```
ctctacgatc gaggaggtta taaaaaatgg atattaatac tg                 42
```

<210> SEQ ID NO 13
<211> LENGTH: 36
<212> TYPE: DNA
<213> ORGANISM: Artificial sequence

```
<220> FEATURE:
<223> OTHER INFORMATION: primer

<400> SEQUENCE: 13
tcaaagcggc cgcttcttcg tctgtttcta ctggta                       36

<210> SEQ ID NO 14
<211> LENGTH: 31
<212> TYPE: DNA
<213> ORGANISM: Artificial sequence
<220> FEATURE:
<223> OTHER INFORMATION: primer

<400> SEQUENCE: 14
cctttggtac cgcgggcagt gagcgcaacg c                            31

<210> SEQ ID NO 15
<211> LENGTH: 34
<212> TYPE: DNA
<213> ORGANISM: Artificial sequence
<220> FEATURE:
<223> OTHER INFORMATION: primer

<400> SEQUENCE: 15
aacaggaatt ctttgcctgg cggcagtagc gcgg                         34

<210> SEQ ID NO 16
<211> LENGTH: 40
<212> TYPE: DNA
<213> ORGANISM: Artificial sequence
<220> FEATURE:
<223> OTHER INFORMATION: primer P1

<400> SEQUENCE: 16
ctagtaagat cttgaagcct gcttttttat actaagttgg                   40

<210> SEQ ID NO 17
<211> LENGTH: 41
<212> TYPE: DNA
<213> ORGANISM: Artificial sequence
<220> FEATURE:
<223> OTHER INFORMATION: primer P2

<400> SEQUENCE: 17
atgatcgaat tcgaaatcaa ataatgattt tattttgact g                 41

<210> SEQ ID NO 18
<211> LENGTH: 120
<212> TYPE: DNA
<213> ORGANISM: Artificial sequence
<220> FEATURE:
<223> OTHER INFORMATION: DNA fragment containing attL

<400> SEQUENCE: 18
agatcttgaa gcctgctttt ttatactaag ttggcattat aaaaaagcat tgcttatcaa    60
tttgttgcaa cgaacaggtc actatcagtc aaaataaaat cattatttga tttcgaattc   120

<210> SEQ ID NO 19
<211> LENGTH: 41
<212> TYPE: DNA
<213> ORGANISM: Artificial sequence
<220> FEATURE:
<223> OTHER INFORMATION: primer P3

<400> SEQUENCE: 19
atgccactgc agtctgttac aggtcactaa taccatctaa g                 41
```

```
<210> SEQ ID NO 20
<211> LENGTH: 46
<212> TYPE: DNA
<213> ORGANISM: Artificial sequence
<220> FEATURE:
<223> OTHER INFORMATION: primer P4

<400> SEQUENCE: 20
accgttaagc tttctagacg ctcaagttag tataaaaaag ctgaac          46

<210> SEQ ID NO 21
<211> LENGTH: 184
<212> TYPE: DNA
<213> ORGANISM: Artificial sequence
<220> FEATURE:
<223> OTHER INFORMATION: DNA fragment containing attR

<400> SEQUENCE: 21
ctgcagtctg ttacaggtca ctaataccat ctaagtagtt gattcatagt gactgcatat    60
gttgtgtttt acagtattat gtagtctgtt ttttatgcaa aatctaattt aatatattga   120
tatttatatc attttacgtt tctcgttcag cttttttata ctaacttgag cgtctagaaa   180
gctt                                                                 184

<210> SEQ ID NO 22
<211> LENGTH: 38
<212> TYPE: DNA
<213> ORGANISM: Artificial sequence
<220> FEATURE:
<223> OTHER INFORMATION: primer P5

<400> SEQUENCE: 22
ttcttagacg tcaggtggca cttttcgggg aaatgtgc                   38

<210> SEQ ID NO 23
<211> LENGTH: 37
<212> TYPE: DNA
<213> ORGANISM: Artificial sequence
<220> FEATURE:
<223> OTHER INFORMATION: primer P6

<400> SEQUENCE: 23
taacagagat ctcgcgcaga aaaaaggat ctcaaga                    37

<210> SEQ ID NO 24
<211> LENGTH: 46
<212> TYPE: DNA
<213> ORGANISM: Artificial sequence
<220> FEATURE:
<223> OTHER INFORMATION: primer P7

<400> SEQUENCE: 24
aacagagatc taagcttaga tcctttgcct ggcggcagta gcgcgg          46

<210> SEQ ID NO 25
<211> LENGTH: 35
<212> TYPE: DNA
<213> ORGANISM: Artificial sequence
<220> FEATURE:
<223> OTHER INFORMATION: primer P8

<400> SEQUENCE: 25
ataaactgca gcaaaaagag tttgtagaaa cgcaa                      35
```

```
<210> SEQ ID NO 26
<211> LENGTH: 1388
<212> TYPE: DNA
<213> ORGANISM: Artificial sequence
<220> FEATURE:
<223> OTHER INFORMATION: DNA fragment containing Tc gene and ter_thrL

<400> SEQUENCE: 26
gaattctcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
atatgcgttg atgcaatttc tatgcgcacc cgttctcgga gcactgtccg accgctttgg     300
ccgccgccca gtcctgctcg cttcgctact tggagccact atcgactacg cgatcatggc     360
gaccacaccc gtcctgtgga tcctctacgc cggacgcatc gtggccggca tcaccggcgc     420
cacaggtgcg gttgctggcg cctatatcgc cgacatcacc gatggggaag atcgggctcg     480
ccacttcggg ctcatgagcg cttgtttcgg cgtgggtatg gtggcaggcc ccgtggccgg     540
gggactgttg ggcgccatct ccttgcatgc accattcctt gcggcggcgg tgctcaacgg     600
cctcaaccta ctactgggct gcttcctaat gcaggagtcg cataagggag agcgtcgacc     660
gatgcccttg agagccttca acccagtcag ctccttccgg tgggcgcggg gcatgactat     720
cgtcgccgca cttatgactg tcttctttat catgcaactc gtaggacagg tgccggcagc     780
gctctgggtc attttcggcg aggaccgctt tcgctggagc gcgacgatga tcggcctgtc     840
gcttgcggta ttcggaatct tgcacgccct cgctcaagcc ttcgtcactg gtcccgccac     900
caaacgtttc ggcgagaagc aggccattat cgccggcatg gcggccgacg cgctgggcta     960
cgtcttgctg gcgttcgcga cgcgaggctg gatggccttc cccattatga ttcttctcgc    1020
ttccggcggc atcgggatgc ccgcgttgca ggccatgctg tccaggcagg tagatgacga    1080
ccatcaggga cagcttcaag atcgctcgc ggctcttacc agcctaactt cgatcactgg    1140
accgctgatc gtcacggcga tttatgccgc ctcggcgagc acatggaacg ggttggcatg    1200
gattgtaggc gccgccctat accttgtctg cctccccgcg ttgcgtcgcg gtgcatggag    1260
ccgggccacc tcgacctgaa tggaagccgg cggcacctcg ctaacggatt caccactcca    1320
actagaaagc ttaacacaga aaaaagcccg cacctgacag tgcgggcttt ttttttcgac    1380
cactgcag                                                             1388

<210> SEQ ID NO 27
<211> LENGTH: 36
<212> TYPE: DNA
<213> ORGANISM: Artificial sequence
<220> FEATURE:
<223> OTHER INFORMATION: primer P9

<400> SEQUENCE: 27
agtaattcta gaaagcttaa cacagaaaaa agcccg                                36

<210> SEQ ID NO 28
<211> LENGTH: 43
<212> TYPE: DNA
<213> ORGANISM: Artificial sequence
<220> FEATURE:
<223> OTHER INFORMATION: primer P10

<400> SEQUENCE: 28
ctagtaggat ccctgcagtg gtcgaaaaaa aaagcccgca ctg                         43
```

<210> SEQ ID NO 29
<211> LENGTH: 33
<212> TYPE: DNA
<213> ORGANISM: Artificial sequence
<220> FEATURE:
<223> OTHER INFORMATION: primer 1

<400> SEQUENCE: 29
ggaagatcta tttgccttcg cacatcaacc tgg            33

<210> SEQ ID NO 30
<211> LENGTH: 30
<212> TYPE: DNA
<213> ORGANISM: Artificial sequence
<220> FEATURE:
<223> OTHER INFORMATION: primer 2

<400> SEQUENCE: 30
cggggtacct tgtaaatatt ttaacccgcc            30

<210> SEQ ID NO 31
<211> LENGTH: 56
<212> TYPE: DNA
<213> ORGANISM: Artificial sequence
<220> FEATURE:
<223> OTHER INFORMATION: primer 3

<400> SEQUENCE: 31
ggaagatcta aggagacctt aaatgagcga cacaacgatc ctgcaaaaca gtaccc            56

<210> SEQ ID NO 32
<211> LENGTH: 39
<212> TYPE: DNA
<213> ORGANISM: Artificial sequence
<220> FEATURE:
<223> OTHER INFORMATION: primer 4

<400> SEQUENCE: 32
cggggtacct cgtagaggtt tactggcgct tatccagcg            39

<210> SEQ ID NO 33
<211> LENGTH: 80
<212> TYPE: DNA
<213> ORGANISM: Artificial sequence
<220> FEATURE:
<223> OTHER INFORMATION: primer

<400> SEQUENCE: 33
ctatctgatt gttttcctga gttttctggc aacgaaatga ggtcaacatt tgaagcctgc            60 tttttttatac taagttggca            80

<210> SEQ ID NO 34
<211> LENGTH: 80
<212> TYPE: DNA
<213> ORGANISM: Artificial sequence
<220> FEATURE:
<223> OTHER INFORMATION: primer

<400> SEQUENCE: 34
agcaggcata aaaaaaggcg gaccggagtc cgcctctgtt caggtgttaa cgctcaagtt            60
agtataaaaa agctgaacga            80

<210> SEQ ID NO 35
<211> LENGTH: 21

-continued

```
<212> TYPE: DNA
<213> ORGANISM: Artificial sequence
<220> FEATURE:
<223> OTHER INFORMATION: primer

<400> SEQUENCE: 35
gatatggatc atcacgcttc a                                              21

<210> SEQ ID NO 36
<211> LENGTH: 18
<212> TYPE: DNA
<213> ORGANISM: Artificial sequence
<220> FEATURE:
<223> OTHER INFORMATION: primer

<400> SEQUENCE: 36
catgctcggc tattcgac                                                  18

<210> SEQ ID NO 37
<211> LENGTH: 1422
<212> TYPE: DNA
<213> ORGANISM: Escherichia coli
<220> FEATURE:
<221> NAME/KEY: CDS
<222> LOCATION: (301)..(1119)

<400> SEQUENCE: 37
tcggtcaggg catggatgta caaagcgcgc aggagaagat tggtcaggtg gtggaaggct     60
accgcaatac gaaagaagtc cgcgaactgg cgcatcgctt cggcgttgaa atgccaataa   120
ccgaggaaat ttatcaagta ttatattgcg gaaaaaacgc gcgcgaggca gcattgactt   180
tactaggtcg tgcacgcaag gacgagcgca gcagccacta accccaggga acctttgtta   240
ccgctatgac ccggcccgcg cagaacgggc cggtcattat ctcatcgtgt ggagtaagca   300 atg tcg tgt gaa gaa ctg gaa att gtc tgg aac aat att aaa gcc gaa   348
Met Ser Cys Glu Glu Leu Glu Ile Val Trp Asn Asn Ile Lys Ala Glu
  1               5                  10                  15 gcc aga acg ctg gcg gac tgt gag cca atg ctg gcc agt ttt tac cac   396
Ala Arg Thr Leu Ala Asp Cys Glu Pro Met Leu Ala Ser Phe Tyr His
             20                  25                  30 gcg acg cta ctc aag cac gaa aac ctt ggc agt gca ctg agc tac atg   444
Ala Thr Leu Leu Lys His Glu Asn Leu Gly Ser Ala Leu Ser Tyr Met
         35                  40                  45 ctg gcg aac aag ctg tca tcg cca att atg cct gct att gct atc cgt   492
Leu Ala Asn Lys Leu Ser Ser Pro Ile Met Pro Ala Ile Ala Ile Arg
     50                  55                  60 gaa gtg gtg gaa gaa gcc tac gcc gct gac ccg gaa atg atc gcc tct   540
Glu Val Val Glu Glu Ala Tyr Ala Ala Asp Pro Glu Met Ile Ala Ser
 65                  70                  75                  80 gcg gcc tgt gat att cag gcg gtg cgt acc cgc gac ccg gca gtc gat   588
Ala Ala Cys Asp Ile Gln Ala Val Arg Thr Arg Asp Pro Ala Val Asp
                 85                  90                  95 aaa tac tca acc ccg ttg tta tac ctg aag ggt ttt cat gcc ttg cag   636
Lys Tyr Ser Thr Pro Leu Leu Tyr Leu Lys Gly Phe His Ala Leu Gln
            100                 105                 110 gcc tat cgc atc ggt cac tgg ttg tgg aat cag ggg cgt cgc gca ctg   684
Ala Tyr Arg Ile Gly His Trp Leu Trp Asn Gln Gly Arg Arg Ala Leu
        115                 120                 125 gca atc ttt ctg caa aac cag gtt tct gtg acg ttc cag gtc gat att   732
Ala Ile Phe Leu Gln Asn Gln Val Ser Val Thr Phe Gln Val Asp Ile
    130                 135                 140 cac ccg gca gca aaa att ggt cgc ggt atc atg ctt gac cac gcg aca   780
His Pro Ala Ala Lys Ile Gly Arg Gly Ile Met Leu Asp His Ala Thr
```

```
                    145                 150                 155                 160
ggc atc gtc gtt ggt gaa acg gcg gtg att gaa aac gac gta tcg att          828
Gly Ile Val Val Gly Glu Thr Ala Val Ile Glu Asn Asp Val Ser Ile
                165                 170                 175 ctg caa tct gtg acg ctt ggc ggt acg ggt aaa tct ggt ggt gac cgt          876
Leu Gln Ser Val Thr Leu Gly Gly Thr Gly Lys Ser Gly Gly Asp Arg
            180                 185                 190 cac ccg aaa att cgt gaa ggt gtg atg att ggc gcg ggc gcg aaa atc          924
His Pro Lys Ile Arg Glu Gly Val Met Ile Gly Ala Gly Ala Lys Ile
        195                 200                 205 ctc ggc aat att gaa gtt ggg cgc ggc gcg aag att ggc gca ggt tcc          972
Leu Gly Asn Ile Glu Val Gly Arg Gly Ala Lys Ile Gly Ala Gly Ser
    210                 215                 220 gtg gtg ctg caa ccg gtg ccg ccg cat acc acc gcc gct ggc gtt ccg         1020
Val Val Leu Gln Pro Val Pro Pro His Thr Thr Ala Ala Gly Val Pro
225                 230                 235                 240 gct cgt att gtc ggt aaa cca gac agc gat aag cca tca atg gat atg         1068
Ala Arg Ile Val Gly Lys Pro Asp Ser Asp Lys Pro Ser Met Asp Met
                245                 250                 255 gac cag cat ttc aac ggt att aac cat aca ttt gag tat ggg gat ggg         1116
Asp Gln His Phe Asn Gly Ile Asn His Thr Phe Glu Tyr Gly Asp Gly
            260                 265                 270 atc taatgtcctg tgatcgtgcc ggatgcgatg taatcatcta tccggcctac             1169
Ile agtaactaat ctctcaatac cgctcccgga taccccaact gccgccaggc ttcatacacc      1229
actaccgaca ccgcattgga cagattcatg ctgcggctgt ccggcaccat cggaatgcga      1289
attttttgtt cagcgggcag ggcatcaaga atgctcgctg gcaggccgcg tgtttccggg      1349
ccgaacatca gataatcgcc atcctgatag cttacggcgc tgtgagcagg tgtacctttc      1409
gtggtgaggg cga                                                         1422

<210> SEQ ID NO 38
<211> LENGTH: 273
<212> TYPE: PRT
<213> ORGANISM: Escherichia coli

<400> SEQUENCE: 38

Met Ser Cys Glu Glu Leu Glu Ile Val Trp Asn Asn Ile Lys Ala Glu
1               5                   10                  15

Ala Arg Thr Leu Ala Asp Cys Glu Pro Met Leu Ala Ser Phe Tyr His
            20                  25                  30

Ala Thr Leu Leu Lys His Glu Asn Leu Gly Ser Ala Leu Ser Tyr Met
        35                  40                  45

Leu Ala Asn Lys Leu Ser Ser Pro Ile Met Pro Ala Ile Ala Ile Arg
    50                  55                  60

Glu Val Val Glu Glu Ala Tyr Ala Ala Asp Pro Glu Met Ile Ala Ser
65                  70                  75                  80

Ala Ala Cys Asp Ile Gln Ala Val Arg Thr Arg Asp Pro Ala Val Asp
                85                  90                  95

Lys Tyr Ser Thr Pro Leu Leu Tyr Leu Lys Gly Phe His Ala Leu Gln
            100                 105                 110

Ala Tyr Arg Ile Gly His Trp Leu Trp Asn Gln Gly Arg Arg Ala Leu
        115                 120                 125

Ala Ile Phe Leu Gln Asn Gln Val Ser Val Thr Phe Gln Val Asp Ile
    130                 135                 140

His Pro Ala Ala Lys Ile Gly Arg Gly Ile Met Leu Asp His Ala Thr
145                 150                 155                 160
```

```
Gly Ile Val Val Gly Glu Thr Ala Val Ile Glu Asn Asp Val Ser Ile
                165                 170                 175

Leu Gln Ser Val Thr Leu Gly Thr Gly Lys Ser Gly Gly Asp Arg
            180                 185                 190

His Pro Lys Ile Arg Glu Gly Val Met Ile Gly Ala Gly Lys Ile
            195                 200                 205

Leu Gly Asn Ile Glu Val Gly Arg Gly Ala Lys Ile Gly Ala Gly Ser
    210                 215                 220

Val Val Leu Gln Pro Val Pro Pro His Thr Thr Ala Ala Gly Val Pro
225                 230                 235                 240

Ala Arg Ile Val Gly Lys Pro Asp Ser Asp Lys Pro Ser Met Asp Met
                245                 250                 255

Asp Gln His Phe Asn Gly Ile Asn His Thr Phe Glu Tyr Gly Asp Gly
                260                 265                 270

Ile

<210> SEQ ID NO 39
<211> LENGTH: 1039
<212> TYPE: DNA
<213> ORGANISM: Escherichia coli
<220> FEATURE:
<221> NAME/KEY: CDS
<222> LOCATION: (201)..(839)

<400> SEQUENCE: 39
tgcggataac ggtagaattt ttacgccagt attttgccga gcactacccg aattttttcac      60 tggagcatgc ctgattaatg attcaattat cgggttgata tcaggttaaa acctgatttt    120
ctcctttcta agccgctaca gattggttag catattcacc tttaatcgcg catgatcgaa    180
agataattaa agaggttaat gtg ttc gct gaa tac ggg gtt ctg aat tac tgg   233
                      Val Phe Ala Glu Tyr Gly Val Leu Asn Tyr Trp
                        1               5                  10 acc tat ctg gtt ggg gcc att ttt att gtg ttg gtg cca ggg cca aat   281
Thr Tyr Leu Val Gly Ala Ile Phe Ile Val Leu Val Pro Gly Pro Asn
            15                  20                  25 acc ctg ttt gta ctc aaa aat agc gtc agt agc ggt atg aaa ggc ggt   329
Thr Leu Phe Val Leu Lys Asn Ser Val Ser Ser Gly Met Lys Gly Gly
        30                  35                  40 tat ctt gcg gcc tgc ggt gta ttt att ggc gat gcg gta ttg atg ttt   377
Tyr Leu Ala Ala Cys Gly Val Phe Ile Gly Asp Ala Val Leu Met Phe
    45                  50                  55 ctg gca tgg gct gga gtg gcg aca tta att aag acc acc ccg ata tta   425
Leu Ala Trp Ala Gly Val Ala Thr Leu Ile Lys Thr Thr Pro Ile Leu
60                  65                  70                  75 ttc aac att gta cgt tat ctt ggt gcg ttt tat ttg ctc tat ctg ggg   473
Phe Asn Ile Val Arg Tyr Leu Gly Ala Phe Tyr Leu Leu Tyr Leu Gly
                80                  85                  90 agt aaa att ctt tac gcg acc ctg aag ggt aaa aat agc gag gcc aaa   521
Ser Lys Ile Leu Tyr Ala Thr Leu Lys Gly Lys Asn Ser Glu Ala Lys
            95                 100                 105 tcc gat gag ccc caa tac ggt gct att ttt aaa cgc gcg tta att ttg   569
Ser Asp Glu Pro Gln Tyr Gly Ala Ile Phe Lys Arg Ala Leu Ile Leu
        110                 115                 120 agc ctg act aat ccg aaa gcc att ttg ttc tat gtg tcg ttt ttc gta   617
Ser Leu Thr Asn Pro Lys Ala Ile Leu Phe Tyr Val Ser Phe Phe Val
    125                 130                 135 cag ttt atc gat gtt aat gcc cca cat acg gga att tca ttc ttt att   665
Gln Phe Ile Asp Val Asn Ala Pro His Thr Gly Ile Ser Phe Phe Ile
140                 145                 150                 155
```

```
ctg gcg gcg acg ctg gaa ctg gtg agt ttc tgc tat ttg agc ttc ctg      713
Leu Ala Ala Thr Leu Glu Leu Val Ser Phe Cys Tyr Leu Ser Phe Leu
            160                 165                 170 att ata tct ggt gct ttt gtc acg cag tac ata cgt acc aaa aag aaa      761
Ile Ile Ser Gly Ala Phe Val Thr Gln Tyr Ile Arg Thr Lys Lys Lys
        175                 180                 185 ctg gct aaa gtt ggc aac tca ctg att ggt ttg atg ttc gtg ggt ttc      809
Leu Ala Lys Val Gly Asn Ser Leu Ile Gly Leu Met Phe Val Gly Phe
    190                 195                 200 gct gcc cga ctg gcg acg ctg caa tcc tga tgctttcagc ccgcgttgtc        859
Ala Ala Arg Leu Ala Thr Leu Gln Ser
205                 210 gcgggcttcc catctataat cctccctgat tcttcgctga tatggtgcta aaaagtaacc    919
aataaatggt atttaaaatg caaattatca ggcgtaccct gaaacggctg aataaaccg     979 ttttcagcgc attaccgaa ggagggaaaa ggatgcttca atcccacag aattatattc     1039

<210> SEQ ID NO 40
<211> LENGTH: 212
<212> TYPE: PRT
<213> ORGANISM: Escherichia coli

<400> SEQUENCE: 40

Val Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Phe Val Leu
            20                  25                  30

Lys Asn Ser Val Ser Ser Gly Met Lys Gly Gly Tyr Leu Ala Ala Cys
        35                  40                  45

Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Phe Ile Leu Ala Ala Thr Leu
145                 150                 155                 160

Glu Leu Val Ser Phe Cys Tyr Leu Ser Phe Leu Ile Ile Ser Gly Ala
                165                 170                 175

Phe Val Thr Gln Tyr Ile Arg Thr Lys Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210

<210> SEQ ID NO 41
<211> LENGTH: 313
<212> TYPE: DNA
<213> ORGANISM: Escherichia coli

<400> SEQUENCE: 41
```

-continued

```
gcatgcttcc aactgcgcta atgacgcagc tggacgaagg cgggattctc gtcttacccg      60 tagggagga gcaccagtat ttgaaacggg tgcgtcgtcg gggaggcgaa tttattatcg     120
ataccgtgga ggccgtgcgc tttgtcccct tagtgaaggg tgagctggct aaaacgtga    180 ggaaatacct ggatttttcc tggttatttt gccgcaggtc agcgtatcgt gaacatcttt     240
tccagtgttc agtagggtgc cttgcacggt aattatgtca ctggttatta accaattttt     300
cctgggggtc gac                                                       313

<210> SEQ ID NO 42
<211> LENGTH: 312
<212> TYPE: DNA
<213> ORGANISM: Artificial Sequence
<220> FEATURE:
<223> OTHER INFORMATION: mutant nlpD promoter

<400> SEQUENCE: 42
gcatgcttcc aactgcgcta atgacgcagc tggacgaagg cgggattctc gtcttacccg      60 tagggagga gcaccagtat ttgaaacggg tgcgtcgtcg gggaggcgaa tttattatcg     120
ataccgtgga ggccgtgcgc tttgtcccct tagtgaaggg tgagctggct aaaacgtga    180 ggaaatacct ggatttttcc tggttatttt gccgcaggtc agcgtataat gaagatcttt     240
tccagtgttg acaagggtcc ttgcacggtt ataatgtcac tggttattaa ccaatttttc     300 ctggggggtcg ac                                                      312

<210> SEQ ID NO 43
<211> LENGTH: 4403
<212> TYPE: DNA
<213> ORGANISM: Pantoea ananatis
<220> FEATURE:
<221> NAME/KEY: CDS
<222> LOCATION: (301)..(1311)
<220> FEATURE:
<221> NAME/KEY: CDS
<222> LOCATION: (1317)..(2147)
<220> FEATURE:
<221> NAME/KEY: CDS
<222> LOCATION: (2150)..(3022)

<400> SEQUENCE: 43
tacagcggaa cctggcacgg gccagaaggg ttgatgccgt cggatgacac actcaagagc      60
tggacgctca gcaaaattgt ctggcagcgc taagtctttt ttcacaccgc tcaaccgcag    120
ggcataaccg gccctgcgcg tccaattctg tttttcgtct gtcttttccc gccgccttat    180 gccttttttcg actttgaaat cagcaaacga tatataaaac cgttacgggt ttacgctgag    240
ttataaataa actgctgtat ctgcagatga gatctgcatc aaatttcctc agggtgaacc    300
```

| | | | | | | | | | | | | | | | | |
|---|---|---|---|---|---|---|---|---|---|---|---|---|---|---|---|---|
| atg | acc | tta | cca | gcg | atg | aaa | aaa | atc | gtg | agc | gga | ctc | gca | ctg | tcg | 348 |
| Met | Thr | Leu | Pro | Ala | Met | Lys | Lys | Ile | Val | Ser | Gly | Leu | Ala | Leu | Ser | |
| 1 | | | | 5 | | | | | 10 | | | | | 15 | | |

| ctg | agt | ctg | gcc | ggt | gcc | gca | aac | gcg | acc | gag | ctg | ttg | aac | agc | tct | 396 |
|---|---|---|---|---|---|---|---|---|---|---|---|---|---|---|---|---|
| Leu | Ser | Leu | Ala | Gly | Ala | Ala | Asn | Ala | Thr | Glu | Leu | Leu | Asn | Ser | Ser | |
| | | | 20 | | | | | 25 | | | | | 30 | | | |

| tac | gat | gtc | gca | cgt | gaa | tta | ttt | gtc | gcc | ctg | aat | gcg | cct | ttt | gtc | 444 |
|---|---|---|---|---|---|---|---|---|---|---|---|---|---|---|---|---|
| Tyr | Asp | Val | Ala | Arg | Glu | Leu | Phe | Val | Ala | Leu | Asn | Ala | Pro | Phe | Val | |
| | | 35 | | | | | 40 | | | | | 45 | | | | |

| agc | cag | tgg | gat | gcc | agc | cat | cct | gac | gac | aag | ctg | acc | att | aag | atg | 492 |
|---|---|---|---|---|---|---|---|---|---|---|---|---|---|---|---|---|
| Ser | Gln | Trp | Asp | Ala | Ser | His | Pro | Asp | Asp | Lys | Leu | Thr | Ile | Lys | Met | |
| 50 | | | | | 55 | | | | | 60 | | | | | | |

| tcc | cat | gcc | ggg | tca | tcc | aaa | cag | gcg | ctg | gcg | atc | ctg | caa | ggc | ctg | 540 |
|---|---|---|---|---|---|---|---|---|---|---|---|---|---|---|---|---|
| Ser | His | Ala | Gly | Ser | Ser | Lys | Gln | Ala | Leu | Ala | Ile | Leu | Gln | Gly | Leu | |

-continued

| | | |
|---|---|---|
| 65 70 75 80 | | |
| cgt gcc gat gtg gtg acc tat aac cag gtc acc gat gtg cag gtg ctg<br>Arg Ala Asp Val Val Thr Tyr Asn Gln Val Thr Asp Val Gln Val Leu<br>85 90 95 | 588 | |
| cac gat aaa ggc aaa ctg atc cct gcc gac tgg caa acc cgc ctg ccg<br>His Asp Lys Gly Lys Leu Ile Pro Ala Asp Trp Gln Thr Arg Leu Pro<br>100 105 110 | 636 | |
| aat aac agt tcg ccg ttt tac tcc acc atg gcg ttc ctg gtg cgc aag<br>Asn Asn Ser Ser Pro Phe Tyr Ser Thr Met Ala Phe Leu Val Arg Lys<br>115 120 125 | 684 | |
| gga aac cca aag cag att cac gac tgg tcc gat tta acc cgt gac gat<br>Gly Asn Pro Lys Gln Ile His Asp Trp Ser Asp Leu Thr Arg Asp Asp<br>130 135 140 | 732 | |
| gtg aag ctg att ttt cct aat ccc aaa acc tcg ggc aac gga cgt tat<br>Val Lys Leu Ile Phe Pro Asn Pro Lys Thr Ser Gly Asn Gly Arg Tyr<br>145 150 155 160 | 780 | |
| acc tat ctt gct gcc tgg ggc gcc gcc agc aac act gac ggg ggc gat<br>Thr Tyr Leu Ala Ala Trp Gly Ala Ala Ser Asn Thr Asp Gly Gly Asp<br>165 170 175 | 828 | |
| cag gct aaa acc cgc gct ttt atg aca aaa ttt ctg aaa aat gtt gaa<br>Gln Ala Lys Thr Arg Ala Phe Met Thr Lys Phe Leu Lys Asn Val Glu<br>180 185 190 | 876 | |
| gtc ttc gat acc ggt ggc cga ggt gct acg acc acc ttt gct gaa cgc<br>Val Phe Asp Thr Gly Gly Arg Gly Ala Thr Thr Thr Phe Ala Glu Arg<br>195 200 205 | 924 | |
| ggt ctg ggc gat gtg ttg atc agt ttt gag tct gaa gtg aat aac atc<br>Gly Leu Gly Asp Val Leu Ile Ser Phe Glu Ser Glu Val Asn Asn Ile<br>210 215 220 | 972 | |
| cgc aac cag tac ggc aaa gac gac tac gaa gtc gtg gtg cct aaa acc<br>Arg Asn Gln Tyr Gly Lys Asp Asp Tyr Glu Val Val Val Pro Lys Thr<br>225 230 235 240 | 1020 | |
| gat att ctc gcg gag ttt ccc gtt gcc tgg gta gat aaa aac gtc gag<br>Asp Ile Leu Ala Glu Phe Pro Val Ala Trp Val Asp Lys Asn Val Glu<br>245 250 255 | 1068 | |
| cag aat aaa aca gcc gat gca gcg aaa gcc tat ctg acc tgg ctg tat<br>Gln Asn Lys Thr Ala Asp Ala Ala Lys Ala Tyr Leu Thr Trp Leu Tyr<br>260 265 270 | 1116 | |
| tct cct gcg gcg cag aaa att att acg gat ttc tat tac cgc gtg aac<br>Ser Pro Ala Ala Gln Lys Ile Ile Thr Asp Phe Tyr Tyr Arg Val Asn<br>275 280 285 | 1164 | |
| aat ccg cag tta atg gcg cag caa aaa gcc cgt ttt cct gcc acg aac<br>Asn Pro Gln Leu Met Ala Gln Gln Lys Ala Arg Phe Pro Ala Thr Asn<br>290 295 300 | 1212 | |
| ctg ttt cgt gtt gaa gac att ttt ggc ggc tgg gat aac gtg atg aaa<br>Leu Phe Arg Val Glu Asp Ile Phe Gly Gly Trp Asp Asn Val Met Lys<br>305 310 315 320 | 1260 | |
| acc cat ttc gcc agc ggt ggc gag cta gac cag tta tta gcg gcg ggg<br>Thr His Phe Ala Ser Gly Gly Glu Leu Asp Gln Leu Leu Ala Ala Gly<br>325 330 335 | 1308 | |
| cgg tgatc atg ttt gca gcc agc caa aaa cgc gtc ctg ccc ggt ttc ggt<br>Arg Met Phe Ala Ala Ser Gln Lys Arg Val Leu Pro Gly Phe Gly<br>340 345 350 | 1358 | |
| ctc agc ctg ggc acc agc ctg ctc ttt acc tgt ctg gtg ctg ctg ctg<br>Leu Ser Leu Gly Thr Ser Leu Leu Phe Thr Cys Leu Val Leu Leu Leu<br>355 360 365 | 1406 | |
| cca atc agc gca ctg att atg cag ctg tcg cag atg acg ttg cag caa<br>Pro Ile Ser Ala Leu Ile Met Gln Leu Ser Gln Met Thr Leu Gln Gln<br>370 375 380 | 1454 | |
| tac tgg gac gtg gtc acc aat ccg cag ctc atc gcg gcc tat aag gtc<br>Tyr Trp Asp Val Val Thr Asn Pro Gln Leu Ile Ala Ala Tyr Lys Val | 1502 | |

|   |   |   |   |   |   |   |   |   |   |   |   |   |   |   |   |   |
|---|---|---|---|---|---|---|---|---|---|---|---|---|---|---|---|---|
|   |   | 385 |   |   |   |   | 390 |   |   |   |   | 395 |   |   |   |   |
| acg | ctg | ctg | tcg | gcc | ggt | gtg | gcc | tca | ctg | ttt | aat | gcc | gta | ttc | ggc | 1550 |
| Thr | Leu | Leu | Ser | Ala | Gly | Val | Ala | Ser | Leu | Phe | Asn | Ala | Val | Phe | Gly |   |
| 400 |   |   |   |   | 405 |   |   |   |   | 410 |   |   |   |   | 415 |   |
| atg | tta | atg | gcg | tgg | atc | tta | acg | cgt | tac | cgt | ttt | ccg | ggc | cgc | acg | 1598 |
| Met | Leu | Met | Ala | Trp | Ile | Leu | Thr | Arg | Tyr | Arg | Phe | Pro | Gly | Arg | Thr |   |
|   |   |   |   | 420 |   |   |   |   | 425 |   |   |   |   | 430 |   |   |
| ctg | ctc | gat | ggt | ctg | atg | gat | ctg | ccg | ttt | gcg | ctg | ccg | acc | gcg | gtt | 1646 |
| Leu | Leu | Asp | Gly | Leu | Met | Asp | Leu | Pro | Phe | Ala | Leu | Pro | Thr | Ala | Val |   |
|   |   |   | 435 |   |   |   |   | 440 |   |   |   |   | 445 |   |   |   |
| gct | ggc | ctg | acg | ctg | gcc | ggt | ctg | ttt | tcc | gtg | aac | ggc | tgg | tac | gga | 1694 |
| Ala | Gly | Leu | Thr | Leu | Ala | Gly | Leu | Phe | Ser | Val | Asn | Gly | Trp | Tyr | Gly |   |
|   |   | 450 |   |   |   |   | 455 |   |   |   |   | 460 |   |   |   |   |
| caa | tgg | ttc | gcg | cat | ttt | gat | atc | aag | atc | tcc | tat | acc | tgg | atc | ggt | 1742 |
| Gln | Trp | Phe | Ala | His | Phe | Asp | Ile | Lys | Ile | Ser | Tyr | Thr | Trp | Ile | Gly |   |
| 465 |   |   |   |   | 470 |   |   |   |   | 475 |   |   |   |   |   |   |
| atc | gcg | ctc | gcg | atg | gcc | ttc | acc | agt | att | ccg | ttt | gtg | gtg | cgt | acc | 1790 |
| Ile | Ala | Leu | Ala | Met | Ala | Phe | Thr | Ser | Ile | Pro | Phe | Val | Val | Arg | Thr |   |
| 480 |   |   |   |   | 485 |   |   |   |   | 490 |   |   |   |   | 495 |   |
| gtg | cag | ccg | gtg | ctg | gaa | gag | ctg | ggg | cct | gaa | tat | gag | gaa | gcg | gct | 1838 |
| Val | Gln | Pro | Val | Leu | Glu | Glu | Leu | Gly | Pro | Glu | Tyr | Glu | Glu | Ala | Ala |   |
|   |   |   |   | 500 |   |   |   |   | 505 |   |   |   |   | 510 |   |   |
| caa | acg | ctg | ggc | gcc | acg | ccc | tgg | cag | agc | ttc | cgc | gg | gtc | gtt | ctg | 1886 |
| Gln | Thr | Leu | Gly | Ala | Thr | Pro | Trp | Gln | Ser | Phe | Arg | Arg | Val | Val | Leu |   |
|   |   |   | 515 |   |   |   |   | 520 |   |   |   |   | 525 |   |   |   |
| cct | gaa | gtg | gca | ccg | gcc | tta | ctt | gcg | ggc | acc | gcg | ctg | tcg | ttt | acc | 1934 |
| Pro | Glu | Val | Ala | Pro | Ala | Leu | Leu | Ala | Gly | Thr | Ala | Leu | Ser | Phe | Thr |   |
|   |   | 530 |   |   |   |   | 535 |   |   |   |   | 540 |   |   |   |   |
| cgc | agc | ctg | ggc | gag | ttt | ggt | gcg | gta | atc | ttt | att | gcc | ggc | aac | atc | 1982 |
| Arg | Ser | Leu | Gly | Glu | Phe | Gly | Ala | Val | Ile | Phe | Ile | Ala | Gly | Asn | Ile |   |
| 545 |   |   |   |   | 550 |   |   |   |   | 555 |   |   |   |   |   |   |
| gct | tgg | aaa | acc | gaa | gtg | acc | tcg | ctg | atg | atc | ttc | gtg | cgc | ctg | cag | 2030 |
| Ala | Trp | Lys | Thr | Glu | Val | Thr | Ser | Leu | Met | Ile | Phe | Val | Arg | Leu | Gln |   |
| 560 |   |   |   |   | 565 |   |   |   |   | 570 |   |   |   |   | 575 |   |
| gag | ttt | gac | tat | ccg | gca | gcc | agc | gcc | att | gcc | tcg | gtc | att | ctg | gcg | 2078 |
| Glu | Phe | Asp | Tyr | Pro | Ala | Ala | Ser | Ala | Ile | Ala | Ser | Val | Ile | Leu | Ala |   |
|   |   |   |   | 580 |   |   |   |   | 585 |   |   |   |   | 590 |   |   |
| gca | tca | ctg | ctg | tta | ctt | ttc | gct | atc | aat | acc | tta | caa | agc | cgc | ttt | 2126 |
| Ala | Ser | Leu | Leu | Leu | Leu | Phe | Ala | Ile | Asn | Thr | Leu | Gln | Ser | Arg | Phe |   |
|   |   |   | 595 |   |   |   |   | 600 |   |   |   |   | 605 |   |   |   |
| ggt | cgt | cgt | ctg | gga | ggc | cat | ta | atg | gca | gag | att | tcg | caa | ctc | aat | 2173 |
| Gly | Arg | Arg | Leu | Gly | Gly | His |   | Met | Ala | Glu | Ile | Ser | Gln | Leu | Asn |   |
|   |   | 610 |   |   |   |   |   |   | 615 |   |   |   |   | 620 |   |   |
| cat | gcc | gac | cgc | cag | cct | gtt | aac | tgg | gcc | aag | tgg | ctg | ctt | att | ggt | 2221 |
| His | Ala | Asp | Arg | Gln | Pro | Val | Asn | Trp | Ala | Lys | Trp | Leu | Leu | Ile | Gly |   |
|   |   | 625 |   |   |   |   | 630 |   |   |   |   | 635 |   |   |   |   |
| att | ggt | gcg | ctg | ata | tcc | ttg | ctg | ctg | gtc | gtg | ccg | atg | gtg | tcc |   | 2269 |
| Ile | Gly | Ala | Leu | Ile | Ser | Leu | Leu | Leu | Val | Val | Pro | Met | Val | Ser |   |   |
| 640 |   |   |   |   | 645 |   |   |   |   | 650 |   |   |   |   |   |   |
| atc | ttc | tgg | gag | gcc | ctg | cat | aaa | gga | ctg | ggc | gtc | acc | tta | agt | aat | 2317 |
| Ile | Phe | Trp | Glu | Ala | Leu | His | Lys | Gly | Leu | Gly | Val | Thr | Leu | Ser | Asn |   |
| 655 |   |   |   |   | 660 |   |   |   |   | 665 |   |   |   |   | 670 |   |
| ctg | acc | gac | agc | gac | atg | ctc | cat | gcc | ata | tgg | ctc | acg | gtg | ctg | gtc | 2365 |
| Leu | Thr | Asp | Ser | Asp | Met | Leu | His | Ala | Ile | Trp | Leu | Thr | Val | Leu | Val |   |
|   |   |   |   | 675 |   |   |   |   | 680 |   |   |   |   | 685 |   |   |
| gca | ttg | att | acc | gtg | ccg | gtg | aat | tta | gtg | ttc | ggc | acg | ctg | ctg | gcc | 2413 |
| Ala | Leu | Ile | Thr | Val | Pro | Val | Asn | Leu | Val | Phe | Gly | Thr | Leu | Leu | Ala |   |
|   |   |   | 690 |   |   |   |   | 695 |   |   |   |   | 700 |   |   |   |
| tgg | ctg | gtg | aca | cgc | ttt | acc | ttt | ccg | gga | cgt | cag | ctg | ctt | ttg | acg | 2461 |
| Trp | Leu | Val | Thr | Arg | Phe | Thr | Phe | Pro | Gly | Arg | Gln | Leu | Leu | Leu | Thr |   |

|  |  |
|---|---:|
| ctg ttc gat att ccc ttt gcg gta tcg cct gtg gtc gcc ggt ctg atg<br>Leu Phe Asp Ile Pro Phe Ala Val Ser Pro Val Val Ala Gly Leu Met<br>720                          725                      730 | 2509 |
| tat ctc ctg ttc tgg ggc att aac ggc ccg gcg ggc ggc tgg ctg gat<br>Tyr Leu Leu Phe Trp Gly Ile Asn Gly Pro Ala Gly Gly Trp Leu Asp<br>735                          740                      745                750 | 2557 |
| gcc cat aat att cag gtg atg ttc tcc tgg cct ggc atg gtg ctg gtc<br>Ala His Asn Ile Gln Val Met Phe Ser Trp Pro Gly Met Val Leu Val<br>                        755                      760                      765 | 2605 |
| acc gtc ttc gtt acc tgt ccg ttt gtg gtg cgc gaa ctg gtg ccg gtg<br>Thr Val Phe Val Thr Cys Pro Phe Val Val Arg Glu Leu Val Pro Val<br>770                          775                      780 | 2653 |
| atg ctg agc cag ggc agt cat gaa gat gaa gcc gcg gtg ctg tta ggt<br>Met Leu Ser Gln Gly Ser His Glu Asp Glu Ala Ala Val Leu Leu Gly<br>                        785                      790                      795 | 2701 |
| gcc tcg ggc tgg cag atg ttc cgt cgc gtg acg ctg ccg aat att cgc<br>Ala Ser Gly Trp Gln Met Phe Arg Arg Val Thr Leu Pro Asn Ile Arg<br>800                          805                      810 | 2749 |
| tgg gcc atg ctg tat ggc gtc gtg ctg acc aac gcc cgc gcg att ggt<br>Trp Ala Met Leu Tyr Gly Val Val Leu Thr Asn Ala Arg Ala Ile Gly<br>815                          820                      825                      830 | 2797 |
| gag ttt ggc gcg gtt tcc gtg gtt tcg ggt tct att cgc ggt gaa acc<br>Glu Phe Gly Ala Val Ser Val Val Ser Gly Ser Ile Arg Gly Glu Thr<br>                        835                      840                      845 | 2845 |
| tac act tta ccg ctt cag gtt gaa tta ctg cat cag gat tac aac acg<br>Tyr Thr Leu Pro Leu Gln Val Glu Leu Leu His Gln Asp Tyr Asn Thr<br>850                          855                      860 | 2893 |
| gtg ggc gcc ttt act gcc gca gcc tta ctg acc gtg atg gca atc gtg<br>Val Gly Ala Phe Thr Ala Ala Ala Leu Leu Thr Val Met Ala Ile Val<br>                        865                      870                      875 | 2941 |
| acg ctg ttt ctg aaa agc att gtg caa tgg cgt tta gag caa cag cac<br>Thr Leu Phe Leu Lys Ser Ile Val Gln Trp Arg Leu Glu Gln Gln His<br>880                          885                      890 | 2989 |
| aaa cgc ctg caa ctg gag gac aat cat gag cat tgagattaac cagatcaaca<br>Lys Arg Leu Gln Leu Glu Asp Asn His Glu His<br>895                          900                      905 | 3042 |
| aatcctttgg tcgcacagcg gtgctgaacg atatctcact ggatattcct tctggccaga | 3102 |
| tggtggcctt actggggccg tccggttccg gtaaaaccac gctgctgcgc atcattgctg | 3162 |
| gactggaaca tcagaacagc ggtcagattc gttttcacga ccacgatgtc agccgcctgc | 3222 |
| acgcccgcga tcgccaggtc ggatttgtct tccagcacta tgcgctgttc cgtcatatga | 3282 |
| cggtcttcga caatattgcc tttggcctga ccgtgctgcc gcgccgtgag cgtccgtcca | 3342 |
| gtgcggaaat taaaaaacgc gtcacgcgcc tgctggagat ggtgcagctt cccatctgg | 3402 |
| cgaaccgttt cccggcccag ctttcgggag gcagaagca gcgcgtcgcg ctggcaagag | 3462 |
| ccctggccgt ggaaccgcaa atcctgttgc tggatgagcc ctttggtgcg ctggacgctc | 3522 |
| aggtgcgtaa agagctgcgc cgttggttac gtcagctgca cgaagaattg aagttcacca | 3582 |
| gcgtgttcgt cacccacgat caggaagagg cgatggaagt ggccgatcgc gtggtggtga | 3642 |
| tgagccaggg cagcatcgaa caggtgggga cgccggatga agtctggcgc gatcccgcca | 3702 |
| cgcgcttcgt gctggaattc ctgggtgagg ttaaccgctt cgacggtgaa gtgcatggtt | 3762 |
| ctcagttcca tgtcggggcg caccactggc cgttaggcta tacctctgca catcagggcg | 3822 |
| cggtcgatct gttcctgcgc ccgtgggaaa tcgacgtttc gcgcagaagt agcctggaaa | 3882 |
| cgccgctgcc cgttcaggtc ttagaagtga gtcctcgtgg tcacttctgg cagctggtgg | 3942 |

```
tgcagccaac gggatggcag agcgagccct tctcgctggt ctttgacggt gaacagaccg    4002
cgccgttgcg cggcgagcgc ctgttcgtgg ggctgcagca ggccagactg taccagggcg    4062
cgacaccgtt acgggcggtt gcctttgcac acagcgcctg ataggttgag tgaatgttaa    4122
acgcccggag gcgcttcccg cgatccgggc tttttaatgg caaggtttgt aacctgtaga    4182
cctgataaga cgcgcaagcg tcgcatcagg caacaccacg tatggataga gatcgtgagt    4242
acattagaac aaacaatagg caatacgcct ctggtgaagt tgcagcgaat ggggccggat    4302
aacggcagtg aagtgtggtt aaaactggaa ggcaataacc cggcaggttc ggtgaaagat    4362
cgtgcggcac tttcgatgat cgtcgaggcg gaaaagcgcg g                        4403
```

<210> SEQ ID NO 44
<211> LENGTH: 337
<212> TYPE: PRT
<213> ORGANISM: Pantoea ananatis

<400> SEQUENCE: 44

```
Met Thr Leu Pro Ala Met Lys Lys Ile Val Ser Gly Leu Ala Leu Ser
 1               5                  10                  15

Leu Ser Leu Ala Gly Ala Ala Asn Ala Thr Glu Leu Leu Asn Ser Ser
            20                  25                  30

Tyr Asp Val Ala Arg Glu Leu Phe Val Ala Leu Asn Ala Pro Phe Val
        35                  40                  45

Ser Gln Trp Asp Ala Ser His Pro Asp Asp Lys Leu Thr Ile Lys Met
    50                  55                  60

Ser His Ala Gly Ser Ser Lys Gln Ala Leu Ala Ile Leu Gln Gly Leu
65                  70                  75                  80

Arg Ala Asp Val Val Thr Tyr Asn Gln Val Thr Asp Val Gln Val Leu
                85                  90                  95

His Asp Lys Gly Lys Leu Ile Pro Ala Asp Trp Gln Thr Arg Leu Pro
            100                 105                 110

Asn Asn Ser Ser Pro Phe Tyr Ser Thr Met Ala Phe Leu Val Arg Lys
        115                 120                 125

Gly Asn Pro Lys Gln Ile His Asp Trp Ser Asp Leu Thr Arg Asp Asp
    130                 135                 140

Val Lys Leu Ile Phe Pro Asn Pro Lys Thr Ser Gly Asn Gly Arg Tyr
145                 150                 155                 160

Thr Tyr Leu Ala Ala Trp Gly Ala Ala Ser Asn Thr Asp Gly Gly Asp
                165                 170                 175

Gln Ala Lys Thr Arg Ala Phe Met Thr Lys Phe Leu Lys Asn Val Glu
            180                 185                 190

Val Phe Asp Thr Gly Gly Arg Gly Ala Thr Thr Thr Phe Ala Glu Arg
        195                 200                 205

Gly Leu Gly Asp Val Leu Ile Ser Phe Glu Ser Glu Val Asn Asn Ile
    210                 215                 220

Arg Asn Gln Tyr Gly Lys Asp Asp Tyr Glu Val Val Pro Lys Thr
225                 230                 235                 240

Asp Ile Leu Ala Glu Phe Pro Val Ala Trp Val Asp Lys Asn Val Glu
                245                 250                 255

Gln Asn Lys Thr Ala Asp Ala Lys Ala Tyr Leu Thr Trp Leu Tyr
            260                 265                 270

Ser Pro Ala Ala Gln Lys Ile Ile Thr Asp Phe Tyr Tyr Arg Val Asn
        275                 280                 285

Asn Pro Gln Leu Met Ala Gln Gln Lys Ala Arg Phe Pro Ala Thr Asn
    290                 295                 300
```

-continued

```
Leu Phe Arg Val Glu Asp Ile Phe Gly Gly Trp Asp Asn Val Met Lys
305                 310                 315                 320

Thr His Phe Ala Ser Gly Gly Glu Leu Asp Gln Leu Leu Ala Ala Gly
                325                 330                 335

Arg

<210> SEQ ID NO 45
<211> LENGTH: 277
<212> TYPE: PRT
<213> ORGANISM: Pantoea ananatis

<400> SEQUENCE: 45

Met Phe Ala Ala Ser Gln Lys Arg Val Leu Pro Gly Phe Gly Leu Ser
1               5                   10                  15

Leu Gly Thr Ser Leu Leu Phe Thr Cys Leu Val Leu Leu Pro Ile
            20                  25                  30

Ser Ala Leu Ile Met Gln Leu Ser Gln Met Thr Leu Gln Gln Tyr Trp
            35                  40                  45

Asp Val Val Thr Asn Pro Gln Leu Ile Ala Ala Tyr Lys Val Thr Leu
        50                  55                  60

Leu Ser Ala Gly Val Ala Ser Leu Phe Asn Ala Val Phe Gly Met Leu
65                  70                  75                  80

Met Ala Trp Ile Leu Thr Arg Tyr Arg Phe Pro Gly Arg Thr Leu Leu
                85                  90                  95

Asp Gly Leu Met Asp Leu Pro Phe Ala Leu Pro Thr Ala Val Ala Gly
            100                 105                 110

Leu Thr Leu Ala Gly Leu Phe Ser Val Asn Gly Trp Tyr Gly Gln Trp
        115                 120                 125

Phe Ala His Phe Asp Ile Lys Ile Ser Tyr Thr Trp Ile Gly Ile Ala
130                 135                 140

Leu Ala Met Ala Phe Thr Ser Ile Pro Phe Val Val Arg Thr Val Gln
145                 150                 155                 160

Pro Val Leu Glu Glu Leu Gly Pro Glu Tyr Glu Glu Ala Ala Gln Thr
                165                 170                 175

Leu Gly Ala Thr Pro Trp Gln Ser Phe Arg Arg Val Val Leu Pro Glu
            180                 185                 190

Val Ala Pro Ala Leu Leu Ala Gly Thr Ala Leu Ser Phe Thr Arg Ser
        195                 200                 205

Leu Gly Glu Phe Gly Ala Val Ile Phe Ile Ala Gly Asn Ile Ala Trp
210                 215                 220

Lys Thr Glu Val Thr Ser Leu Met Ile Phe Val Arg Leu Gln Glu Phe
225                 230                 235                 240

Asp Tyr Pro Ala Ala Ser Ala Ile Ala Ser Val Ile Leu Ala Ala Ser
                245                 250                 255

Leu Leu Leu Leu Phe Ala Ile Asn Thr Leu Gln Ser Arg Phe Gly Arg
            260                 265                 270

Arg Leu Gly Gly His
        275

<210> SEQ ID NO 46
<211> LENGTH: 291
<212> TYPE: PRT
<213> ORGANISM: Pantoea ananatis

<400> SEQUENCE: 46

Met Ala Glu Ile Ser Gln Leu Asn His Ala Asp Arg Gln Pro Val Asn
```

-continued

```
  1               5                  10                 15
Trp Ala Lys Trp Leu Leu Ile Gly Ile Gly Ala Leu Ile Ser Leu Leu
            20                  25                  30

Leu Leu Val Val Pro Met Val Ser Ile Phe Trp Glu Ala Leu His Lys
            35                  40                  45

Gly Leu Gly Val Thr Leu Ser Asn Leu Thr Asp Ser Asp Met Leu His
            50                  55                  60

Ala Ile Trp Leu Thr Val Leu Val Ala Leu Ile Thr Val Pro Val Asn
 65                  70                  75                  80

Leu Val Phe Gly Thr Leu Leu Ala Trp Leu Val Thr Arg Phe Thr Phe
                85                  90                  95

Pro Gly Arg Gln Leu Leu Leu Thr Leu Phe Asp Ile Pro Phe Ala Val
                100                 105                 110

Ser Pro Val Val Ala Gly Leu Met Tyr Leu Leu Phe Trp Gly Ile Asn
            115                 120                 125

Gly Pro Ala Gly Gly Trp Leu Asp Ala His Asn Ile Gln Val Met Phe
            130                 135                 140

Ser Trp Pro Gly Met Val Leu Val Thr Val Phe Val Thr Cys Pro Phe
145                 150                 155                 160

Val Val Arg Glu Leu Val Pro Val Met Leu Ser Gln Gly Ser His Glu
                165                 170                 175

Asp Glu Ala Ala Val Leu Leu Gly Ala Ser Gly Trp Gln Met Phe Arg
            180                 185                 190

Arg Val Thr Leu Pro Asn Ile Arg Trp Ala Met Leu Tyr Gly Val Val
            195                 200                 205

Leu Thr Asn Ala Arg Ala Ile Gly Glu Phe Gly Ala Val Ser Val Val
            210                 215                 220

Ser Gly Ser Ile Arg Gly Glu Thr Tyr Thr Leu Pro Leu Gln Val Glu
225                 230                 235                 240

Leu Leu His Gln Asp Tyr Asn Thr Val Gly Ala Phe Thr Ala Ala Ala
                245                 250                 255

Leu Leu Thr Val Met Ala Ile Val Thr Leu Phe Leu Lys Ser Ile Val
            260                 265                 270

Gln Trp Arg Leu Glu Gln Gln His Lys Arg Leu Gln Leu Glu Asp Asn
            275                 280                 285

His Glu His
        290

<210> SEQ ID NO 47
<211> LENGTH: 1403
<212> TYPE: DNA
<213> ORGANISM: Pantoea ananatis
<220> FEATURE:
<221> NAME/KEY: CDS
<222> LOCATION: (15)..(1103)

<400> SEQUENCE: 47
actggaggac aatc atg agc att gag att aac cag atc aac aaa tcc ttt        50
              Met Ser Ile Glu Ile Asn Gln Ile Asn Lys Ser Phe
                1               5                  10 ggt cgc aca gcg gtg ctg aac gat atc tca ctg gat att cct tct ggc        98
Gly Arg Thr Ala Val Leu Asn Asp Ile Ser Leu Asp Ile Pro Ser Gly
            15                  20                  25 cag atg gtg gcc tta ctg ggg ccg tcc ggt tcc ggt aaa acc acg ctg       146
Gln Met Val Ala Leu Leu Gly Pro Ser Gly Ser Gly Lys Thr Thr Leu
        30                  35                  40 ctg cgc atc att gct gga ctg gaa cat cag aac agc ggt cag att cgt       194
```

```
Leu Arg Ile Ile Ala Gly Leu Glu His Gln Asn Ser Gly Gln Ile Arg
 45                  50                  55                  60 ttt cac gac cac gat gtc agc cgc ctg cac gcc cgc gat cgc cag gtc      242
Phe His Asp His Asp Val Ser Arg Leu His Ala Arg Asp Arg Gln Val
                         65                  70                  75 gga ttt gtc ttc cag cac tat gcg ctg ttc cgt cat atg acg gtc ttc      290
Gly Phe Val Phe Gln His Tyr Ala Leu Phe Arg His Met Thr Val Phe
                 80                  85                  90 gac aat att gcc ttt ggc ctg acc gtg ctg ccg cgt gag cgt ccg          338
Asp Asn Ile Ala Phe Gly Leu Thr Val Leu Pro Arg Glu Arg Pro
             95                 100                 105 tcc agt gcg gaa att aaa aaa cgc gtc acg cgc ctg ctg gag atg gtg      386
Ser Ser Ala Glu Ile Lys Lys Arg Val Thr Arg Leu Leu Glu Met Val
        110                 115                 120 cag ctt tcc cat ctg gcg aac cgt ttc ccg gcc cag ctt tcg gga ggg      434
Gln Leu Ser His Leu Ala Asn Arg Phe Pro Ala Gln Leu Ser Gly Gly
125                 130                 135                 140 cag aag cag cgc gtc gcg ctg gca aga gcc ctg gcc gtg gaa ccg caa      482
Gln Lys Gln Arg Val Ala Leu Ala Arg Ala Leu Ala Val Glu Pro Gln
                145                 150                 155 atc ctg ttg ctg gat gag ccc ttt ggt gcg ctg gac gct cag gtg cgt      530
Ile Leu Leu Leu Asp Glu Pro Phe Gly Ala Leu Asp Ala Gln Val Arg
            160                 165                 170 aaa gag ctg cgc cgt tgg tta cgt cag ctg cac gaa gaa ttg aag ttc      578
Lys Glu Leu Arg Arg Trp Leu Arg Gln Leu His Glu Glu Leu Lys Phe
        175                 180                 185 acc agc gtg ttc gtc acc cac gat cag gaa gag gcg atg gaa gtg gcc      626
Thr Ser Val Phe Val Thr His Asp Gln Glu Glu Ala Met Glu Val Ala
190                 195                 200 gat cgc gtg gtg gtg atg agc cag ggc agc atc gaa cag gtg ggg acg      674
Asp Arg Val Val Val Met Ser Gln Gly Ser Ile Glu Gln Val Gly Thr
205                 210                 215                 220 ccg gat gaa gtc tgg cgc gat ccc gcc acg cgc ttc gtg ctg gaa ttc      722
Pro Asp Glu Val Trp Arg Asp Pro Ala Thr Arg Phe Val Leu Glu Phe
                225                 230                 235 ctg ggt gag gtt aac cgc ttc gac ggt gaa gtg cat ggt tct cag ttc      770
Leu Gly Glu Val Asn Arg Phe Asp Gly Glu Val His Gly Ser Gln Phe
            240                 245                 250 cat gtc ggg gcg cac cac tgg ccg tta ggc tat acc tct gca cat cag      818
His Val Gly Ala His His Trp Pro Leu Gly Tyr Thr Ser Ala His Gln
        255                 260                 265 ggc gcg gtc gat ctg ttc ctg cgc ccg tgg gaa atc gac gtt tcg cgc      866
Gly Ala Val Asp Leu Phe Leu Arg Pro Trp Glu Ile Asp Val Ser Arg
270                 275                 280 aga agt agc ctg gaa acg ccg ctg ccc gtt cag gtc tta gaa gtg agt      914
Arg Ser Ser Leu Glu Thr Pro Leu Pro Val Gln Val Leu Glu Val Ser
285                 290                 295                 300 cct cgt ggt cac ttc tgg cag ctg gtg gtg cag cca acg gga tgg cag      962
Pro Arg Gly His Phe Trp Gln Leu Val Val Gln Pro Thr Gly Trp Gln
                305                 310                 315 agc gag ccc ttc tcg ctg gtc ttt gac ggt gaa cag acc gcg ccg ttg     1010
Ser Glu Pro Phe Ser Leu Val Phe Asp Gly Glu Gln Thr Ala Pro Leu
            320                 325                 330 cgc ggc gag cgc ctg ttc gtg ggg ctg cag cag gcc aga ctg tac cag     1058
Arg Gly Glu Arg Leu Phe Val Gly Leu Gln Gln Ala Arg Leu Tyr Gln
        335                 340                 345 ggc gcg aca ccg tta cgg gcg gtt gcc ttt gca cac agc gcc tga         1103
Gly Ala Thr Pro Leu Arg Ala Val Ala Phe Ala His Ser Ala
350                 355                 360 taggttgagt gaatgttaaa cgcccggagg cgcttcccgc gatccgggct ttttaatggc   1163
```

```
aaggtttgta acctgtagac ctgataagac gcgcaagcgt cgcatcaggc aacaccacgt    1223
atggatagag atcgtgagta cattagaaca aacaataggc aatacgcctc tggtgaagtt    1283
gcagcgaatg gggccggata acggcagtga agtgtggtta aaactggaag caataaccc     1343 ggcaggttcg gtgaaagatc gtgcggcact ttcgatgatc gtcgaggcgg aaaagcgcgg    1403
```

<210> SEQ ID NO 48
<211> LENGTH: 362
<212> TYPE: PRT
<213> ORGANISM: Pantoea ananatis

<400> SEQUENCE: 48

```
Met Ser Ile Glu Ile Asn Gln Ile Asn Lys Ser Phe Gly Arg Thr Ala
1               5                   10                  15

Val Leu Asn Asp Ile Ser Leu Asp Ile Pro Ser Gly Gln Met Val Ala
                20                  25                  30

Leu Leu Gly Pro Ser Gly Ser Gly Lys Thr Thr Leu Leu Arg Ile Ile
            35                  40                  45

Ala Gly Leu Glu His Gln Asn Ser Gly Gln Ile Arg Phe His Asp His
        50                  55                  60

Asp Val Ser Arg Leu His Ala Arg Asp Arg Gln Val Gly Phe Val Phe
65                  70                  75                  80

Gln His Tyr Ala Leu Phe Arg His Met Thr Val Phe Asp Asn Ile Ala
                85                  90                  95

Phe Gly Leu Thr Val Leu Pro Arg Arg Glu Arg Pro Ser Ser Ala Glu
            100                 105                 110

Ile Lys Lys Arg Val Thr Arg Leu Leu Glu Met Val Gln Leu Ser His
        115                 120                 125

Leu Ala Asn Arg Phe Pro Ala Gln Leu Ser Gly Gly Gln Lys Gln Arg
130                 135                 140

Val Ala Leu Ala Arg Ala Leu Ala Val Glu Pro Gln Ile Leu Leu Leu
145                 150                 155                 160

Asp Glu Pro Phe Gly Ala Leu Asp Ala Gln Val Arg Lys Glu Leu Arg
                165                 170                 175

Arg Trp Leu Arg Gln Leu His Glu Glu Leu Lys Phe Thr Ser Val Phe
            180                 185                 190

Val Thr His Asp Gln Glu Glu Ala Met Glu Val Ala Asp Arg Val Val
        195                 200                 205

Val Met Ser Gln Gly Ser Ile Glu Gln Val Gly Thr Pro Asp Glu Val
        210                 215                 220

Trp Arg Asp Pro Ala Thr Arg Phe Val Leu Glu Phe Leu Gly Glu Val
225                 230                 235                 240

Asn Arg Phe Asp Gly Glu Val His Gly Ser Gln Phe His Val Gly Ala
                245                 250                 255

His His Trp Pro Leu Gly Tyr Thr Ser Ala His Gln Gly Ala Val Asp
            260                 265                 270

Leu Phe Leu Arg Pro Trp Glu Ile Asp Val Ser Arg Arg Ser Ser Leu
        275                 280                 285

Glu Thr Pro Leu Pro Val Gln Val Leu Glu Val Ser Pro Arg Gly His
    290                 295                 300

Phe Trp Gln Leu Val Val Gln Pro Thr Gly Trp Gln Ser Glu Pro Phe
305                 310                 315                 320

Ser Leu Val Phe Asp Gly Glu Gln Thr Ala Pro Leu Arg Gly Glu Arg
                325                 330                 335
```

```
Leu Phe Val Gly Leu Gln Gln Ala Arg Leu Tyr Gln Gly Ala Thr Pro
            340                 345                 350

Leu Arg Ala Val Ala Phe Ala His Ser Ala
    355                 360

<210> SEQ ID NO 49
<211> LENGTH: 1779
<212> TYPE: DNA
<213> ORGANISM: Pantoea ananatis
<220> FEATURE:
<221> NAME/KEY: CDS
<222> LOCATION: (301)..(1536)

<400> SEQUENCE: 49
gtcaaaaccc tcaaaaaata aagcaccggg cgcacaacag ggcgcccgct ttttttgatt      60
taaaaaaact tttctcacca ggctgaaatt tggtgactta tgtcacataa ccgtcatcgg     120
cagcgggttc gttcttctcg atgcggccaa cccacgattt tgtctggcaa agtacgtcct     180
ctgagccctg ccatgctggc ggtcaggcaa tcgtttgtat tgccgcaggc gattttttg      240 atattttgac agacggctga ctgcgttcag tcctcgttga attctgaata gggttgggaa     300 atg gca aag gta tca ctg gaa aaa gac aaa att aag ttc ctg ctg gtg       348
Met Ala Lys Val Ser Leu Glu Lys Asp Lys Ile Lys Phe Leu Leu Val
  1               5                  10                  15 gaa ggt gtc cat cag agc gcg ctg gaa aat ctt cgt gct gca ggt tac       396
Glu Gly Val His Gln Ser Ala Leu Glu Asn Leu Arg Ala Ala Gly Tyr
             20                  25                  30 acc aat att gaa ttc cac aaa ggc gca ctg gat gcc gag gcg tta aaa       444
Thr Asn Ile Glu Phe His Lys Gly Ala Leu Asp Ala Glu Ala Leu Lys
         35                  40                  45 gct tcc gct cgc gat gcg cat ttt atc ggt atc cgt tcc cgt tcc caa       492
Ala Ser Ala Arg Asp Ala His Phe Ile Gly Ile Arg Ser Arg Ser Gln
     50                  55                  60 ctg acc gaa gag att ttt gcc gct gca gaa aaa ctg gta gcg gtg ggc       540
Leu Thr Glu Glu Ile Phe Ala Ala Ala Glu Lys Leu Val Ala Val Gly
 65                  70                  75                  80 tgt ttc tgt atc gga acg aat cag gtt gat tta aat gcc gca gcg aaa       588
Cys Phe Cys Ile Gly Thr Asn Gln Val Asp Leu Asn Ala Ala Ala Lys
                 85                  90                  95 cgc ggt atc ccg gtt ttt aac gca cct ttc tca aat acg cgc tct gtg       636
Arg Gly Ile Pro Val Phe Asn Ala Pro Phe Ser Asn Thr Arg Ser Val
            100                 105                 110 gcc gag ctg gtt att ggc gag atg ctg ctg atg ctg cgc ggt gtt ccg       684
Ala Glu Leu Val Ile Gly Glu Met Leu Leu Met Leu Arg Gly Val Pro
        115                 120                 125 gaa gcg aat gcc aaa gcg cac cgt ggt atc tgg aat aaa atc gcc aaa       732
Glu Ala Asn Ala Lys Ala His Arg Gly Ile Trp Asn Lys Ile Ala Lys
    130                 135                 140 ggc tct ttt gaa gcg cgc ggt aaa aag ctg ggt atc att ggc tat ggc       780
Gly Ser Phe Glu Ala Arg Gly Lys Lys Leu Gly Ile Ile Gly Tyr Gly
145                 150                 155                 160 cat atc ggt atg caa ctg ggc gtg ctg gca gaa agt ctg ggc atg cac       828
His Ile Gly Met Gln Leu Gly Val Leu Ala Glu Ser Leu Gly Met His
                165                 170                 175 gtt tac ttc tat gac atc gaa aac aag ctg ccg ttg ggc aac gca tca       876
Val Tyr Phe Tyr Asp Ile Glu Asn Lys Leu Pro Leu Gly Asn Ala Ser
            180                 185                 190 cag gtt cgt agc ctg acg cag ttg cta aat atg agt gac gtt gtc agc       924
Gln Val Arg Ser Leu Thr Gln Leu Leu Asn Met Ser Asp Val Val Ser
        195                 200                 205 ctg cat gtc ccg gaa acc gcc tct acg caa aat atg att tct gcc aat       972
```

```
                                  -continued

Leu His Val Pro Glu Thr Ala Ser Thr Gln Asn Met Ile Ser Ala Asn
210                 215                 220 gag ctg gct cag atg aag cct ggc ggc ctg ctg ata aat gcc tca cgc      1020
Glu Leu Ala Gln Met Lys Pro Gly Gly Leu Leu Ile Asn Ala Ser Arg
225                 230                 235                 240 ggc acc gtg gta gat att cct gct ttg tgc gaa gcg ctg gcc agc aag      1068
Gly Thr Val Val Asp Ile Pro Ala Leu Cys Glu Ala Leu Ala Ser Lys
            245                 250                 255 cag gtt ggt ggc gct gcg att gat gtg ttc cct gta gag ccg gcg acc      1116
Gln Val Gly Gly Ala Ala Ile Asp Val Phe Pro Val Glu Pro Ala Thr
        260                 265                 270 aac agc gat ccg ttt gtt tcc cca ctg agc gaa ttc gac aac gtt atc      1164
Asn Ser Asp Pro Phe Val Ser Pro Leu Ser Glu Phe Asp Asn Val Ile
    275                 280                 285 ctg acg ccg cac atc ggg gga tcg acg gaa gaa gct cag gag aat atc      1212
Leu Thr Pro His Ile Gly Gly Ser Thr Glu Glu Ala Gln Glu Asn Ile
290                 295                 300 ggg att gaa gtc gcg ggc aag ctg gcg aaa tat tcg gat aac ggt tca      1260
Gly Ile Glu Val Ala Gly Lys Leu Ala Lys Tyr Ser Asp Asn Gly Ser
305                 310                 315                 320 acg ctg tcc gcc gtc aat ttc ccg gaa gtg tca ttg ccg atg cac ggc      1308
Thr Leu Ser Ala Val Asn Phe Pro Glu Val Ser Leu Pro Met His Gly
            325                 330                 335 att agc gcc agt cgt ctg ctg cat att cac gaa aac cgt ccg ggc gtt      1356
Ile Ser Ala Ser Arg Leu Leu His Ile His Glu Asn Arg Pro Gly Val
        340                 345                 350 ctc acc gcg atc aac cag att ttc gct gaa caa ggc atc aac att gcc      1404
Leu Thr Ala Ile Asn Gln Ile Phe Ala Glu Gln Gly Ile Asn Ile Ala
    355                 360                 365 gct cag tac ctg caa acc tct ccg atg atg ggt tat gtg gtc atc gac      1452
Ala Gln Tyr Leu Gln Thr Ser Pro Met Met Gly Tyr Val Val Ile Asp
370                 375                 380 att gat gct gag cac gaa ctg gca gag aaa gct ctg caa ctg atg aag      1500
Ile Asp Ala Glu His Glu Leu Ala Glu Lys Ala Leu Gln Leu Met Lys
385                 390                 395                 400 gcg att ccg gga acg att cgc gcc cgc ctg ctt tac tgatcccacg           1546
Ala Ile Pro Gly Thr Ile Arg Ala Arg Leu Leu Tyr
            405                 410 ctgtcaccta cccgggcaca caagcatgcc cgggtttatt catcccatag ccacagtttt    1606
gatggcgtca gcacggccgg caaaggaatg tcccacgccg ctgtaggcag cgcgtcaacc    1666
cgctgacagt catgagcgat gcccaccggt aaaaacccat gctgtttcca gttctgtaag    1726
gtgcgatcgt agaagccgcc ccccattcct aaacgctgtc cggcgcgatc gaa           1779

<210> SEQ ID NO 50
<211> LENGTH: 412
<212> TYPE: PRT
<213> ORGANISM: Pantoea ananatis

<400> SEQUENCE: 50

Met Ala Lys Val Ser Leu Glu Lys Asp Lys Ile Lys Phe Leu Leu Val
1               5                   10                  15

Glu Gly Val His Gln Ser Ala Leu Glu Asn Leu Arg Ala Ala Gly Tyr
            20                  25                  30

Thr Asn Ile Glu Phe His Lys Gly Ala Leu Asp Ala Glu Ala Leu Lys
        35                  40                  45

Ala Ser Ala Arg Asp Ala His Phe Ile Gly Ile Arg Ser Arg Ser Gln
    50                  55                  60

Leu Thr Glu Glu Ile Phe Ala Ala Ala Glu Lys Leu Val Ala Val Gly
```

```
                65                  70                  75                  80
Cys Phe Cys Ile Gly Thr Asn Gln Val Asp Leu Asn Ala Ala Ala Lys
                    85                  90                  95
Arg Gly Ile Pro Val Phe Asn Ala Pro Phe Ser Asn Thr Arg Ser Val
                100                 105                 110
Ala Glu Leu Val Ile Gly Glu Met Leu Leu Met Leu Arg Gly Val Pro
                115                 120                 125
Glu Ala Asn Ala Lys Ala His Arg Gly Ile Trp Asn Lys Ile Ala Lys
                130                 135                 140
Gly Ser Phe Glu Ala Arg Gly Lys Lys Leu Gly Ile Gly Tyr Gly
145                 150                 155                 160
His Ile Gly Met Gln Leu Gly Val Leu Ala Glu Ser Leu Gly Met His
                    165                 170                 175
Val Tyr Phe Tyr Asp Ile Glu Asn Lys Leu Pro Leu Gly Asn Ala Ser
                    180                 185                 190
Gln Val Arg Ser Leu Thr Gln Leu Leu Asn Met Ser Asp Val Val Ser
                    195                 200                 205
Leu His Val Pro Glu Thr Ala Ser Thr Gln Asn Met Ile Ser Ala Asn
210                 215                 220
Glu Leu Ala Gln Met Lys Pro Gly Gly Leu Leu Ile Asn Ala Ser Arg
225                 230                 235                 240
Gly Thr Val Val Asp Ile Pro Ala Leu Cys Glu Ala Leu Ala Ser Lys
                    245                 250                 255
Gln Val Gly Gly Ala Ala Ile Asp Val Phe Pro Val Glu Pro Ala Thr
                260                 265                 270
Asn Ser Asp Pro Phe Val Ser Pro Leu Ser Glu Phe Asp Asn Val Ile
                275                 280                 285
Leu Thr Pro His Ile Gly Gly Ser Thr Glu Glu Ala Gln Glu Asn Ile
                290                 295                 300
Gly Ile Glu Val Ala Gly Lys Leu Ala Lys Tyr Ser Asp Asn Gly Ser
305                 310                 315                 320
Thr Leu Ser Ala Val Asn Phe Pro Glu Val Ser Leu Pro Met His Gly
                    325                 330                 335
Ile Ser Ala Ser Arg Leu Leu His Ile His Glu Asn Arg Pro Gly Val
                    340                 345                 350
Leu Thr Ala Ile Asn Gln Ile Phe Ala Glu Gln Gly Ile Asn Ile Ala
                    355                 360                 365
Ala Gln Tyr Leu Gln Thr Ser Pro Met Met Gly Tyr Val Val Ile Asp
                370                 375                 380
Ile Asp Ala Glu His Glu Leu Ala Glu Lys Ala Leu Gln Leu Met Lys
385                 390                 395                 400
Ala Ile Pro Gly Thr Ile Arg Ala Arg Leu Leu Tyr
                    405                 410

<210> SEQ ID NO 51
<211> LENGTH: 36
<212> TYPE: DNA
<213> ORGANISM: Artificial Sequence
<220> FEATURE:
<223> OTHER INFORMATION: primer P11

<400> SEQUENCE: 51
agctgagtcg acccccagga aaaattggtt aataac                             36

<210> SEQ ID NO 52
<211> LENGTH: 33
```

<212> TYPE: DNA
<213> ORGANISM: Artificial Sequence
<220> FEATURE:
<223> OTHER INFORMATION: primer P12

<400> SEQUENCE: 52
agctgagcat gcttccaact gcgctaatga cgc                                    33

<210> SEQ ID NO 53
<211> LENGTH: 33
<212> TYPE: DNA
<213> ORGANISM: Artificial Sequence
<220> FEATURE:
<223> OTHER INFORMATION: primer P13

<400> SEQUENCE: 53
agctgatcta gaaaacagaa tttgcctggc ggc                                    33

<210> SEQ ID NO 54
<211> LENGTH: 33
<212> TYPE: DNA
<213> ORGANISM: Artificial Sequence
<220> FEATURE:
<223> OTHER INFORMATION: primer P14

<400> SEQUENCE: 54
agctgaggat ccaggaagag tttgtagaaa cgc                                    33

<210> SEQ ID NO 55
<211> LENGTH: 32
<212> TYPE: DNA
<213> ORGANISM: Artificial Sequence
<220> FEATURE:
<223> OTHER INFORMATION: primer P15

<400> SEQUENCE: 55
agctgagtcg acgtgttcgc tgaatacggg gt                                     32

<210> SEQ ID NO 56
<211> LENGTH: 32
<212> TYPE: DNA
<213> ORGANISM: Artificial Sequence
<220> FEATURE:
<223> OTHER INFORMATION: primer P16

<400> SEQUENCE: 56
agctgatcta gagaaagcat caggattgca gc                                     32

<210> SEQ ID NO 57
<211> LENGTH: 59
<212> TYPE: DNA
<213> ORGANISM: Artificial Sequence
<220> FEATURE:
<223> OTHER INFORMATION: primer P17
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t

```
<220> FEATURE:
<221> NAME/KEY: misc_feature
<222> LOCATION: (51)..(51)
<223> OTHER INFORMATION: n is a, c, g, or t

<400> SEQUENCE: 57
atcgtgaaga tcttttccag tgttnannag ggtgccttgc acggtnatna ngtcactgg      59

<210> SEQ ID NO 58
<211> LENGTH: 32
<212> TYPE: DNA
<213> ORGANISM: Artificial Sequence
<220> FEATURE:
<223> OTHER INFORMATION: primer P18
<220> FEATURE:
<221> NAME/KEY: misc_feature
<222> LOCATION: (16)..(20)
<223> OTHER INFORMATION: n is a, c, g, or t

<400> SEQUENCE: 58
tggaaaagat cttcannnnn cgctgacctg cg                                   32

<210> SEQ ID NO 59
<211> LENGTH: 60
<212> TYPE: DNA
<213> ORGANISM: Artificial Sequence
<220> FEATURE:
<223> OTHER INFORMATION: primer P19

<400> SEQUENCE: 59
tccgctcacg atttttttca tcgctggtaa ggtcatttat cccccaggaa aaattggtta     60

<210> SEQ ID NO 60
<211> LENGTH: 63
<212> TYPE: DNA
<213> ORGANISM: Artificial Sequence
<220> FEATURE:
<223> OTHER INFORMATION: primer P20

<400> SEQUENCE: 60
tttcacaccg ctcaaccgca gggcataacc ggcccttgaa gcctgctttt ttatactaag     60
ttg                                                                   63

<210> SEQ ID NO 61
<211> LENGTH: 20
<212> TYPE: DNA
<213> ORGANISM: Artificial Sequence
<220> FEATURE:
<223> OTHER INFORMATION: primer P21

<400> SEQUENCE: 61
ctttgtccct ttagtgaagg                                                 20

<210> SEQ ID NO 62
<211> LENGTH: 44
<212> TYPE: DNA
<213> ORGANISM: Artificial Sequence
<220> FEATURE:
<223> OTHER INFORMATION: primer P22

<400> SEQUENCE: 62
agctgatcta gaagctgact cgagttaatg gcctcccaga cgac                      44

<210> SEQ ID NO 63
<211> LENGTH: 33
<212> TYPE: DNA
<213> ORGANISM: Artificial Sequence
```

```
<220> FEATURE:
<223> OTHER INFORMATION: primer P23

<400> SEQUENCE: 63
agctgagtcg acatggcaaa ggtatcactg gaa                                33

<210> SEQ ID NO 64
<211> LENGTH: 34
<212> TYPE: DNA
<213> ORGANISM: Artificial Sequence
<220> FEATURE:
<223> OTHER INFORMATION: primer P24

<400> SEQUENCE: 64
gagaacgccc gggcgggctt cgtgaatatg cagc                               34

<210> SEQ ID NO 65
<211> LENGTH: 32
<212> TYPE: DNA
<213> ORGANISM: Artificial Sequence
<220> FEATURE:
<223> OTHER INFORMATION: primer P25

<400> SEQUENCE: 65
agctgatcta gacgtgggat cagtaaagca gg                                 32

<210> SEQ ID NO 66
<211> LENGTH: 22
<212> TYPE: DNA
<213> ORGANISM: Artificial Sequence
<220> FEATURE:
<223> OTHER INFORMATION: primer P26

<400> SEQUENCE: 66
aaaaccgccc gggcgttctc ac                                            22

<210> SEQ ID NO 67
<211> LENGTH: 147
<212> TYPE: DNA
<213> ORGANISM: Artificial Sequence
<220> FEATURE:
<223> OTHER INFORMATION: promoter Pnlp

<400> SEQUENCE: 67
aaaacgtgag gaaatacctg gattttcct ggttattttg ccgcaggtca gcgtatcgtg    60
aagatctttt ccagtgttca gtagggtgcc ttgcacggta attatgtcac tggttattaa   120
ccaatttttc ctgggggata aatgagc                                      147
```